United States Patent
Agrofoglio et al.

(10) Patent No.: US 11,603,380 B2
(45) Date of Patent: Mar. 14, 2023

(54) ANTIVIRAL ACYCLONUCLEOSIDE ANALOGUES FOR USE IN TREATING A VIRAL INFECTION

(71) Applicants: Centre national de la recherche scientifique, Orléans (FR); UNIVERSITE D'ORLEANS, Orleans (FR); NEOVIRTECH, Toulouse (FR)

(72) Inventors: Luigi Agrofoglio, Paris (FR); Vincent Roy, Outarville (FR); Coralie De Schutter, Lille (FR); Maxime Bessieres, Les Loges (FR); Franck Gallardo, Montauban (FR)

(73) Assignees: CENTRE NATIONAL DE LA RECHERCHE SCIENTIFIQUE, Paris (FR); UNIVERSITE D'ORLEANS, Orleans (FR); NEOVIRTECH, Toulouse (FR)

( * ) Notice: Subject to any disclaimer, the term of this patent is extended or adjusted under 35 U.S.C. 154(b) by 127 days.

(21) Appl. No.: 17/050,263

(22) PCT Filed: Apr. 23, 2019

(86) PCT No.: PCT/EP2019/060366
§ 371 (c)(1),
(2) Date: Oct. 23, 2020

(87) PCT Pub. No.: WO2019/206907
PCT Pub. Date: Oct. 31, 2019

(65) Prior Publication Data
US 2021/0079031 A1 Mar. 18, 2021

(30) Foreign Application Priority Data
Apr. 23, 2018 (EP) .................... 18305498

(51) Int. Cl.
| C07F 9/6512 | (2006.01) |
| C07F 9/6521 | (2006.01) |
| A61P 31/12 | (2006.01) |
| A61P 31/20 | (2006.01) |

(52) U.S. Cl.
CPC ............ *C07F 9/6521* (2013.01); *A61P 31/12* (2018.01); *C07F 9/6512* (2013.01)

(58) Field of Classification Search
CPC ...... C07F 9/6512; C07F 9/6521; A61P 31/12; A61P 31/20
See application file for complete search history.

(56) References Cited

U.S. PATENT DOCUMENTS

| 6,818,633 B2 | 11/2004 | Balzarini. et al. |
| 7,579,332 B2 | 8/2009 | Krawczyk |
| 2003/0109499 A1 | 6/2003 | Holy et al. |
| 2005/0038058 A1 | 2/2005 | Balzarini. et al. |
| 2005/0059637 A1 | 3/2005 | Krawczyk |
| 2006/0252729 A1 | 11/2006 | Krawczyk |

FOREIGN PATENT DOCUMENTS

| CH | 587 504 | 5/1977 |
| EP | 0532423 | 3/1993 |
| GB | 1457912 A | * 12/1976 ................ C07F 9/40 |

OTHER PUBLICATIONS

Rowe, Raymond C, Paul J. Sheskey, and Marian E Quinn. Handbook of Pharmaceutical Excipients. London: Pharmaceutical Press, 6th Edition, 2009, pp. 17-19. (Year: 2009).*
International Search Report for PCT/EP2019/060366 dated May 27, 2019.
V. S Reznik, et al., "Synthesis and properties or pyrimidinylalkylphosphonic acids", (Jan. 1, 1971), pp. 2108-2113, Bulletin of the Academy of Sciences of the USSR Division of Chemical Science, XP055496836.
International Preliminary Report on Patentability for PCT/EP2019/060366 dated Oct. 27, 2020.

* cited by examiner

*Primary Examiner* — Laura L Stockton
(74) *Attorney, Agent, or Firm* — B. Aaron Schulman, Esq.; Stites & Harbison, PLLC

(57) ABSTRACT

The present invention concerns a compound having the following formula (I):

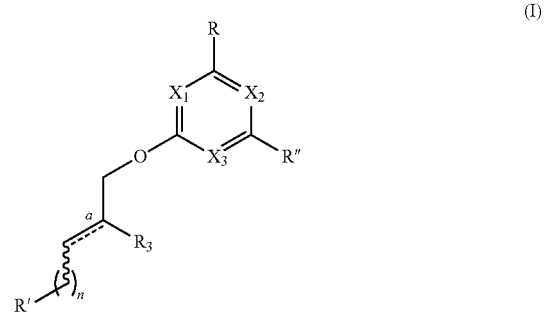

as well as its use as a medicament, especially for its use for treating viral infections.

14 Claims, 9 Drawing Sheets

ANTIVIRAL ACYCLONUCLEOSIDE ANALOGUES FOR USE IN TREATING A VIRAL INFECTION

The present invention concerns new acyclonucleoside analogues having reduced toxicity and enhanced antiviral activity, and pharmaceutically accepted salts and solvates thereof, as well as their preparation methods. The present invention also concerns said acyclonucleoside analogues as antiviral compounds, especially for the treatment of viral infections due to DNA viruses.

DNA viruses and retroviruses cause severe diseases spreading among the world population. Current therapies often need permanent drug administration to maintain low or undetectable viral levels in patients. Some acyclic nucleoside phosphonates (ANPs) are antiviral agents with activity against DNA viruses. Their activities depend on metabolic conversion by two salvage pathway kinases (NMP and NDP kinases) to their diphosphates (ANP-PPs), followed by a specific interaction with the virus DNA polymerase. However, antiviral treatment involving nucleoside or nucleotide analogues frequently result in the selection of resistant virus strains, with precise point mutations in the DNA polymerase gene. There is a need for improved antiviral compounds, especially with enhanced activity and reduced toxicity against DNA viruses.

The aim of the present invention is to provide new acyclonucleoside derivatives with a high antiviral activity and reduced toxicity.

Another aim of the present invention is to provide broad-spectrum antiviral agents able to be active against DNA viruses in particular.

Another aim of the present invention is to provide antiviral agents having a higher antiviral activity in comparison with the known antiviral agents.

Another aim of the present invention is to provide antiviral agents having a reduced toxicity.

The present invention relates to a compound having the following formula (I):

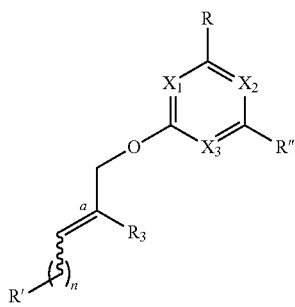

(I)

wherein:
n is 0, 1 or 2;
"a" is a single or a double bond;
$X_1$, $X_2$, and $X_3$ are, independently from each other, CH or N, preferably one of them being N;
R" is chosen from the group consisting of: H, $NH_2$, and halogen atoms such as Cl;
R is chosen from the group consisting of:
—$NR_aR_b$ groups, $R_a$ and $R_b$ being independently from each other H, a ($C_1$-$C_6$)alkyl group or a ($C_3$-$C_6$) cycloalkyl group;
halogen atoms; and
($C_1$-$C_6$)alkoxy groups;

R' is a group of formula (1)

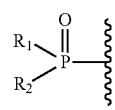

(1)

wherein $R_1$ and $R_2$ are independently from each other chosen from the group consisting of:
OH;
($C_1$-$C_6$)alkoxy groups;
—O-$A_1$-O-$A_2$ groups; wherein $A_1$ is an alkylene radical comprising from 1 to 6 carbon atoms, and $A_2$ is a ($C_1$-$C_{20}$)alkyl group, $A_1$ being preferably a $C_3$-alkylene radical and $A_2$ being a $C_{16}$ alkyl group;
—O-$A_3$-O—C($=$O)-$A_4$, wherein $A_3$ is an alkylene radical comprising from 1 to 6 carbon atoms, and $A_4$ is a ($C_1$-$C_6$)alkyl group, $A_3$ being preferably a $CH_2$ radical and $A_4$ being a tertiobutyl group;
—O-$A_5$-O—C($=$O)—O-$A_6$, wherein $A_5$ is an alkylene radical comprising from 1 to 6 carbon atoms, and $A_6$ is a ($C_1$-$C_6$)alkyl group, $A_5$ being preferably a $CH_2$ radical and $A_6$ being a isopropyl;
or R' is a group of formula (2):

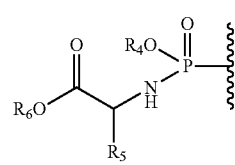

(2)

wherein:
$R_4$ is a ($C_6$-$C_{10}$)aryl group;
$R_5$ is a ($C_1$-$C_6$)alkyl group,
$R_6$ is chosen from the group consisting of: ($C_1$-$C_6$)alkyl groups, and ($C_6$-$C_{10}$)aryl groups,
$R_3$ is chosen from the group consisting of:
H;
($C_1$-$C_6$)alkyl groups;
-$A_7$-OH, wherein $A_7$ is an alkylene radical comprising from 1 to 6 carbon atoms; and
-$A_8$-O—C($=$O)-$A_9$, wherein $A_8$ is an alkylene radical comprising from 1 to 6 carbon atoms, and $A_9$ is a ($C_1$-$C_6$)alkyl group;
as well as its pharmaceutically acceptable salts or its racemates, diastereoisomers or enantiomers.

The compounds of the invention are thus acyclonucleoside derivatives with an improved antiviral activity and reduced toxicity.

Within the present invention, the expression "$C_t$-$C_z$ where t and z can take the values from 1 to 7" means a carbon-based chain which can have from t to z carbon atoms, for example $C_1$-$C_3$ means a carbon-based chain which can have from 1 to 3 carbon atoms.

Within the present invention, the term "halogen atom" means: a fluorine, a chlorine, a bromine or an iodine.

According to the invention, the term "alkyl group" means: a linear or branched, saturated, hydrocarbon-based aliphatic group comprising, unless otherwise mentioned, from 1 to 6 carbon atoms. By way of examples, mention may be made of methyl, ethyl, n-propyl, isopropyl, butyl, isobutyl, tert-butyl or pentyl groups.

According to the invention, the term "cycloalkyl group" means: a cyclic carbon-based group comprising, unless otherwise mentioned, from 3 to 6 carbon atoms. By way of examples, mention may be made of cyclopropyl, cyclobutyl, cyclopentyl, cyclohexyl, etc. groups.

Within the present invention, the term "alkoxy group" means: an —O-alkyl radical where the alkyl group is as previously defined. By way of examples, mention may be made of —O—($C_1$-$C_4$)alkyl groups, and in particular the —O-methyl group, the —O-ethyl group as —O—$C_3$alkyl group, the —O-propyl group, the —O-isopropyl group, and as —O—$C_4$alkyl group, the —O-butyl, —O-isobutyl or —O-tert-butyl group.

Within the present invention, the term "aryl group" means: a cyclic aromatic group comprising between 6 and 10 carbon atoms. By way of examples of aryl groups, mention may be made of phenyl or naphthyl groups.

According to an embodiment, the compounds according to the invention have the following formula (I-1):

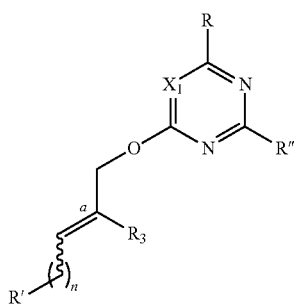

(I-1)

wherein n, a, $X_1$, R", R', R, and $R_3$ are as defined above in formula (I).

Preferably, in formula (I-1), $X_1$ is $CH_2$.

The compounds of formula (I-1) correspond to compounds of formula (I) wherein $X_2$ and $X_3$ are N.

According to a preferred embodiment, in formula (I) and (I-1), "a" is a double bond.

Preferably, in formula (I) and (I-1), R" is chosen from the group consisting of: H, $NH_2$, and Cl; and more preferably is $NH_2$.

Another preferred family of compounds of the invention consists in compounds with the following formula (I'):

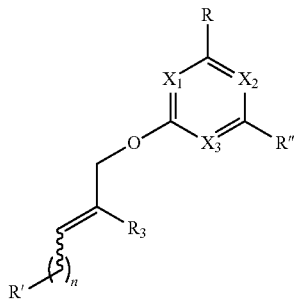

(I')

n, $X_1$, $X_2$, $X_3$, R, R', R", and $R_3$ being as defined above in formula (I), as well as its pharmaceutically acceptable salts or its racemates, diastereoisomers or enantiomers.

Another preferred family of compounds of the invention consists in compounds with the following formula (I-2) or (I'-2):

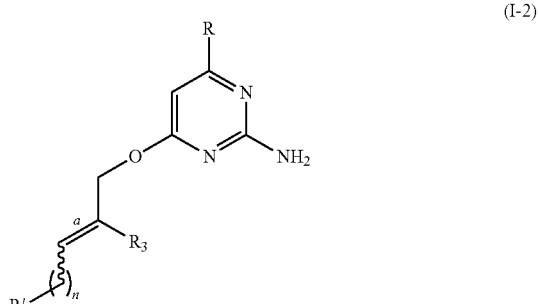

(I-2)

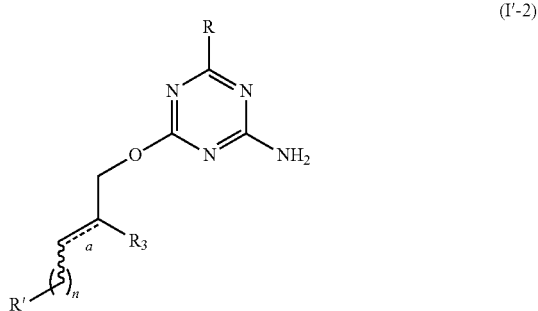

(I'-2)

wherein n, a, R', R, and $R_3$ are as defined above in formula (I).

Preferably, in formula (I-2) or (I'-2), "a" is a double bond.

According to an embodiment, the compounds of the invention have the following formula (II) or (II'):

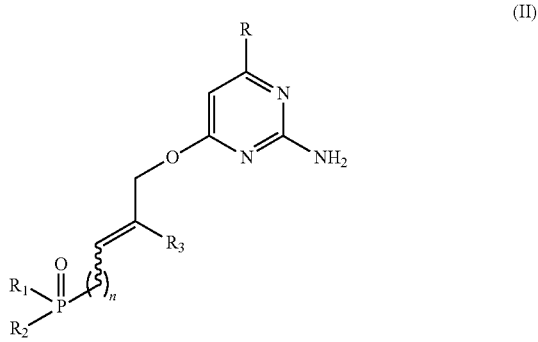

(II)

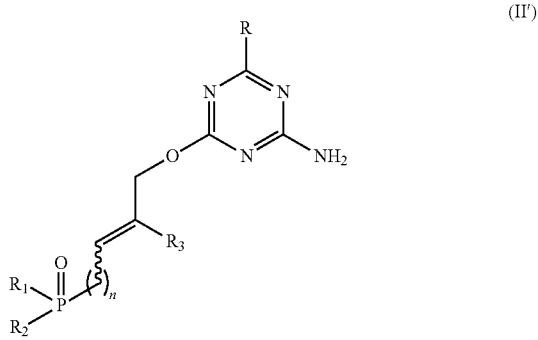

(II')

wherein n, R, $R_1$, $R_2$ and $R_3$ are as defined above in formula (I), as well as its pharmaceutically acceptable salts or its racemates, diastereoisomers or enantiomers.

The compounds of formula (II) correspond to compounds of formula (I-2) wherein R' is a group of formula (1) and "a" is a double bond.

The compounds of formula (II') correspond to compounds of formula (I'-2) wherein R' is a group of formula (1) and "a" is a double bond.

According to an embodiment, in formulae (I), (I'), (I-1), (I-2), (I'-2), (II), and (II'), $R_3$ is chosen from the group consisting of: H, ($C_1$-$C_6$)alkyl groups, and -$A_8$-O—C(=O)-$A_9$, $A_8$ and $A_9$ being as defined above.

Preferably, in formulae (I), (I'), (I-1), (I-2), (I'-2), (II), and (II'), $R_3$ is H, methyl or —$CH_2OCOCH_3$, and more preferably $R_3$ is H or —$CH_2OCOCH_3$.

According to an embodiment, in formulae (I), (I'), (I-1), (I-2), (I'-2), (II), and (II'), R is chosen from the group consisting of: —$NR_aR_b$ groups, $R_a$ and $R_b$ being independently from each other H or a ($C_1$-$C_6$)alkyl group; halogen atoms; and ($C_1$-$C_6$)alkoxy groups.

According to an embodiment, in formulae (I), (I'), (I-1), (I-2), (I'-2), (II), and (II'), R is chosen from the group consisting of: —$NH_2$, Cl, and methoxy.

Preferably, in formulae (I), (I'), (I-1), (I-2), (I'-2), (II), and (II'), R is $NH_2$.

According to a preferred embodiment, the compounds of the invention have the following formula (III):

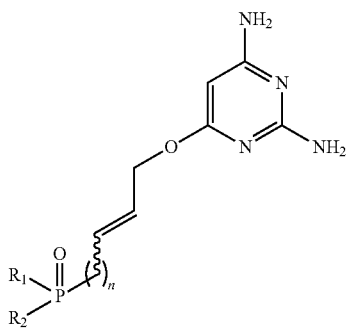

(III)

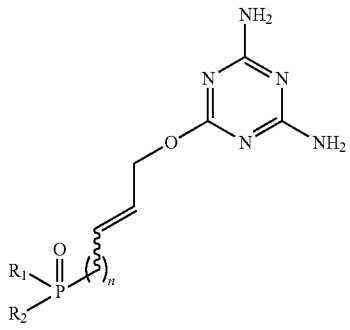

(III')

wherein n, $R_1$, and $R_2$ are as defined above in formula (I), as well as its pharmaceutically acceptable salts or its racemates, diastereoisomers or enantiomers.

According to a preferred embodiment, in formula (1), $R_1$ and $R_2$, identical or different, are chosen from the group consisting of:
—O-$A_1$-O-$A_2$,
—O-$A_3$-O—C(=O)-$A_4$, and
—O-$A_5$-O—C(=O)—O-$A_6$ groups,
$A_1$, $A_2$, $A_3$, $A_4$, $A_5$, and $A_6$ being as defined above.

Preferably, $R_1$ and $R_2$, identical or different, are chosen from the group consisting of:
—O—($CH_2$)$_3$—O—($CH_2$)$_{15}$—$CH_3$,
—O—$CH_2$—O—C(=O)-tBu, and
—O—$CH_2$—O—C(=O)—O-iPr.

According to a preferred embodiment, in formula (1): either $R_1$ is —O—($CH_2$)$_3$—O—($CH_2$)$_{15}$—$CH_3$ and $R_2$ is —O—$CH_2$—O—C(=O)—O-iPr, or $R_1$ and $R_2$ are identical and are —O—$CH_2$—O—C(=O)-tBu or —O—$CH_2$—O—C(=O)—O-iPr.

Preferably, the compounds of the invention have the following formula (IV):

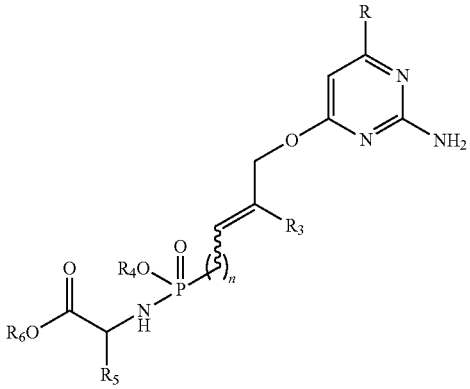

(IV)

wherein n, R, $R_3$, $R_4$, $R_5$ and $R_6$ are as defined above in formula (I), as well as its pharmaceutically acceptable salts or its racemates, diastereoisomers or enantiomers.

The compounds of formula (IV) correspond to compounds of formula (I-2) wherein R' is a group of formula (2) and "a" is a double bond.

In formula (IV), the phosphorus atom and the carbon atom bearing $R_5$ are asymmetric atoms. So, the compounds of formula (IV), as explained hereafter, exist in the form of enantiomers or of diastereoisomers.

According to an embodiment, in formula (IV), $R_3$ is chosen from the group consisting of: H, ($C_1$-$C_6$)alkyl groups, and -$A_8$-O—C(=O)-$A_9$, $A_8$ and $A_9$ being as defined above.

Preferably, in formula (IV), $R_3$ is H, methyl or —$CH_2OCOCH_3$, and more preferably $R_3$ is H or —$CH_2OCOCH_3$.

According to an embodiment, in formula (IV), R is chosen from the group consisting of: —$NR_aR_b$ groups, $R_a$ and $R_b$ being independently from each other H or a ($C_1$-$C_6$) alkyl group; halogen atoms; and ($C_1$-$C_6$)alkoxy groups.

According to an embodiment, in formula (IV), R is chosen from the group consisting of: —$NH_2$, Cl, and methoxy. Preferably, in formula (IV), R is $NH_2$.

Preferably, in formula (IV), $R_4$ is a phenyl or naphthyl group.

The compounds of formula (I), (I'), (I-1), (I-2), (I'-2), (II), (II'), (III), (III') or (IV) can comprise one or more asymmetric carbon and/or phosphorus atoms. They can therefore exist in the form of enantiomers or of diastereoisomers. These enantiomers and diastereoisomers, and also mixtures thereof, including racemic mixtures, form part of the invention.

The compounds of formula (I), (I'), (I-1), (I-2), (I'-2), (II), (II'), (III), (III') or (IV) can exist in the form of bases or of addition salts with acids. Such addition salts form part of the invention.

The compounds of formula (I), (I'), (I-1), (I-2), (I'-2), (II), (II'), (III), (III') or (IV) can exist in the form of pharmaceutically acceptable salts.

These salts can be prepared with pharmaceutically acceptable acids, but the salts of other acids that are of use, for example, for purifying or isolating the compounds of formula (I), (I'), (I-1), (I-2), (I'-2), (II), (II'), (III), (III') or (IV) also form part of the invention.

The present invention also relates to the following preferred compounds:

(1)
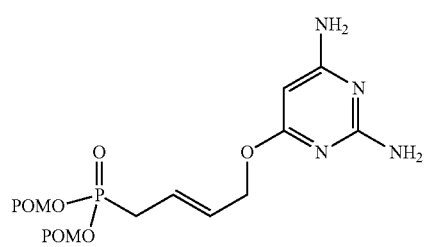

(2)
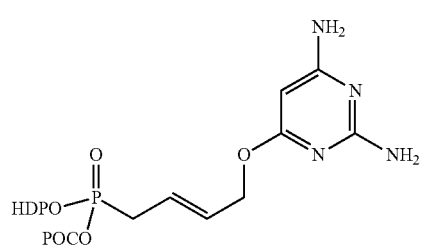

(3)
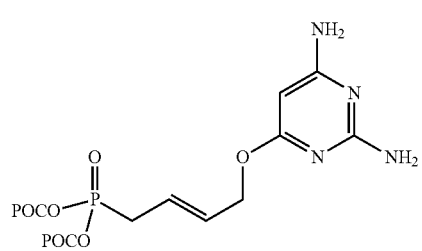

(4)
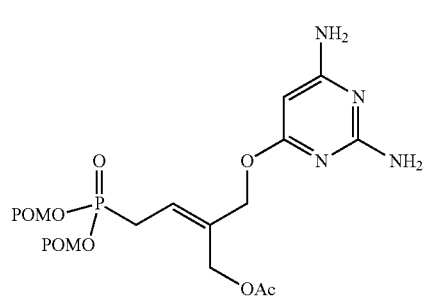

-continued (5)
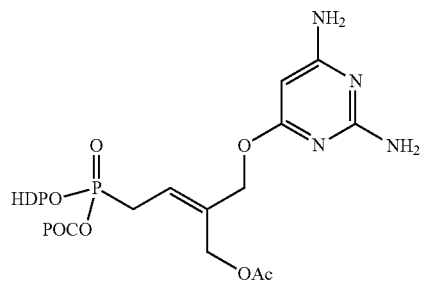

(6)
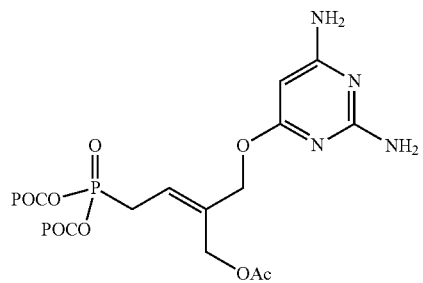

(7)
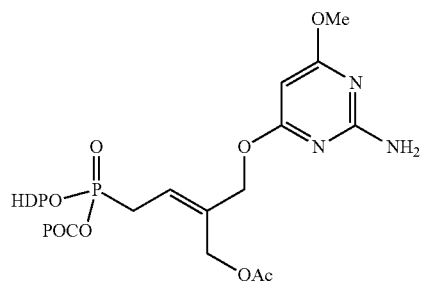

(8)
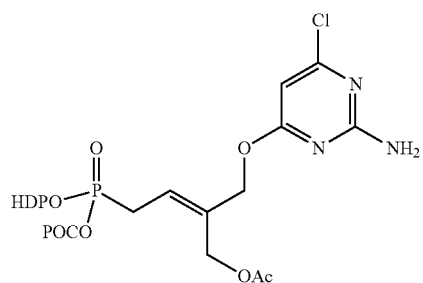

(9)
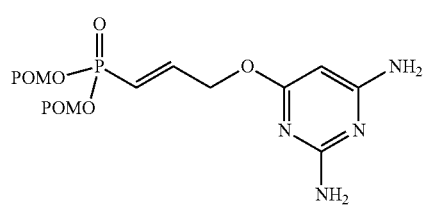

(10)
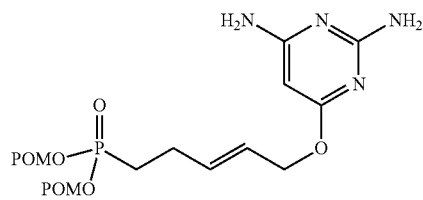

-continued

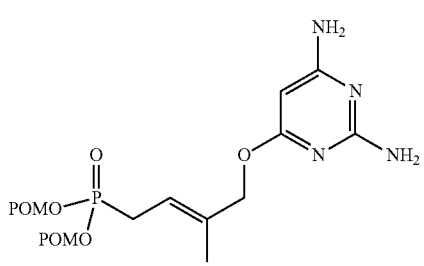

(11)

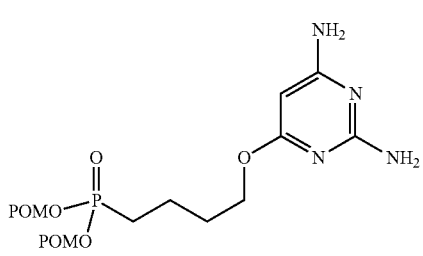

(12)

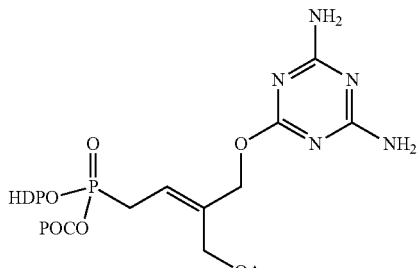

(13)

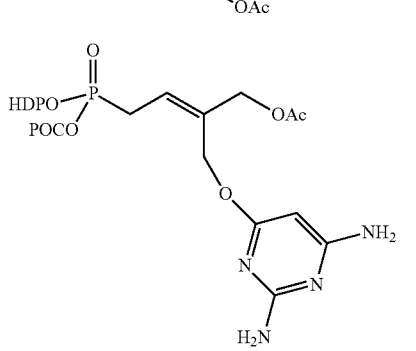

(14)

The present invention also relates to a medicament comprising a compound of formula (I), but also of any of formulae (I), (I'), (I-1), (I-2), (I'-2), (II), (II'), (III), (III') or (IV), or of any of compounds of formulae (1), (2), (3), (4), (5), (6), (7), (8), (9), (10), (11), (12), (13) or (14), or a pharmaceutically acceptable salt thereof.

The present invention also relates to a pharmaceutical composition, comprising a compound of formula (1), but also of any of formulae (I'), (I-1), (I-2), (I'-2), (II), (II'), (III), (III') or (IV), or of any of compounds of formulae (1), (2), (3), (4), (5), (6), (7), (8), (9), (10), (11), (12), (13) or (14), or a pharmaceutically acceptable salt thereof, and also at least one pharmaceutically acceptable excipient.

According to an embodiment, the pharmaceutical compositions provided herein contain therapeutically effective amounts of one or more of the compounds provided herein that are useful in the prevention, treatment, or amelioration of one or more of the symptoms of diseases or disorders associated with viral infections and a pharmaceutically acceptable vehicle. Pharmaceutical vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in some embodiments, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In some embodiments, the compounds described above are formulated into pharmaceutical compositions using techniques and procedures well known in the art (see, e.g., Ansel Introduction to Pharmaceutical Dosage Forms, Seventh Edition (1999).

In the compositions, effective concentrations of one or more compounds of formula (I) or pharmaceutically acceptable derivatives thereof is (are) mixed with a suitable pharmaceutical vehicle. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with associated with viral infections. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the pharmaceutically acceptable vehicle in an amount sufficient to exert a therapeutically useful effect in the absence of undesirable side effects on the patient treated. The therapeutically effective concentration may be determined empirically by testing the compounds in in vitro and in vivo systems well known to those of skill in the art and then extrapolated therefrom for dosages for humans.

The concentration of active compound of formula (I) in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with viral infections or inappropriate cell proliferation, as described herein.

In some embodiments, a therapeutically effective dosage should produce a serum concentration of active ingredient of from about 0.1 ng/ml to about 50-100 µg/ml. The pharmaceutical compositions, in other embodiments, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a vehicle, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The active materials can also be mixed with other active materials which do not impair the desired action, or with materials that supplement the desired action, such as antacids, H2 blockers, and diuretics. The active ingredient is a compound of formula (I) or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For nasal administration, the preparation may contain an esterified phosphonate compound dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

Other routes of administration, such as transdermal patches, including iontophoretic and electrophoretic devices, and rectal administration, are also contemplated herein.

Transdermal patches, including iotophoretic and electrophoretic devices, are well known to those of skill in the art.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same pharmaceutically acceptable substance and by the same methods as for formulations for oral administration.

The present invention also relates to a compound of formula (I), but also of any of formulae (I'), (I-1), (I-2), (I'-2), (II), (II'), (III), (III') or (IV), or of any of compounds of formulae (1), (2), (3), (4), (5), (6), (7), (8), (9), (10), (11), (12), (13) or (14), for its use for the treatment of viral infections.

Preferably, said viral infections are infections due to DNA viruses.

Preferably, the viral infections are infections due to viruses chosen from the group consisting of: Hepatitis B virus, Varicella-zoster virus, Cytomegalovirus, Adenovirus, Herpes virus, in particular Herpes simplex virus types 1 & 2 (human HSV-1 and HSV-2), Poxvirus, Feline corona virus, Filovirus, Papovavirus, Parvovirus, Myxoma virus and Hepadnavirus.

According to an embodiment, the viral infections are due to viruses chosen from animal herpes viruses, such as horse, bovine, turtle, and cat herpes viruses.

According to an embodiment, the viral infections are due to viruses chosen from fowlpox or canarypox viruses.

Methods of treating, preventing, or ameliorating one or more symptoms of diseases associated with viral infections using the compounds and compositions of the invention are provided. In practicing the methods, effective amounts of the compounds or compositions containing therapeutically effective concentrations of the compounds are administered. In certain embodiments, the methods provided herein are for the preventing, or ameliorating one or more symptoms of diseases associated with viral infections.

The compounds and compositions provided herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with viral infections or inappropriate cell proliferation. Such therapeutic agents include, but are not limited to, antiviral agents and antineoplastic agents.

The present invention concerns a composition comprising a compound of the invention as defined above, that is to say of formula (I), but also of any of formulae (I'), (I-1), (I-2), (I'-2), (II), (II'), (III), (III') or (IV), or of any of compounds of formulae (1), (2), (3), (4), (5), (6), (7), (8), (9), (10), (11), (12), (13) or (14), in combination with ganciclovir.

EXAMPLES

Preparation of Compounds of the Invention

Commercially available chemicals were of reagent grade and used as received from Sigma-Aldrich, Alfa-Aesar or Apollo Scientific. The reactions were monitored by thin layer chromatography (TLC) analysis using silica gel plates (Kieselgel 60F254, E. Merck). Column chromatography was performed on Silica Gel 60 M (0.040e0.063 mm, E. Merck). The $^1H$, $^{13}C$ and $^{31}P$ NMR spectra were recorded on a Varian InovaUnity 400 spectrometer (400 MHz) in (d4) methanol (MeOD), $CDCl_3$, $(CD_3)_2CO$, shift values in parts per million relative to $SiMe_4$ as internal reference. High Resolution Mass spectra were performed on a Bruker maXis mass spectrometer by the "Federation de Recherche" ICOA/CBM (FR2708) platform.

I—Preparation of the Synthons Bearing Bases 6-chloro-$N^4$-cyclopropyl-pyrimidine-2,4-diamine
(226)

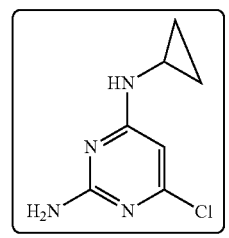

Chemical Formula: $C_7H_9ClN_4$
Molecular Weight: 184.63

Under inert atmosphere, 2-amino-4,6-dichloropyrimidine (2 g, 1 eq., 12.2 mmol) was dissolved in n-butanol (40 mL). To this solution, cyclopropylamine (850 µL, 1 eq., 12.2 mmol) and diisopropylethylamine (2.3 mL, 1.1 eq., 13.4 mmol) were sequentially added. The mixture was then refluxed at 95° C. for 12 h, then all the volatiles were removed under reduced pressure. The resulting crude product was then dissolved in ethyl acetate (80 mL) and water (80 mL). The aqueous phase was then extracted with ethyl acetate (3×80 mL), and the organic phases washed with water (40 mL). In order to extract all trace of product from the aqueous phase, this layer was extracted 5 times with a mixture of chloroform/isopropanol 4:1 (4×100 mL), the combined organic phases washed once with brine (50 mL), dried over MgSO$_4$ and evaporated. The residue was then purified by silica gel column chromatography (DCM/MeOH 95:5), to give the desired product 226 as a white solid. (2.1 g, 93%) $^1$H NMR (400 MHz, MeOD) δ 6.00 (s, 1H, H$^5$), 2.54 (bs, 1H, CH cyclopropyl), 0.77 (dt, J=7.1, 4.8 Hz, 2H, CH$_2$ cyclopropyl), 0.51 (dt, J=4.7, 4.0 Hz, 2H, CH$_2$ cyclopropyl). CAS: 21573-09-1

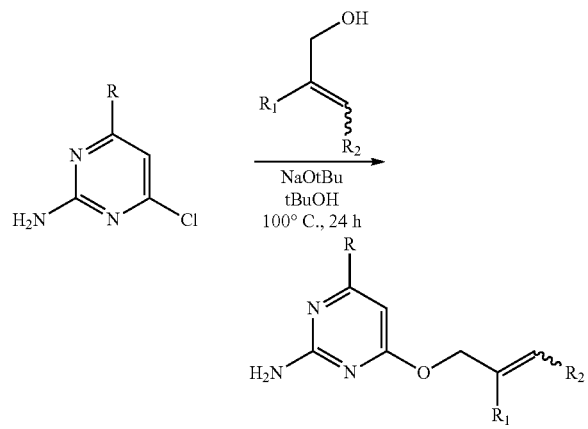

General procedure 1

To a mixture of 6-chloropyrimidine analog (1 eq.) in tBuOH, the corresponding allylic alcohol (3 eq.), followed by NaOtBu (2 eq.) were introduced. After 24 h stirring at 100° C., the mixture was concentrated under reduced pressure. The crude product was purified by flash column chromatography (eluting DCM/MeOH) to give desired to compounds.

6-[(E)-but-2-enoxy]pyrimidine-2,4-diamine (245)

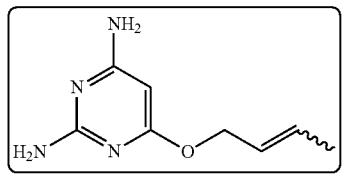

Chemical Formula: C$_8$H$_{12}$N$_4$O
Molecular Weight: 180.21

Following the general procedure 1, to a solution of 2,4-diamino-6-chloropyrimidine (100 mg, 1 eq., 0.69 mmol) in tBuOH (2 mL) was introduced crotyl alcohol, mixture of cis and trans isomers (0.18 mL, 3 eq., 2.08 mmol) and NaOtBu (133 mg, 2 eq., 1.38 mmol). Desired compound 245 was obtained after purification as a colorless oil, as a cis and trans mixture. (125 mg, quantitative yield) $^1$H NMR (400 MHz, (CD$_3$)$_2$CO) δ 5.70 (m, 2H, H$^{2'/3'}$), 5.53 (bs, 2H, NH$_2$), 5.45 (bs, 2H, NH$_2$) 5.15 (s, 1H, H$^5$), 4.56 (m, 2H, CH$_2$—O), 1.66 (m, 3H, CH$_3$). $^{13}$C NMR (101 MHz, (CD$_3$)$_2$CO) δ 171.50 (C$^6$), 167.15 (C$^2$), 164.15 (C$^4$), 129.96 (C$^{2'/3'}$), 127.65 (C$^{2'/3'}$), 77.78 (C$^5$), 66.26 (CH$_2$—O), 17.85 (CH$_3$). HRMS-ESI (m/z) [M+H]$^+$ calcd for C$_8$H$_{13}$N$_4$O 181.1084, found 181.1081.

2-[(2,6-diaminopyrimidin-4-yl)oxymethyl]prop-2-en-1-ol (192)

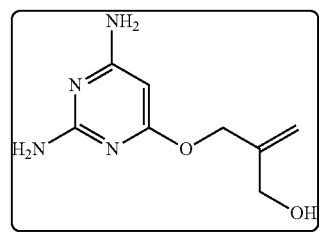

Chemical Formula: C$_8$H$_{12}$N$_4$O$_2$
Molecular Weight: 196.21

Following the general procedure 1, from 2,4-diamino-6-chloropyrimidine (300 mg, 1 eq., 2.08 mmol), 2-methylene-1,3-propenediol (0.5 mL, 3 eq., 6.22 mmol) and NaOtBu (400 mg, 2 eq., 4.15 mmol) in tBuOH (12 mL), compound 192 was obtained as a colorless oil (271 mg, 63%) after purification by flash column chromatography with EtOAc/petroleum ether (9:1) followed by EtOAc and then EtOAc/MeOH (98:2) as eluent. $^1$H NMR (400 MHz, (CD$_3$)$_2$CO) δ 5.60 (bs, 2H, NH$_2$), 5.51 (bs, 2H, NH$_2$), 5.24 (s, 1H, H$^5$), 5.17 (m, 1H, H$^{3'}$), 5.11 (m, 1H, H$^{3'}$), 4.74 (s, 2H, CH$_2$—O), 4.10 (s, 2H, CH$_2$OH). $^{13}$C NMR (101 MHz, (CD$_3$)$_2$CO) δ 171.64 (C$^6$), 167.39 (C$^2$), 164.18 (C$^4$), 147.10 (C$^{2'}$), 111.64 (C$^{3'}$), 77.96 (C$^5$), 66.04 (CH$_2$—O), 63.46 (CH$_2$—O). HRMS-ESI (m/z) [M+H]$^+$ calcd for C$_8$H$_{13}$N$_4$O$_2$ 197.1033, found 197.1029.

2-[[2-amino-6-(cyclopropylamino)pyrimidin-4-yl]oxymethyl]prop-2-en-1-ol (228)

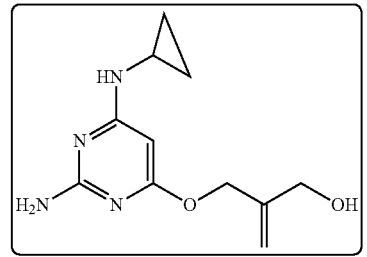

Chemical Formula: C$_{11}$H$_{16}$N$_4$O$_2$
Molecular Weight: 236.28

Following the general procedure 1 from 226 (300 mg, 1 eq., 1.65 mmol), 2-methylene-1,3-propenediol (398 µL, 3 eq., 4.87 mmol) and NaOtBu (317 mg, 2 eq., 3.30 mmol) in tBuOH (3.2 mL), compound 228 was obtained as a white solid (173 mg, 45%) after purification by flash column chromatography, eluting DCM/MeOH 95:5. $^1$H NMR (400

MHz, (CD$_3$)$_2$CO) δ 6.03 (bs, 1H, NH cyclopropyl), 5.51 (bs, 2H, NH$_2$), 5.41 (s, 1H, H$^5$), 5.18 (s, 1H, CH=C), 5.13 (s, 1H, CH=C), 4.77 (s, 2H, H$^1$), 4.12 (s, 2H, H$^3$), 2.91 (s, 1H, OH), 2.47 (m, 1H, CH cyclopropyl), 0.71 (dt, J=6.8, 4.8 Hz, 2H, CH$_2$ cyclopropyl), 0.48 (dt, J=6.8, 4.0 Hz, 2H, CH$_2$ cyclopropyl). $^{13}$C NMR (101 MHz, (CD$_3$)$_2$CO) δ 170.70 (C$^6$), 166.84 (C$^2$), 162.84 (C$^4$), 146.16 (C$^{2'}$), 110.84 (CH$_2$=C), 76.00 (C$^5$), 65.21 (C$^{1'}$), 62.56 (C$^{3'}$), 23.12 (CH cyclopropyl), 6.58 (CH$_2$ cyclopropyl). HRMS-ESI (m/z) [M+H]$^+$ calcd for C$_{11}$H$_{17}$N$_4$O$_2$: 237.1352, found: 237.1345.

2-[(2-amino-6-methoxy-pyrimidin-4-yl)oxymethyl]prop-2-en-1-ol (229)

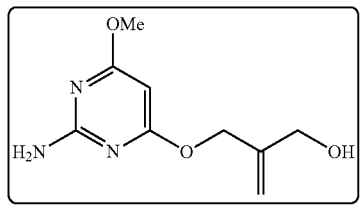

Chemical Formula: C$_9$H$_{13}$N$_3$O$_3$
Molecular Weight: 211.22

Following the general procedure 1, 2-amino-4-methoxy-6-chloropyrimidine (300 mg, 1 eq., 1.88 mmol), 2-methylene-1,3-propenediol (460 µL, 3 eq., 5.64 mmol) and NaOtBu (361 mg, 2 eq., 3.76 mmol) in tBuOH (5 mL), compound 229 was obtained as a white solid after purification by flash column chromatography with DCM/MeOH 92:8. (202 mg, 51%). $^1$H NMR (400 MHz, (CD$_3$)$_2$CO) δ 5.93 (bs, 2H, NH$_2$), 5.39 (s, 1H, H$^5$), 5.21 (s, 1H, CH$_2$=C), 5.15 (s, 1H, CH$_2$=C), 4.80 (s, 2H, C$^1$), 4.14 (d, J=5.8 Hz, 2H, C$^3$), 3.96 (t, J=5.8 Hz, 1H, OH), 3.80 (s, 3H, CH$_3$). $^{13}$C NMR (101 MHz, (CD$_3$)$_2$CO) δ 172.31 (C$^4$), 171.61 (C$^6$), 163.00 (C$^2$), 145.76 (C$^{2'}$), 110.87 (CH$_2$=C), 79.05 (C$^5$), 65.71 (C$^{1'}$), 62.53 (C$^{3'}$), 52.64 (CH$_3$). HRMS-ESI (m/z) [M+H]$^+$ calcd for C$_9$H$_{14}$N$_3$O$_3$: 212.1036, found: 212.1034.

6-(2-methylallyloxy)pyrimidine-2,4-diamine (284)

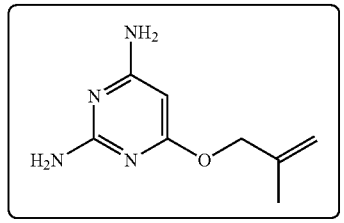

Chemical Formula: C$_8$H$_{12}$N$_4$O
Molecular Weight: 180.21

Following the general procedure 1 from 2,4-diamino-6-chloropyrimidine (250 mg, 1 eq., 1.73 mmol), 2-methyl-2-propen-1-ol (0.44 mL, 3 eq., 5.19 mmol) and NaOtBu (332 mg, 2 eq., 3.46 mmol) in tBuOH (5 mL), compound 284 was obtained as a colorless oil (256 mg, 82%) after purification by flash column chromatography with EtOAc/petroleum ether (9:1) then EtOAc as eluent. $^1$H NMR (400 MHz, (CD$_3$)$_2$CO) δ 5.69 (bs, 2H, NH$_2$), 5.64 (bs, 2H, NH$_2$), 5.25 (s, 1H, H$^5$), 4.98 (s, 1H, H$^{3'}$), 4.86 (s, 1H, H$^{3'}$), 4.61 (s, 2H, CH$_2$—O), 1.75 (s, 3H, CH$_3$). $^{13}$C NMR (101 MHz, (CD$_3$)$_2$CO) δ 171.57 (C$^6$), 167.32 (C$^2$), 164.20 (C$^4$), 142.48 (C$^{2'}$), 111.90 (C$^{3'}$), 77.79 (C$^5$), 68.69 (CH$_2$—O), 19.64 (CH$_3$). HRMS-ESI (m/z) [M+H]$^+$ calcd for C$_8$H$_{13}$N$_4$O 181.1084, found 181.1080.

6-(2-methylallyloxy)triazine-2,4-diamine (60)

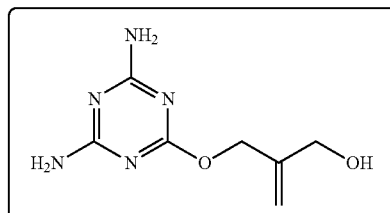

Chemical Formula: C$_7$H$_{11}$N$_5$O$_2$
Molecular Weight: 197.20

Following the general procedure 1, from 2,4-diamino-2-chloro-1,3,5-triazine (1 g, 1 eq., 6.87 mmol), 2-methylene-1,3-propenediol (1.68 mL, 3 eq., 20.6 mmol) and NaOtBu (1.3 g, 2 eq., 13.74 mmol) in tBuOH (40 mL), compound 60 was obtained as a white solid (451 mg, 34%) after purification by flash column chromatography with CH$_2$Cl$_2$/MeOH (9:1) followed by EtOAc and then EtOAc/MeOH (98:2) as eluent. $^1$H NMR (400 MHz, (CD$_3$)$_2$CO) δ 6.02 (bs, 4H, NH$_2$), 5.18 (d, J=2.5 Hz 1H, H$^3$), 5.13 (d, J=2.5 Hz 1H, H$^3$), 4.76 (s, 2H, CH$_2$—O), 4.12 (d, J=4.0 Hz, 2H, CH$_2$OH), 3.95 (t, J=4.0 Hz, 1H, OH), $^{13}$C NMR (101 MHz, (CD$_3$)$_2$CO) δ 171.34 (C$^6$), 169.17 (C$^2$), 145.75 (C$^{2'}$), 110.76 (C$^{3'}$), 77.96 (C$^5$), 66.01 (CH$_2$—O), 62.56 (CH$_2$—O). HRMS-ESI (m/z) [M+H]$^+$ calcd for C$_8$H$_{13}$N$_4$O$_2$ 197.1033, found 197.1029.

Acetylation of Hydroxyl Group

2-[(2,6-diaminopyrimidin-4-yl)oxymethyl]allyl acetate (196)

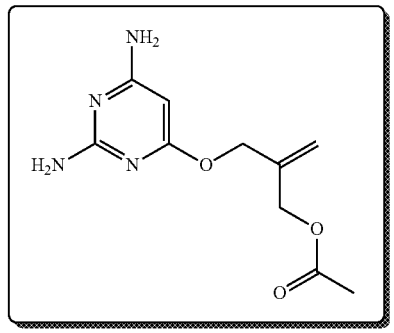

Chemical Formula: C$_{10}$H$_{14}$N$_4$O$_3$
Molecular Weight: 238.25

Compound 192 (2 g, 1 eq., 10 mmol), vinyl acetate (2.63 g, 3 eq., 30 mmol) and CAL-B (1 g) were added in anhydrous acetonitrile (200 mL) was heated at 35° C. during 10 h. the mixture was filtrated and concentrated. The crude product was solubilized in EtOAc, washed twice with water, dried with MgSO$_4$, filtrated and concentrated under vacuum. Purification by flash column chromatography with EtOAc followed by EtOAc/MeOH (95:5) as eluent gave the mono-acetylated compound 196 (1.9 g, 80%) as a colorless oil. $^1$H NMR (400 MHz, (CD$_3$)$_2$CO) δ 5.73 (bs, 2H, NH$_2$), 5.66 (bs, 2H, NH$_2$), 5.28 (m, 1H, H$^3$'), 5.27 (s, 1H, H$^5$), 5.23 (m, 1H, H$^3$'), 4.76 (s, 2H, CH$_2$—O), 4.64 (s, 2H, CH$_2$—OAc), 2.05 (s, 3H, CH$_3$). $^{13}$C NMR (101 MHz, (CD$_3$)$_2$CO) δ 171.34 (C$^6$), 170.66 (C=O), 167.25 (C$^4$), 164.06 (C$^2$), 141.67 (C$^2$'), 114.95 (C$^3$'), 77.87 (C$^5$), 65.73 (CH$_2$—O), 64.96 (CH$_2$—OAc), 20.69 (CH$_3$). HRMS-ESI (m/z) [M+H]$^+$ calcd for C$_{10}$H$_{15}$N$_4$O$_3$ 239.1139, found 239.1137.

2-[[2-amino-6-(cyclopropylamino)pyrimidin-4-yl]oxymethyl]allyl acetate (230)

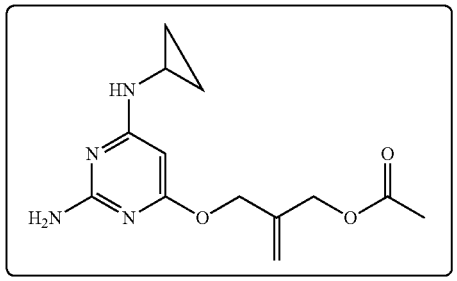

Chemical Formula: C$_{13}$H$_{18}$N$_4$O$_3$
Molecular Weight: 278.31

Acetic anhydride (596 μL, 3 eq., 6.30 mmol) and sodium acetate (348 mg, 2 eq., 4.24 mmol) were sequentially added to a solution of compound 228 (500 mg, 1 eq., 2.12 mmol) in AcN (16 mL). This vial was sealed and heated under microwave irradiation for 30 min. at 80° C. The crude product was dissolved in EtOAc (40 mL), extracted twice with water (2×20 mL), once with brine (20 mL), dried over MgSO$_4$ and the volatiles removed under vacuo. The residue was finally purified by column chromatography (DCM/MeOH 99:1) in order to yield the desired product 230 as a white solid. (180 mg, 30%) $^1$H NMR (400 MHz, (CD$_3$)$_2$CO) δ 6.13 (bs, 1H, NH cyclopropyl), 5.60 (bs, 2H, NH$_2$), 5.43 (s, 1H, H$^5$), 5.30 (s, 1H, CH=C), 5.24 (s, 1H, CH=C), 4.78 (s, 2H, H$^1$), 4.65 (m, 2H, H$^2$), 2.48 (s, 1H, CH cyclopropyl), 2.05 (s, 3H, CH$_3$Ac), 0.72 (dt, J=6.8, 4.6 Hz, 2H, CH$_2$ cyclopropyl), 0.49 (dt, J=6.8, 4.3 Hz, 2H, CH$_2$ cyclopropyl). $^{13}$C NMR (101 MHz, (CD$_3$)$_2$CO) δ 170.48 (C$^6$), 169.80 (C=O Ac), 166.85 (C$^2$), 162.85 (C$^4$), 146.16 (C$^2$'), 114.19 (CH$_2$=C), 75.99 (C$^5$), 64.96 (C$^1$'), 64.13 (C$^3$'), 23.13 (CH$_3$Ac), 19.86 (CH cyclopropyl), 6.61 (CH$_2$ cyclopropyl). HRMS-ESI (m/z) [M+H]$^+$ calcd for C$_{13}$H$_{19}$N$_4$O$_3$: 279.1457, found: 279.1453.

2-[(2-amino-6-chloro-pyrimidin-4-yl)oxymethyl]allyl acetate (233)

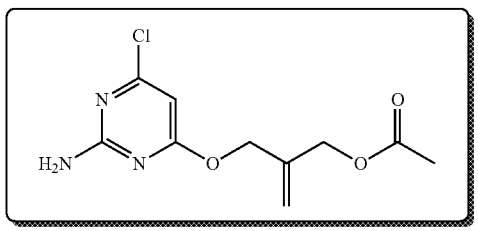

Chemical Formula: C$_{10}$H$_{12}$ClN$_3$O$_3$
Molecular Weight: 257.67

To a solution of 2-methylene-1,3-propanediol (3 g, 1 eq., 18.3 mmol) in dioxane (72 mL), sodium hydride (60% in oil, 732 mg, 1 eq., 18.3 mmol) was slowly added, and the solution was stirred 30 min. at 70° C. 2-amino-4,6-dichloropyrimidine was then added and the mixture was refluxed 3 h at 110° C. After evaporation of all volatiles, the residue was loaded onto a silica gel column and purified using DCM/MeOH (99:1) as eluent, affording 4 g of a white powder. The product, contaminated with dipyrimidine moiety side-product, was then directly engaged in the following step, in order to separate these compounds. 8 vials of 10-20 mL were filled each with 500 mg of product and dissolved in AcN (16 mL). To these mixtures, acetic anhydride (439 μL, 2 eq., 4.64 mmol) and sodium acetate (571 mg, 3 eq., 6.96 mmol) were added and each vial was afterwards submitted to microwave irradiation for 30 min. at 80° C. Over these collected fractions, 100 mL of ethyl acetate was added, extracted twice with water (40 mL), once with brine (40 mL), dried over MgSO$_4$ and evaporated under reduced pressure. Pure compound 233 was then obtained after silica gel chromatography, eluting dichloromethane to afford desired product as a white solid (2.12 g, 45%). $^1$H NMR (400 MHz, (CD$_3$)$_2$CO) δ 6.35 (bs, 2H, NH$_2$), 6.11 (s, 1H, H$^5$), 5.33 (s, 1H, CH$_2$=C), 5.29 (s, 1H, CH$_2$=C), 4.85 (s, 2H, H$^1$'), 4.66 (s, 2H, H$^3$'), 2.05 (s, 3H, Ac). $^{13}$C NMR (101 MHz, (CD$_3$)$_2$CO) δ 170.65 (C$^6$), 169.67 (C=O Ac), 163.12 (C$^4$), 160.73 (C$^2$), 139.83 (C$^2$'), 115.26 (C$^3$'), 95.20 (C$^5$), 66.04 (CH$_2$—O), 63.91 (CH$_2$—OAc), 19.76 (CH$_3$). HRMS-ESI (m/z) [M+H]$^+$ calcd for C$_{10}$H$_{13}$ClN$_3$O$_3$: 258.0646, found: 258.0640.

2-[(triazine-2,4-diamine)oxymethyl]allyl acetate (61)

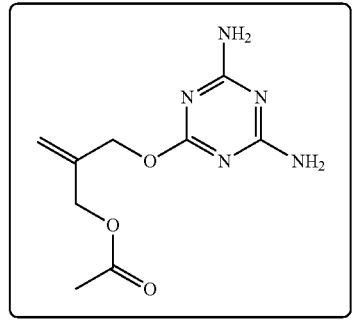

Chemical Formula: C$_9$H$_{13}$N$_5$O$_3$
Molecular Weight: 239.24

To a mixture of compound 60 (391 mg, 1 eq., 1.98 mmol) in CH$_3$CN, vinyle acetate (0.55 mL, 3 eq., 5.95 mmol) and *Candida antarctica* lipase B (CAL-B, 2.56 eq., 1.00 g) were added. The mixture was stirred for 4 h at 35° C., then all the solids were filtered off and washed with acetone. All the volatiles were removed by rotary evaporation. The residue was purified on a silica gel column eluting DCM/MeOH 97:3, allowing the obtention of compound 61 as white solid (412 mg, 87%). $^1$H NMR (250 MHz, Chloroform-d) δ 5.36 (s, 1H, H$^3$'), 5.28 (s, 1H$^3$'), 5.00 (s, 4H, NH$_2$), 4.81 (s, 2H, CH$_2$-ODAPY), 4.67 (s, 2H, CH$_2$—OAc), 2.09 (s, 3H, CH$_3$). $^{13}$C NMR (101 MHz, Chloroform-d) δ 171.52 (C$^6$), 171.11 (C=O Ac), 170.47 (C$^4$), 166.63 (C$^2$), 137.84 (C$^2$'), 117.80 (C$^3$'), 68.29 (CH$_2$—ODAPY), 64.65 (CH$_2$—OAc), 20.82 (CH$_3$). HRMS-ESI (m/z) [M+H]$^+$ calcd for C$_9$H$_{13}$N$_5$O$_3$ 240.1088, found 240.1091.

General procedure 2

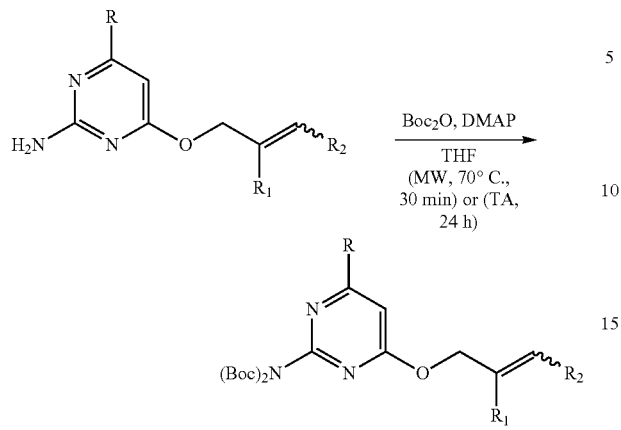

Di-tert-butyl dicarbonate (6 eq.) and 4-(Dimethylamino) pyridine (0.35 eq.) were added to a solution of compound (1 eq.) in THF in a closed microwave reaction vessel. After MW-irradiation for 30 min at 70° C. (or at room temperature during 24 h in the case of large scale), the reaction mixture was concentrated under vacuum and purified by flash column chromatography using petroleum ether/EtOAc as eluent affording expected compounds as colorless oils.

Tert-butyl-N-[2-[bis(tert-butoxycarbonyl)amino]-6-[-but-2-enoxy]pyrimidin-4-yl]-N-tert-butoxycarbonyl-carbamate (246)

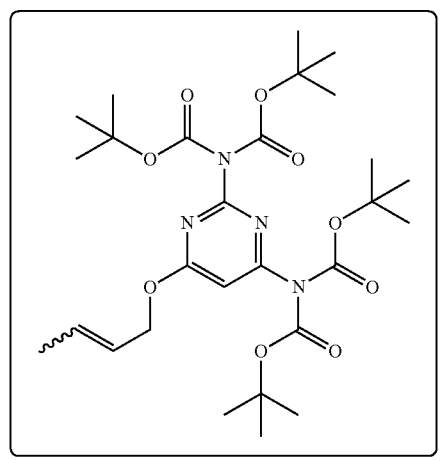

Chemical Formula: $C_{28}H_{44}N_4O_9$
Molecular Weight: 580.68

Di-tert-butyl dicarbonate (2.9 g, 6 eq., 13.32 mmol) and 4-(Dimethylamino)pyridine (95 mg, 0.35 eq., 0.78 mmol) were added to a solution of compound 245 (400 mg, 1 eq., 2.22 mmol) in THF (10 mL), following conditions of general procedure 2. The expecting compound 246 (1.19 g, 92%) was obtained as a colorless oil after purification by flash column chromatography. $^1$H NMR (400 MHz, CDCl$_3$) δ 6.85 (s, 1H, H$^5$), 5.81 (m, 1H, H$^{3'}$), 5.67 (m, 1H, H$^{2'}$), 4.73 (d, J=6.3 Hz, 2H, CH$_2$—O), 1.69 (dd, J=6.4, 1.5 Hz, 3H, CH$_3$), 1.47 (s, 18H, CH$_3$—Boc), 1.40 (s, 18H, CH$_3$—Boc). $^{13}$C NMR (101 MHz, CDCl$_3$) δ 171.51 (C$^6$), 159.87 (C$^4$), 156.5 (C$^2$), 150.47 (C=O $^{Boc}$), 150.02 (C=O $^{Boc}$), 131.55 (C$^{2'/3'}$), 125.19 (C$^{2'/3'}$), 96.63 (C$^5$), 84.07 (C$^{quat\ Boc}$), 83.03 (C$^{quat\ Boc}$), 67.78 (CH$_2$—O), 27.87 (CH$_3$ Boc), 27.77 (CH$_3$ Boc), 17.84 (CH$_3$). HRMS-ESI (m/z) [M+H]$^+$ calcd for $C_{28}H_{45}N_4O_9$ 581.3181, found 581.3179.

Tert-butyl N-[2-[bis(tert-butoxycarbonyl)amino]-6-(2-methylallyloxy)pyrimidin-4-yl]-N-tert-butoxycarbonyl-carbamate (285)

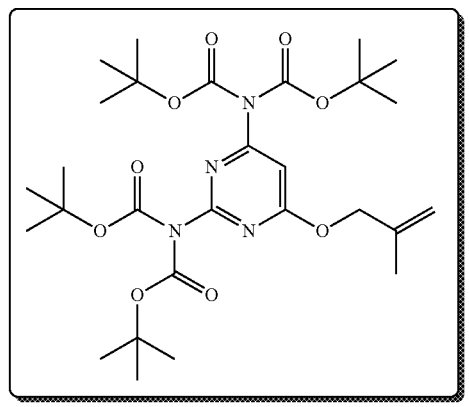

Chemical Formula: $C_{28}H_{44}N_4O_9$
Molecular Weight: 580.68

General procedure 2 was followed on compound 284 (200 mg, 1 eq., 1.11 mmol), di-tert-butyl dicarbonate (1.45 g, 6 eq., 6.66 mmol) and 4-(dimethylamino)pyridine (47 mg, 0.35 eq., 0.39 mmol) in THF (3.5 mL) to give Boc-protected compound 285 (563 mg, 87%) as a colorless oil. $^1$H NMR (400 MHz, CDCl$_3$) δ 6.93 (s, 1H, H$^5$), 5.00 (s, 1H, H$^{3'}$), 4.91 (s, 1H, H$^{3'}$), 4.73 (s, 2H, CH$_2$—O), 1.76 (s, 3H, CH$_3$), 1.48 (s, 18H, CH$_3$ Boc), 1.40 (s, 18H, CH$_3$ Boc). $^{13}$C NMR (101 MHz, CDCl$_3$) δ 171.58 (C$^6$), 159.94 (C$^4$), 156.52 (C$^2$), 150.45 (C=O $^{Boc}$), 150.02 (C=O $^{Boc}$), 139.98 (C$^{2'}$), 113.00 (C$^{3'}$), 96.23 (C$^5$), 84.15 (C$^{quat}$), 83.06 (C$^{quat}$), 70.15 (CH$_2$—O), 27.87 (CH$_3$ Boc), 27.79 (CH$_3$ Boc), 19.52 (CH$_3$). HRMS-ESI (m/z) [M+H]$^+$ calcd for $C_{28}H_{45}N_4O_9$ 581.3181, found 581.3185.

2-[[2,6-bis[bis(tert-butoxycarbonyl)amino]pyrimidin-4-yl]oxymethyl]allyl acetate (200)

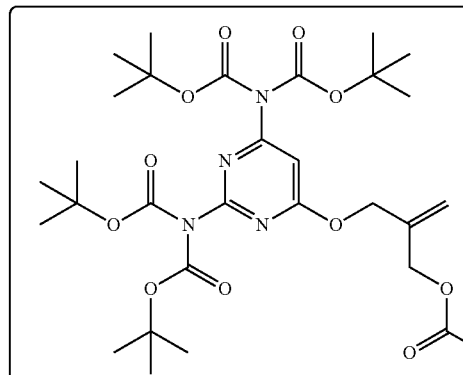

Chemical Formula: $C_{30}H_{46}N_4O_{11}$
Molecular Weight: 638.72

General procedure 2 was applied with compound 196 (118 mg, 1 eq., 0.50 mmol), di-tert-butyl dicarbonate (649 mg, 6 eq., 2.97 mmol) and 4-(dimethylamino)pyridine (21 mg, 0.35 eq., 0.17 mmol) in THF (3 mL) to give tetra-Boc-protected compound 200 (265 mg, 84%) as a colorless oil. $^1$H NMR (400 MHz, CDCl$_3$) δ 6.95 (s, 1H, H$^5$), 5.31 (s, 1H, H$^{3'}$), 5.27 (s, 1H, H$^{3'}$), 4.84 (s, 2H, CH$_2$—O), 4.62 (s, 2H, CH$_2$—OAc), 2.04 (s, 3H, CH$_3$), 1.48 (s, 18H, CH$_3$ Boc), 1.41 (s, 18H, CH$_3$ Boc). $^{13}$C NMR (101 MHz, CDCl$_3$) δ 171.24 (C$^6$), 170.57 (C=O $^{Ac}$), 159.97 (C$^4$), 156.45 (C$^2$), 150.44 (C=O $^{Boc}$), 149.96 (C=O $^{Boc}$), 138.68 (C$^{2'}$), 116.75 (C$^{3'}$), 96.03 (C$^5$), 84.27 (C$^{quat\ Boc}$) 83.17 (C$^{quat\ Boc}$), 67.00 (CH$_2$—O), 64.67 (CH$_2$—OAc), 27.88 (CH$_3$ Boc), 27.78 (CH$_3$ Boc), 20.88 (CH$_3$). HRMS-ESI (m/z) [M+H]$^+$ calcd for C$_{30}$H$_{47}$N$_4$O$_{11}$ 639.3236, found 639.3231.

2-[[2-[bis(tert-butoxycarbonyl)amino]-6-[tert-butoxycarbonyl(cyclopropyl)amino]pyrimidin-4-yl]oxymethyl]allyl acetate (234)

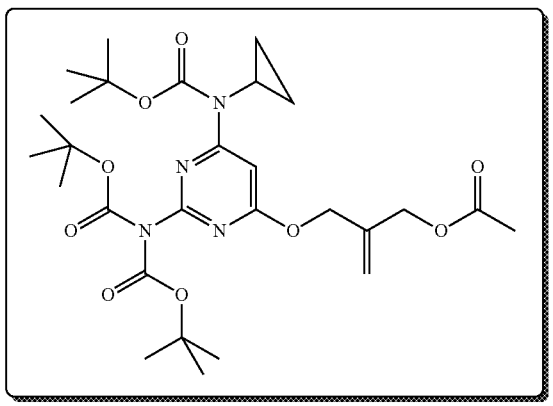

Chemical Formula: C$_{28}$H$_{42}$N$_4$O$_9$
Molecular Weight: 578.66

Following general procedure 2, in a 2-5 mL microwave vial, a solution of compound 230 (56 mg, 1 eq., 0.20 mmol) was dissolved into THF (2 mL). To this mixture dimethylaminopyridine (9 mg, 0.35 eq., 0.07 mmol) and di-tert-butyl dicarbonate (264 mg, 6 eq., 1.21 mmol) were added, and the reaction was stirred under microwave irradiation at 70° C. for 30 minutes. After evaporation of all volatiles, pure compound 234 was isolated after purification on a silica gel column chromatography, eluting Petroleum ether/Ethyl acetate 93:7. (93 mg, 80%) HRMS-ESI (m/z) [M+H]$^+$ calcd for C$_{28}$H$_{42}$N$_4$O$_9$: 579.3030, found: 579.3026.

2-[[2-[bis(tert-butoxycarbonyl)amino]-6-methoxy-pyrimidin-4-yl]oxymethyl]allyl acetate (235)

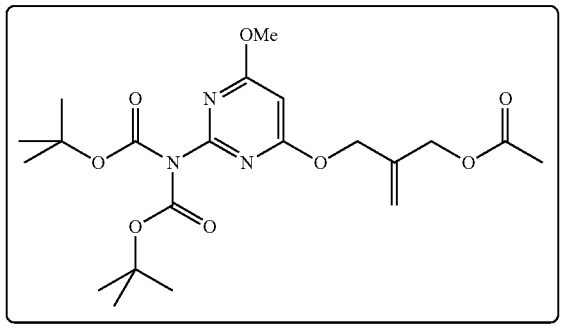

Chemical Formula: C$_{21}$H$_{31}$N$_3$O$_8$
Molecular Weight: 453.49

Compound 231 (590 mg, 1 eq., 2.79 mmol), acetic anhydride (0.53 mL, 3 eq., 5.59 mmol) and NaOAc (687 mg, 2 eq., 8.37 mmol) were suspended in anhydrous acetonitrile (18 mL) in a microwave sealed tube. The mixture was irradiated for 30 min at 80° C. The crude product was extracted with EtOAc, washed twice with water (2 mL), dried over MgSO$_4$, filtrated and concentrated under vacuum. After purification on silica (eluting DCM/MeOH 99:1), the obtained product was directly engaged in the next step. Following general procedure 2, in a microwave vial, the mono-acetylated product (350 mg, 1 eq., 1.38 mmol) was dissolved in THF (10 mL). To this mixture dimethylaminopyridine (59 mg, 0.35 eq., 0.48 mmol) and di-tert-butyl dicarbonate (1.81 g, 6 eq., 8.29 mmol) were added, and the reaction was stirred under microwave irradiation at 70° C. for 30 minutes. After evaporation of all volatiles, pure compound 235 was isolated after purification on a silica gel column chromatography, eluting Petroleum ether/Ethyl acetate 93:7. (532 mg, 42% over 2 steps) $^1$H NMR (400 MHz, CDCl$_3$) δ 5.95 (s, 1H, H$^5$), 5.33 (s, 1H, CH$_2$=C), 5.29 (s, 1H, CH$_2$=C), 4.85 (s, 2H, C$^{1'}$), 4.65 (s, 2H, C$^{3'}$), 3.92 (s, 3H, CH$_3$), 2.08 (s, 3H, CH$_3$Ac), 1.47 (s, 3H, CH$_3$Boc). $^{13}$C NMR (101 MHz, CDCl$_3$) δ 172.20 (C$^4$), 171.20 (C$^6$), 170.57 (C=O Ac), 156.66 (C$^2$), 150.62 (C=O Boc), 138.84 (C$^2$), 116.66 (CH$_2$=C), 88.42 (C$^5$), 66.83 (C$^1$), 64.65 (C$^3$), 52.64 (CH$_3$OMe), 27.86 (CH$_3$ Boc), 20.84 (CH$_3$Ac). HRMS-ESI (m/z) [M+H]$^+$ calcd for C$_{21}$H$_{32}$N$_3$O$_8$: 454.2190, found: 454.2183.

2-[[2-[bis(tert-butoxycarbonyl)amino]-6-chloro-pyrimidin-4-yl]oxymethyl]allyl acetate (236)

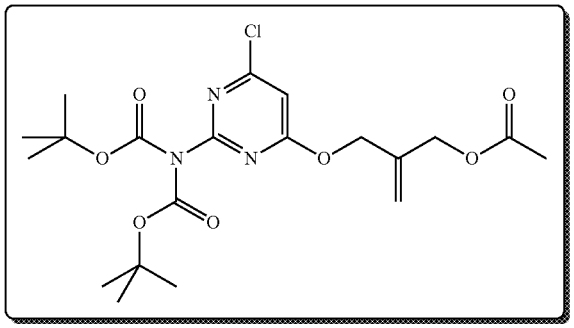

Chemical Formula: C$_{20}$H$_{28}$ClN$_3$O$_7$
Molecular Weight: 457.91

Following general procedure 2, in a microwave vial, a solution of compound 233 (389 mg, 1 eq., 1.51 mmol) was dissolved in THF (14 mL). To this mixture dimethylaminopyridine (65 mg, 0.35 eq., 0.52 mmol) and di-tert-butyl dicarbonate (1.98 g, 6 eq., 9.08 mmol) were added, and the reaction was stirred under microwave irradiation at 70° C. for 30 minutes. After evaporation of all volatiles, pure compound 236 was isolated after purification on a silica gel column chromatography, eluting Petroleum ether/Ethyl acetate 93:7. (447 mg, 65%) $^1$H NMR (400 MHz, CDCl$_3$) δ 6.67 (s, 1H, H$^5$), 5.34 (d, J=5.6 Hz, 1H, CH=C), 4.89 (s, 2H, H$^1$), 4.65 (s, 2H, H$^{3'}$), 2.08 (s, 3H, CH$_3$Ac), 1.48 (s, 18H, CH$_3$ Boc). $^{13}$C NMR (101 MHz, CDCl$_3$) δ 170.73 (C$^6$), 170.49 (C=O Ac), 161.24 (C$^4$), 157.29 (C$^2$), 150.10 (C=O Boc), 138.15 (C=O Boc), 117.51 (CH=C), 105.22 (C$^5$), 83.74 (C Boc), 67.48 (C$^1$), 64.48 (C$^3$), 27.83 (CH$_3$ Boc), 20.81 (CH$_3$Ac). HRMS-ESI (m/z) [M+H]$^+$ calcd for C$_{20}$H$_{29}$ClN$_3$O$_7$: 458.1694, found: 458.1691.

2-[[2,6-bis[bis(tert-butoxycarbonyl)amino]triazine-2,4-diamine]oxymethyl]allyl tert-butyl carbonate (62)

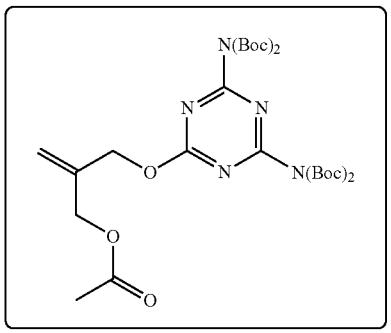

Chemical Formula: $C_{29}H_{45}N_5O_{11}$
Molecular Weight: 639.70

Di-tert-butyl dicarbonate (2.26 g, 6 eq., 10.33 mmol) and 4-(Dimethylamino)pyridine (74 mg, 0.35 eq., 0.60 mmol) were added to a solution of compound 61 (412 mg, 1 eq., 1.72) in THF anhydrous (10 mL). The reaction mixture was stirred for 24 h at room temperature. After evaporation of all volatiles, the crude product was purified by flash column chromatography using petroleum ether/EtOAc (9:1) as eluent affording expected tetra-Boc-protected compounds 62 (828 mg, 75%) as colorless oils.

$^1$H NMR (400 MHz, Chloroform-d) δ 5.39 (s, 1H, H$^3$'), 5.33 (s, 1H, H$^3$'), 4.91 (s, 2H, CH$_2$—ODAPY), 4.66 (s, 2H, CH$_2$—OAc), 2.04 (s, 3H, CH$_3$), 1.51 (s, 36H, Boc). $^{13}$C NMR (101 MHz, Chloroform-d) δ 171.52 (C$^6$), 171.11 (C=O $^{Ac}$), 170.47 (C$^4$), 166.63 (C$^2$), 149.20 (C=O $^{Boc}$), 137.84 (C$^{2'}$), 117.80 (C$^{3'}$), 84.37 (C$^{quat\ Boc}$) 68.29 (CH$_2$—ODAPY), 64.65 (CH$_2$—OAc), 27.67 (CH$_3$, Boc), 20.82 (CH$_3$).

II—Preparation of Phosphonate Synthons
1—Synthesis of Vinyl Phosphonate Synthons Bearing Biolabile Groups

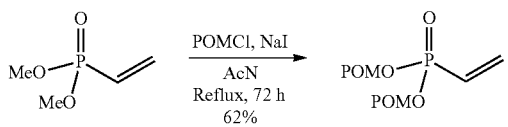

[2,2-dimethylpropanoyloxymethoxy(vinyl)phosphoryl]oxymethyl 2,2-dimethylpropanoate (248)

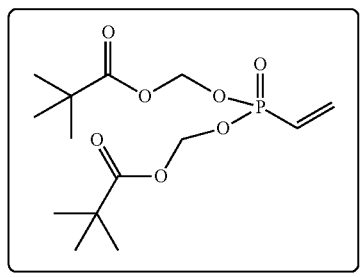

Chemical Formula: $C_{14}H_{25}O_7P$
Molecular Weight: 336.32

Dimethylvinylphosphonate (1 g, 1 eq, 7.35 mmol), sodium iodide (2.20 g, 2 eq., 14.7 mmol) and chloromethylpivalate (2.6 Ml, 2.5 eq., 18.4 mmol) were dissolved in anhydrous acetonitrile (7 Ml), and refluxed for 3 days. The crude product was diluted with Et$_2$O (50 Ml), washed with water (10 Ml), with an aqueous solution of Na$_2$S$_2$O$_3$ (10 Ml), dried over MgSO$_4$, filtrated and concentrated under vacuum. Further purification of the product on silica column using PE/EtOAc 8:2 to 7:3 as eluent allowed the production of 248 (1.47 g, 62%) as a colorless oil. $^1$H NMR (400 MHz, CDCl$_3$) δ 6.21 (m, 3H, CH$_2$=CH), 5.67 (m, 4H, O—CH$_2$—O), 1.21 (5, 18H, POM). CAS: 1258789-61-5

2—Synthesis of Allyl Phosphonate Synthons Bearing Biolabile Groups

Dimethyl Allylphosphonate

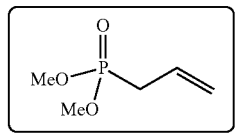

Chemical Formula: $C_5H_{11}O_3P$
Molecular Weight: 150.11

Under inert atmosphere, allyl bromide (51 mL, 1.25 eq., 0.57 mol) was dissolved in THF (400 mL). To this mixture potassium carbonate (94 g, 1.5 eq., 0.68 mol), tert-butylammonium bromide (2.9 g, 2 mol %, 9.1 mmol) and finally dimethylphosphite (41.2 mL, 1 eq., 0.45 mol) were added. The resulting solution was stirred for 36 hours at room temperature, followed by the filtration of all solids present in the flask. The filtrate was then evaporated under reduced pressure, and the crude product was then distilled at 130° C. under 40 mm/Hg. After collection of the different fractions, the clean product was obtained as a colorless liquid. (53 g, 75%) $^1$H NMR (250 MHz, CDCl$_3$) δ 5.80 (m, 1H, CH=CH$_2$), 5.23 (m, 2H, CH$_2$=CH), 3.77 (s, 3H, OMe), 3.72 (s, 3H, OMe), 2.62 (ddt, J=22.0, 7.4, 1.3 Hz, 2H, CH$_2$—P). CAS: 757-54-0 bis(POM) allylphosphonate (83)

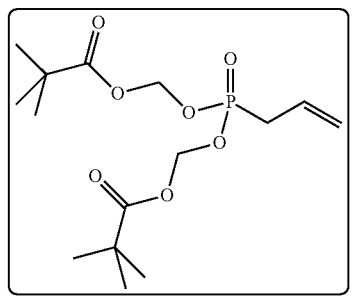

Chemical Formula: $C_{15}H_{27}O_7P$
Molecular Weight: 350.35

Under inert atmosphere, dimethyl allylphosphonate (4.78 mL, 1 eq, 33.31 mmol), sodium iodide (9.99 g, 2 eq., 66.6 mmol) and chloromethyl pivalate (12.1 mL, 2.5 eq., 83.28 mmol) were dissolved in anhydrous acetonitrile (40 mL).

The solution was then refluxed at 110° C. for 3 days. The crude product was diluted with Et$_2$O (150 mL), washed with water (30 mL), with an aqueous solution of Na$_2$S$_2$O$_3$ (30 mL), dried over MgSO$_4$, filtrated and concentrated under vacuum. Further purification of the product on silica column using PE/EtOAc 8:2 to 7:3 as eluent allowed the obtention of 83 (8.38 g, 72%) as a colorless oil. $^1$H NMR (400 MHz, CDCl$_3$) δ 5.67 (m, 5H, O—CH$_2$—O, CH═CH$_2$), 5.21 (m, 2H, CH$_2$═CH), 2.67 (ddt, J=22.7, 7.4, 1.2 Hz, 2H, CH$_2$—P), 1.20 (s, 18H, CH$_3$). CAS: 1258789-63-7 bis-POC-allylphosphonate (205)

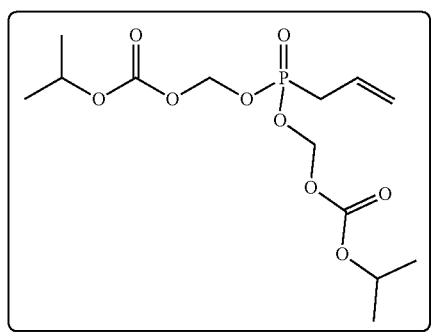

Chemical Formula: C$_{13}$H$_{23}$O$_9$P
Molecular Weight: 354.29

To an acetonitrile (11.5 mL) solution of dimethyl allylphosphonate (1.7 g, 1 eq., 11.3 mmol), anhydrous sodium iodide (3.4 g, 2 eq., 22.6 mmol) and chloromethylisopropylcarbonate (4.25 g, 2.5 eq., 28.3 mmol) were added. This solution was stirred at reflux for 72 h under N$_2$ atmosphere. After cooling, the mixture was diluted with 110 mL of diethyl ether, washed by 20 mL of water and aqueous solution of Na$_2$S$_2$O$_3$ (20 mL). The organic layer was dried over magnesium sulfate, evaporated and purified by silica gel column chromatography (EtOAc/hexanes, 1/4) to give 2.76 g (73%) of pure bis(POC) allylphosphonate 205 as a colorless oil $^1$H NMR (400 MHz, CDCl$_3$) δ 5.76 (m, 1H, CH═CH$_2$), 5.68 (dd, J=11.6, 5.4 Hz, 2H, O—CH$_2$—O), 5.65 (dd, J=11.6, 5.4 Hz, 2H, O—CH$_2$—O), 5.26 (m, 2H, CH$_2$═CH), 4.94 (m, 2H, CH-0), 2.74 (ddt, J=22.8, 7.4, 1.1 Hz, 2H, CH$_2$—P), 1.33 (d, J=6.3 Hz, 12H, CH$_3$ POC). HRMS-ESI (m/z) [M+Na]$^+$ calcd for C$_{13}$H$_{23}$NaO$_9$P: 377.0977, found: 377.0990. CAS: 1258789-64-8.

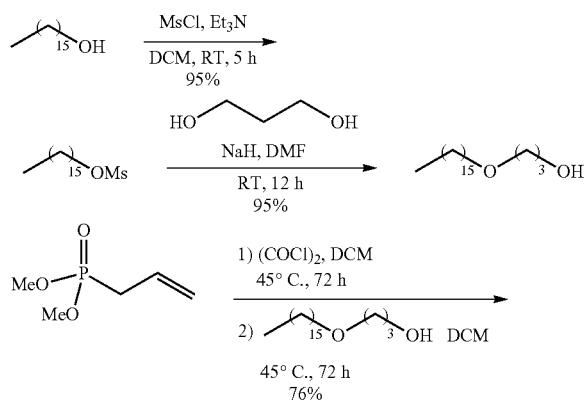

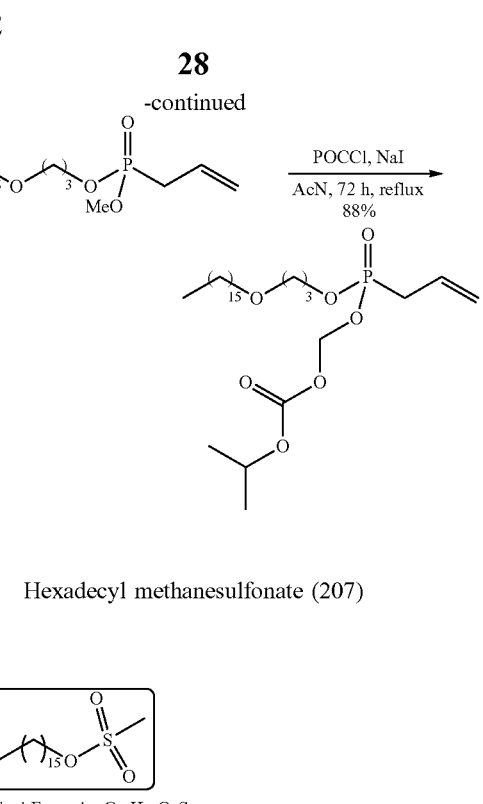

Hexadecyl methanesulfonate (207)

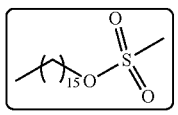

Chemical Formula: C$_{17}$H$_{36}$O$_3$S
Molecular Weight: 320.53

Triethylamine (5.75 mL, 1 eq., 41.2 mmol) was added to a solution of starting material hexadecyl alcohol (10 g, 1 eq., 41.2 mmol) and dichloromethane (100 mL). The temperature was set to 0° C., and methansulfonyl chloride (3.2 mL, 1 eq., 41.2 mmol) was added dropwise. The solution was then stirred at room temperature during 5 h. The resulting mixture was kept at −4° C. during 72 h, followed by the filtration of the precipitate. The filtrate was evaporated and purified by silica gel column (PE/AE 9:1) to afford desired compound 207 as a white powder. (12.5 g, 95%) $^1$H NMR (400 MHz, CDCl$_3$) δ 4.22 (t, J=6.6 Hz, 2H, CH$_2$—O), 3.00 (s, 3H, CH$_3$—S), 1.71 (tt, J=14.5, 6.6 Hz, 2H, CH$_2$-β-O), 1.23 (s, 27H, CH$_2$), 0.85 (m, 3H, CH$_3$). CAS: 124-63-0

Hexadecyloxypropyl alcohol (208)

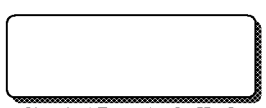

Chemical Formula: C$_{19}$H$_{40}$O$_2$
Molecular Weight: 300.53

Under N$_2$ atmosphere, commercial 1,3-propanediol (9.02 mL, 5 eq., 124.8 mmol) was dissolved in 200 mL DMF, and sodium hydride (60% in oil, 2.49 g, 2.5 eq., 62.4 mmol) was carefully added. The solution was stirred 30 minutes at room temperature, followed by the addition of 207 (8 g, 1 eq., 25 mmol). This mixture was stirred overnight at room temperature, and the crude product was quenched with cold water (200 mL), dissolved in EtOAc (100 mL), extracted 5 times with water (5×100 mL), washed with brine (100 mL) and dried over MgSO$_4$. After evaporation of all volatiles, the product was purified by flash column chromatography (PE/EtOAc 8:2) to give compound 208 as a white powder. (7.12 g, 95%)$^1$H NMR (400 MHz, CDCl$_3$) δ 3.75 (q, J=5.5 Hz, 2H, H$_a$), 3.58 (t, J=5.6 Hz, 2H, H$_c$), 3.40 (t, J=6.6 Hz, 2H, CH$_2$), 2.46 (t, J=5.5 Hz, 1H, OH), 1.80 (p, J=5.6 Hz, 2H, H$_b$), 1.23 (s, 26H, CH$_2$), 0.85 (m, 3H, CH$_3$). CAS: 23377-40-4

1-[3-[allyl(methoxy)phosphoryl]oxypropoxy]hexadecane (209)

Chemical Formula: C$_{23}$H$_{47}$O$_4$P
Molecular Weight: 418.60

Oxalylchloride (2.04 mL, 3 eq., 23.8 mmol) was added to a solution of dimethyl allylphosphonate (1.19 g, 1 eq., 7.9 mmol) in dichloromethane (35 mL). This mixture was gently refluxed during 3 days at 45° C. After evaporation of all volatiles, the crude compound was diluted in 35 mL of dichloromethane. Hexadecyloxypropyl alcohol (2.5 g, 1.05 eq., 8.3 mmol) and freshly distilled triethylamine (1.6 mL, 1.5 eq., 20 mmol) were then added subsequently and the resulting solution was refluxed to during 3 days at 45° C. The volatiles were removed under reduced pressure, and the residue was purified by flash column chromatography (eluting PE/EtOAc 9:1-6:4-0:1) to afford 209 as a white amorphous solid. (2.52 g, 76%) $^1$H NMR (400 MHz, CDCl$_3$) δ 5.75 (m, 1H, CH=CH$_2$), 5.23 (m, 2H, CH$_2$—CH=CH$_2$), 4.13 (dt, J=6.5, 1.7 Hz, 2H, Hc), 3.73 (d, J=10.9 Hz, 3H, O—CH$_3$), 3.48 (t, J=6.2 Hz, 2H, Ha), 3.38 (t, J=6.7 Hz, 2H, CH$_2$—O), 2.62 (ddt, J=22.0, 7.4, 1.1 Hz, 2H, CH$_2$—P), 1.91 (p, J=6.3 Hz, 2H, CH$_2$-b), 1.54 (p, J=6.9 Hz, 2H, CH$_2$—CH$_2$—O), 1.32-1.22 (m, 26H, CH$_2$), 0.87 (t, J=6.8 Hz, 3H, CH$_3$). $^{31}$P NMR (162 MHz, CDCl$_3$) δ 28.3. CAS: 1258789-65-9

Allyl(3-hexadecoxypropoxy)phosphoryloxymethyl isopropyl carbonate (210)

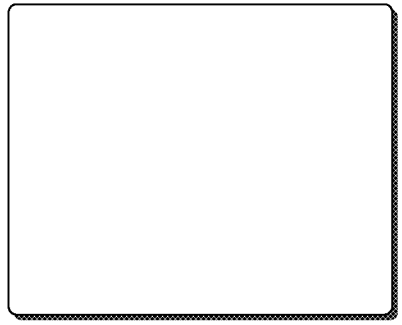

Chemical Formula: C$_{27}$H$_{53}$O$_7$P
Molecular Weight: 520.69

209 (2.20 g, 1 eq., 5.26 mmol) was dissolved in dry acetonitrile (5 mL). Chloromethyl-isopropylcarbonate (1.05 mL, 1.5 eq., 7.89 mmol) and anhydrous sodium iodide (828 mg, 1.05 eq., 5.52 mmol) were respectively added and the mixture was refluxed at 90° C. during 3 days under N2 atmosphere. To the resulting solution was added 100 mL of diethyl ether and 20 mL of water. The organic layer was then washed with an aqueous solution of Na$_2$S$_2$O$_3$ (20 mL), brine (20 mL) and dried over MgSO$_4$. The volatiles were removed under reduced pressure and the residue was purified by flash column chromatography (PE/EtOAc 75:25) to afford 210 as an colorless oil. (2.4 g, 88%)
$^1$H NMR (400 MHz, CDCl$_3$) δ 5.74 (m, 1H, CH-γ phosph), 5.62 (m, 1H, O—CH$_2$—O), 5.21 (m, 2H, CH$_2$-β phosph), 4.90 (sept., J=6.3 Hz, 2H, CH—CH$_3$ POC), 4.17 (m, 2H, CH$_2$-c), 3.45 (t, J=6.3 Hz, 2H, CH$_2$-a), 3.36 (t, J=6.7 Hz, 2H, CH$_2$—O), 2.65 (dd, J=22.4, 7.4 Hz, 2H, CH$_2$—P), 1.89 (p, J=6.3 Hz, 2H, CH$_2$-b), 1.52 (p, J=6.9 Hz, 2H, CH$_2$—CH$_2$—O), 1.33-1.20 (m, 32H, CH$_2$, CH$_3$ POC), 0.85 (t, J=6.7 Hz, 3H, CH$_3$) $^{31}$P NMR (162 MHz, CDCl$_3$) δ 26.7. HRMS-ESI (m/z) [M+H]$^+$ calcd for C$_{27}$H$_{54}$O$_7$ 521.3607, found 521.3599.
CAS: 1258789-66-0

Allyl Phosphonoamidate Synthons

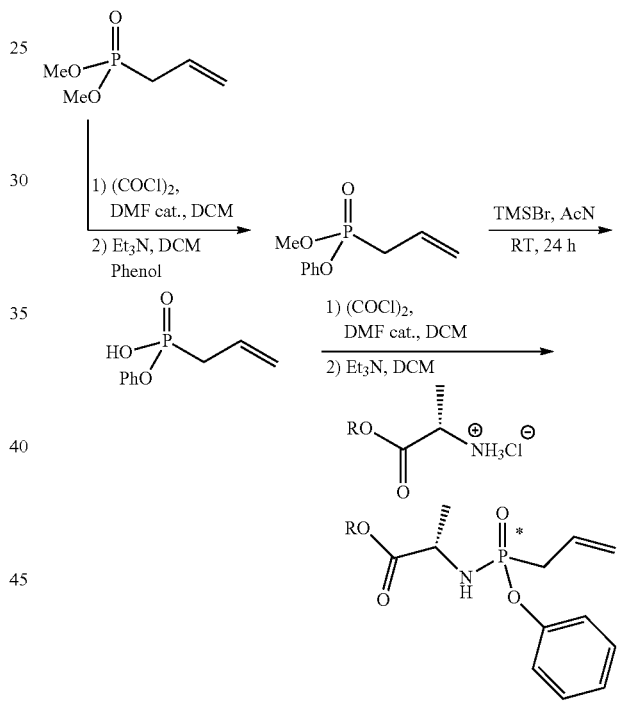

Methoxyphenoxy allylphosphonate

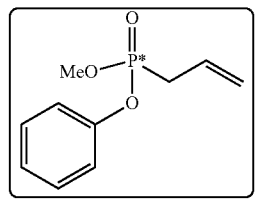

Chemical Formula: C$_{10}$H$_{13}$O$_3$P
Molecular Weight: 212.18

To a mixture of dimethylallylphosphonate 89 (4.9 g, 1 eq., 32.5 mmol) and DCM (150 mL), oxalyl chloride (8.6 mL, 3 eq., 97.5 mmol) was added. The reaction was stirred 24 h at reflux, followed by the removal of the volatiles in vacuo to obtain the chloromethyl allylphosphonate. In another flask, a solution of phenol (6.12 g, 2 eq., 65 mmol), triethylamine (8.8 mL, 2 eq., 65 mmol) and DCM (0.2 M) was stirred at room temperature. The phosphonate residue was then dissolved in DCM (0.2 M), and slowly added to this solution, and refluxed during 48 h. After evaporation of all volatiles, the residue was purified by silica gel column chromatography, eluting Petroleum ether/Ethyl acetate 8/2, to afford 306 as a colorless oil. (4.5 g, 65%) $^1$H NMR (400 MHz, CDCl$_3$) δ 7.29 (m, 2H, H$^{Ar}$), 7.15 (m, 3H, H$^{Ar}$D, 5.80 (m, 1H, CH=CH$_2$), 5.24 (m, 2H, CH$_2$=CH), 3.76 (d, J=11.1 Hz, 3H, OMe), 2.73 (dd, J=22.0, 7.3 Hz, 2H, CH$_2$—P). $^{13}$C NMR (101 MHz, CDCl$_3$) δ 150.46 (d, J=8.5 Hz, C$^{quat}$), 129.72 (C$^{Ar}$), 126.59 (d, J=11.6 Hz, CH=CH$_2$), 124.95 (d, J=1.3 Hz, C$^{Ar}$), 120.67 (d, J=14.8 Hz, CH$_2$=CH), 120.42 (d, J=4.4 Hz, C$^{Ar}$), 53.16 (d, J=5.1 Hz, OMe), 31.21 (d, J=139.9 Hz, CH$_2$—P). $^{31}$P NMR (162 MHz, CDCl$_3$) δ 25.06. HRMS (ESI): m/z [M+H]$^+$ calcd for C$_{10}$H$_{14}$O$_3$P: 213.0681, found: 213.0675.

Phenyloxy allylphosphinic acid (307)

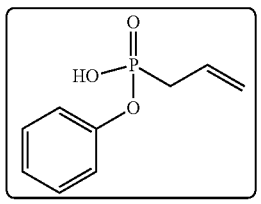

Chemical Formula: C$_9$H$_{11}$O$_3$P
Molecular Weight: 198.16

Bromotrimethylsilane (8.9 mL, 6 eq., 61.8 mmol) was slowly added to a solution of 306 (2.2 g, 1 eq., 10.3 mmol) in DCM (110 mL). After 24 h at room temperature and evaporation of all volatiles, the crude product was co-evaporated 5 times with methanol (5×15 mL). The residue was then purified by flash column chromatography (DCM/MeOH 95/5) to obtain desired product 307 as an amorphous white solid. (1.85 g, 91%)$^1$H NMR (400 MHz, CDCl$_3$) δ 8.12 (s, 1H, OH), 7.28 (m, 2H, HAD, 7.14 (m, 3H, HAD, 5.79 (m, 1H, CH=CH$_2$), 5.22 (m, 2H, CH$_2$=CH), 2.67 (dd, J=22.5, 7.3 Hz, 2H, CH$_2$—P). $^{13}$C NMR (101 MHz, CDCl$_3$) δ 150.18 (d, J=8.9 Hz, C$^{quat}$), 129.61 (C$^{Ar}$), 126.65 (d, J=11.4 Hz, CH=CH$_2$), 124.92 (C$^{Ar}$), 120.79 (d, J=4.4 Hz, C$^{Ar}$), 120.66 (d, J=14.9 Hz, CH$_2$=CH), 31.55 (d, J=141.5 Hz, CH$_2$—P). $^{31}$P NMR (162 MHz, CDCl$_3$) δ 26.26. HRMS (ESI): m/z [M+H]$^+$ calcd for C$_9$H$_{12}$O$_3$P: 199.0525, found: 199.0518.

Methyl (2S)-2-[[allyl(phenoxy)phosphoryl]amino]propanoate (318)

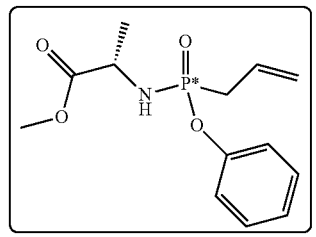

Chemical Formula: C$_{13}$H$_{18}$NO$_4$P
Molecular Weight: 283.26

Following general procedure 1, compound 307 (1.3 g, 1 eq., 6.56 mmol) was dissolved in DCM (25 mL). A catalytical amount of DMF (0.16 mL) was then introduced, followed by the addition of oxalyl chloride (1.13 mL, 2 eq., 13.1 mmol). After 30 min. at 0° C. and 1 h 30 at room temperature, the volatiles were removed, and the residue diluted with 16 mL of DCM to afford solution A. A second solution was prepared with L-alanine methyl ester chlorhydrate (1.10 g, 1.2 eq., 7.87 mmol), freshly distilled triethylamine (7.09 mL, 8 eq., 52.5 mmol) and DCM. To this mixture the solution A was slowly added at 0° C., and stirred 24 h at room temperature. After the described work-up, the residue was purified twice by flash column chromatography, eluting PE/EA (55:45 to 5:5) to afford the mixture of the two diastereoisomers 318 as a colorless oil. (960 mg, 52%, ratio diastereoisomer 1:diastereoisomer 2 of 55:45)$^1$H NMR (400 MHz, CDCl$_3$) δ 7.30 (m, 2H, H$^4$D, 7.18 (m, 3H, H$^4$D, 5.87 (m, 1H, CH=CH$_2$), 5.27 (m, 2H, CH$_2$=CH), 4.08 (m, 1H, CH—NH), 3.66 (d, J=10.6 Hz, 3H, OMe), 3.32 (2×t, J=10.1 Hz, 1H, NH), 2.77 (m, 2H, CH$_2$—P), 1.28 (2×d, J=7.2 Hz, 3H, CH$_3$—CH). $^{13}$C NMR (101 MHz, CDCl$_3$) δ 174.53 (d, J=6.1 Hz, C=O), 174.20 (d, J=5.3 Hz, C=O), 150.53 (d, J=9.5 Hz, C$^{quat}$), 150.45 (d, J=9.9 Hz, C$^{quat}$), 129.65 (C$^{Ar}$), 129.60 (C$^{Ar}$), 127.68 (d, J=11.4 Hz, CH=CH$_2$), 127.52 (d, J=11.2 Hz, CH=CH$_2$), 124.72 (d, J=1.2 Hz, C$^{Ar}$), 124.68 (d, J=1.1 Hz, C$^4$D, 120.70 (d, J=4.8 Hz, C$^{Ar}$), 120.60 (d, J=14.4 Hz, CH$_2$=CH), 120.57 (d, J=4.8 Hz, C$^{Ar}$), 52.35 (CH$_3$—O), 49.62 (CH—NH), 49.45 (CH—NH), 34.32 (d, J=128.3 Hz, CH$_2$—P), 34.30 (d, J=128.3 Hz, CH$_2$—P), 21.60 (d, J=4.3 Hz, CH$_3$), 21.46 (d, J=3.8 Hz, CH$_3$). $^{31}$P NMR (162 MHz, CDCl$_3$) δ 26.78, 26.34. HRMS (ESI): m/z [M+H]$^+$ calcd for C$_{13}$H$_{19}$NO$_4$P: 284.1052 found: 284.1045.

Isopropyl (2S)-2-[[allyl(phenoxy)phosphoryl]amino]propanoate (319)

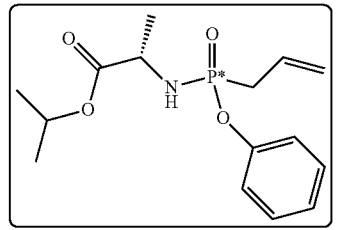

Chemical Formula: C$_{15}$H$_{22}$NO$_4$P
Molecular Weight: 311.32

Following general procedure 1, compound 307 (1.3 g, 1 eq., 6.56 mmol) was dissolved in DCM (25 mL). A catalytical amount of DMF (0.16 mL) was then introduced, followed by the addition of oxalyl chloride (1.13 mL, 13.1 mmol, 2 eq.). After 30 min. at 0° C. and 1 h 30 at room temperature, the volatiles were removed, and the residue diluted with 16 mL of DCM to afford solution A. A second solution was prepared with L-alanine isopropyl ester chlorhydrate (1.32 g, 1.2 eq., 7.87 mmol), freshly distilled triethylamine (7.09 mL, 8 eq., 52.5 mmol) and DCM. To this mixture the solution A was slowly added at 0° C., and stirred 24 h at room temperature. After the described work-up, the residue was purified twice by flash column chromatography, eluting PE/EA (65:35) to afford the mixture of the two diastereoisomers 319 as a colorless oil. (1.16 g, 57%, ratio diastereoisomer 1:diastereoisomer 2 of 6:4) $^1$H NMR (400 MHz, CDCl$_3$) δ 7.32 (m, 2H, HAD, 7.19 (m, 3H, H$^4$D, 5.92 (m, 1H, CH=CH$_2$), 5.28 (m, 2H, CH$_2$=CH), 4.99 (pd, J=6.3, 4.9 Hz, 1H, CH-iPr), 4.04 (m, 1H, CH—NH), 3.38 (2×t, J=10.1 Hz, 1H, NH), 2.78 (m, 2H, CH$_2$—P), 1.26 (m, 9H, CH$_3$—CH—NH, CH$_3$ iPr). $^{13}$C NMR (101 MHz, CDCl$_3$) δ 173.24 (d, J=5.7 Hz, C=O), 150.58 (d, J=9.5 Hz, C$^{quat}$), 150.45 (d, J=9.9 Hz, C$^{quat}$), 129.65 (C$^{Ar}$), 129.59 (C$^{Ar}$), 127.71 (d, J=11.4 Hz, C$^2$), 127.53 (d, J=11.4 Hz, C$^2$), 124.69 (C$^{Ar}$), 124.65 (C$^{Ar}$), 120.75 (C$^{3'}$/C$^{Ar}$), 120.70 (C$^{3'}$/C$^{Ar}$), 120.68 (C$^{3'}$/C$^{Ar}$), 120.64 (C$^{3'}$/C$^{Ar}$), 120.59 (C$^{3'}$/C$^{Ar}$), 120.55 (C$^{3'}$/C$^{Ar}$), 120.50 (C$^{3'}$/C$^{Ar}$), 69.09 (CH iPr), 69.07 (CH iPr), 49.77 (CH—NH), 49.62 (CH—NH), 34.30 (d, J=129.3 Hz, CH$_2$—P), 21.71 (CH$_3$), 21.70 (CH$_3$), 21.67 (CH$_3$), 21.62 (CH$_3$), 21.60 (CH$_3$), 21.57 (CH$_3$). $^{31}$P NMR (162 MHz, CDCl$_3$) δ 26.77, 26.35. HRMS (ESI): m/z [M+H]$^+$ calcd for C$_{15}$H$_{23}$NO$_4$P: 312.1365 found: 312.1359.

3—Synthesis of Butenyl Phosphonate Synthons Bearing Biolabile Groups bis-OMe-3-butenyl phosphonate (217)

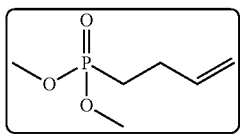

Chemical Formula: C$_6$H$_{13}$O$_3$P
Molecular Weight: 164.14

Commercially available dimethyl phosphite (4 g, 1 eq., 36.4 mmol) was added dropwise to a solution of NaH (60% in oil, 1.45 g, 1 eq., 36.4 mmol) in THF (40 mL) at 0° C. After 30 min. stirring at 0° C., bromo buten-3-yl (3.7 mL, 1 eq., 36.4 mmol) was added dropwise, and the reaction was stirred 24 h at room temperature. To the solution 20 mL of water was added, extracted 3 times with dichloromethane (3×20 mL), and the organic layers were dried over MgSO$_4$. The mixture was filtrated and concentrated under vacuum. The crude product was purified by flash column chromatography (AcOEt/MeOH 95:5) affording 217 (4.1 g, 71%) as a colorless oil. $^1$H NMR (400 MHz, CDCl$_3$) δ 5.80 (ddt, J=16.6, 10.1, 6.3 Hz, 1H, CH=CH$_2$), 5.01 (m, 2H, CH$_2$=CH), 3.73 (s, 3H, CH$_3$—O), 3.68 (s, 3H, CH$_3$—O), 2.31 (m, 2H, CH$_2$—CH=CH$_2$), 1.80 (m, 2H, CH$_2$—P). $^{13}$C NMR (101 MHz, CDCl$_3$) δ 137.01 (d, J=17.4 Hz, CH=CH$_2$), 115.26 (d, J=1.2 Hz, CH$_2$=CH), 52.29 (d, J=6.6 Hz, CH$_3$—O), 26.38 (d, J=4.5 Hz, CH$_2$—CH=CH$_2$), 24.02 (d, J=140.9 Hz, CH$_2$—P) $^{31}$P NMR (162 MHz, CDCl$_3$) δ 34.09. CAS: 205644-46-8 bis-POM-3-butenyl phosphonate

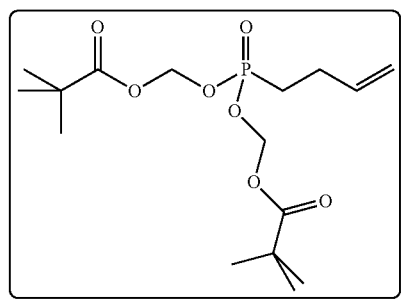

Chemical Formula: C$_{16}$H$_{29}$O$_7$P
Molecular Weight: 364.37

Dimethyl butenylphosphonate 217 (2 g, 1 eq, 12.1 mmol), sodium iodide (3.65 g, 2 eq., 24.4 mmol) and chloromethylpivalate (4.3 mL, 2.5 eq., 30.5 mmol) were dissolved in anhydrous acetonitrile (13 mL), and refluxed for 3 days. The crude product was diluted with Et$_2$O (50 mL), washed with water (10 mL), aqueous solution of Na$_2$S$_2$O$_3$ (10 mL), dried over MgSO$_4$, filtrated and concentrated under vacuum. Further purification of the product on silica column using PE/EtOAc 8:2 to 7:3 as eluent yielded 187 (3.02 g, 68%) as a colorless oil. $^1$H NMR (400 MHz, CDCl$_3$) δ 5.81 (ddt, J=16.7, 10.3, 6.3 Hz, 1H, CH=CH$_2$), 5.67 (d, J=13.1 Hz, 2H, O—CH$_2$—O), 5.04 (m, 2H, CH$_2$=CH), 2.34 (m, 2H, CH$_2$—CH$_2$=CH), 1.94 (m, 2H, CH$_2$—P), 1.24 (s, 18H, CH$_3$ POM). $^{13}$C NMR (101 MHz, CDCl$_3$) δ 176.85 (C=O), 138.41 (d, J=18.6 Hz, CH=CH$_2$), 115.55 (d, J=1.0 Hz, CH$_2$=CH), 81.32 (d, J=6.2 Hz, O—CH$_2$-0), 38.72 (C$^{aqua}_{POM}$), 26.84 (CH$_3$), 26.00 (d, J=4.7 Hz, CH$_2$—CH=CH$_2$), 25.81 (d, J=139.90 Hz, CH$_2$—P) $^{31}$P NMR (162 MHz, CDCl$_3$) δ 32.40. HRMS-ESI (m/z) [M+H]$^+$ calcd for C$_{16}$H$_{30}$O$_7$P 365.1730, found 365.1723.

III—Preparation of the Compounds of the Invention

General Procedure 3 - Cross metathesis

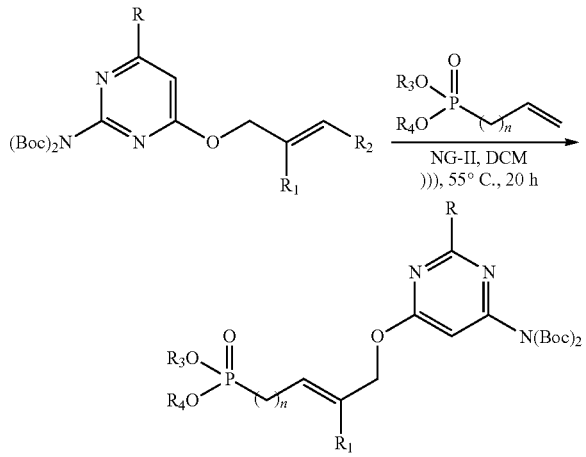

To a solution of pyrimidine and phosphonate in freshly distilled CH$_2$Cl$_2$ (0.1 M). The mixture was sonicated at 55° C. (80 kHz, 100 W) under a gentle nitrogen flow. RuCl$_2$PCy$_3$IMesBenzylidene ruthenium catalyst was added in four or five equal portions and after 24 h of reaction all volatiles were evaporated. The purification by flash column chromatography using an elution gradient of Petroleum ether/EtOAc gave desired compounds as oils.

General Procedure 4 - Deprotection of Boc-Group

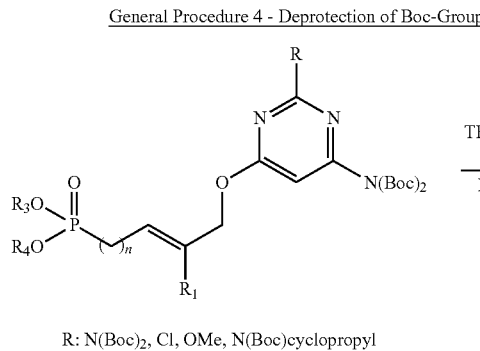

R: N(Boc)$_2$, Cl, OMe, N(Boc)cyclopropyl

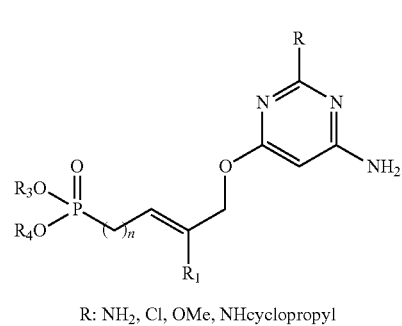

R: NH$_2$, Cl, OMe, NHcyclopropyl

Trifluoroacetic acid (100 eq.) was added dropwise to a mixture of Boc-compound (1 eq.) in CH$_2$Cl$_2$ (2:1 CH$_2$Cl$_2$/TFA v/v). The reaction was stirred at room temperature for 2 h and then volatiles were removed under reduced pressure. The crude product was extracted with EtOAc, washed with NaHCO$_3$ until pH 7, dried over MgSO$_4$, filtrated and concentrated under vacuum. Pure compounds were obtained after purification by flash column chromatography with DCM/MeOH (97:3) as eluent.

Example 1: Preparation of Compound (1)

1. Preparation of [[(E)-4-[2,6-bis[bis(tert-butoxycarbonyl)amino]pyrimidin-4-yl]oxybut-2'-enyl]-(2,2-dimethylpropanoyloxymethoxy)phosphoryl]oxymethyl 2,2-dimethylpropanoate (250)

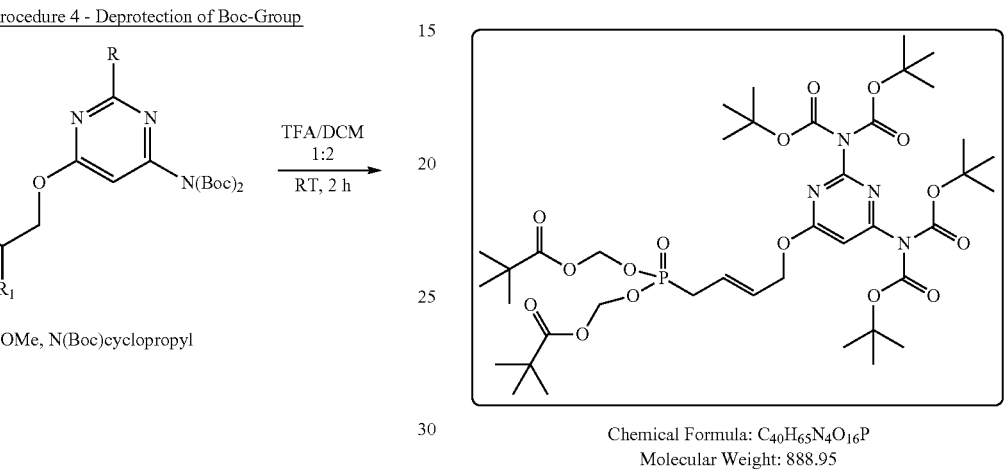

Chemical Formula: C$_{40}$H$_{65}$N$_4$O$_{16}$P
Molecular Weight: 888.95

Following the general procedure 3 from compound 246 (50 mg, 1 eq., 0.09 mmol) with allyl-bis(POM)phosphonate (60 mg, 2 eq., 0.17 mmol) and 15 mol % RuCl$_2$PCy$_3$IMesBenzylidene ruthenium catalyst (12 mg, 0.013 mmol, added in 3 equal portions of 3 mol %) in freshly distilled CH$_2$Cl$_2$ (2 mL), compound 250 (33 mg, 43%) was isolated as a light brown oil after purification by silica gel column chromatography using petroleum ether/EtOAc (8:2 to 7:3) as eluent. $^1$H NMR (400 MHz, CDCl$_3$) δ 6.91 (s, 1H, H$^5$), 5.88 (ddt, J=15.5, 5.5, 5.1 Hz, 1H, H$^{2'/3'}$), 5.76 (ddt, J=15.3, 7.0, 6.9 Hz, 1H, H$^{2'/3'}$), 5.67 (m, 4H, O—CH$_2$—O), 4.79 (dd, J=5.1 Hz, 2H, CH$_2$—O), 2.72 (dd, J=22.6, 7.0 Hz, 2H, H$^{4'}$), 1.50 (s, 18H, CH$_3$ Boc), 1.43 (s, 18H, CH$_3$ Boc), 1.23 (s, 18H, CH$_3$ POM). $^{13}$C NMR (101 MHz, CDCl$_3$) δ 176.97 (C=O $^{POM}$), 171.27 (C$^6$), 159.99 (C$^4$), 156.57 (C$^2$), 150.54 (C=O $^{Boc}$), 150.05 (C=O $^{Boc}$), 130.55 (d, J=15.0 Hz, C$^{2'/3'}$), 122.55 (d, J=12.1 Hz, C$^{2'/3'}$), 96.36 (C$^5$), 84.27 (C$^{quat\,Boc}$), 83.22 (C$^{quat\,Boc}$), 81.72 (d, J=6.4 Hz, O—CH$_2$—O), 66.82 (J=2.4 Hz, CH$_2$—O), 38.87 (C$^{quat\,POM}$), 31.05 (d, J=140.0 Hz, C$^{4'}$), 27.98 (CH$_3$ Boc), 27.86 (CH$_3$ Boc), 26.99 (CH$_3$). $^{31}$P NMR (162 MHz, CDCl$_3$) δ 27.13. HRMS-ESI (m/z) [M+H]$^+$ calcd for C$_{40}$H$_{66}$N$_4$O$_{16}$P 889.4206, found 889.4200.

2. [(Z)-2-[(2,6-bis[bis(tert-butoxycarbonyl)aminopyrimidin-4-yl)oxymethyl]-4-[3hexadecoxypropoxy-(isopropoxycarbonyloxymethoxy)-phosphoryl]but-2'-enyl]acetate (220)

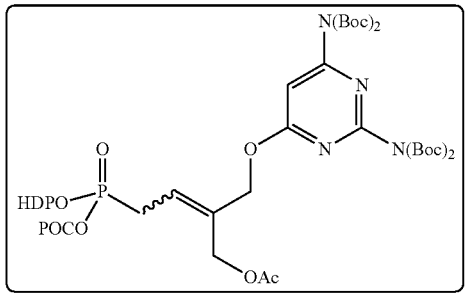

Following the general procedure 3 from compound 200 (800 mg, 1.25 mmol) and compound 210 (1.3 g, 2.5 mmol) in freshly distilled $CH_2Cl_2$ (24 mL), 10 mol % $RuCl_2PCy_3IMesBenzylidene$ ruthenium catalyst was added in five equal portions. The mixture was sonicated at 55° C. (80 kHz, 100 W) under a gentle nitrogen flow. After evaporation of all volatiles, the purification by flash column chromatography using an elution gradient of Petroleum ether/EtOAc gave desired compounds 220 as oils in 55% yield (686 mg) of isomer mixture (Z/E; 1/1).

$^1$H NMR (250 MHz, $(CD_3)_2CO$) δ 7.03 (s, 1H, $H_{ar}$, E isomer), 7.02 (s, 1H, $H_{ar}$, Z isomer), 5.81 (m, 1H, CH=C), 5.64 (m, 2H, O—$CH_2$—O), 5.06 (d, J=2.5 Hz, 2H, $CH_2$-ODAPY, E isomer), 4.96 (d, J=2.5 Hz, 2H, $CH_2$—ODAPY, Z isomer), 4.89 (q, J=6.07 Hz, 1H, $CH_3$—CH—$CH_3$, POC), 4.79 (d, J=2.5 Hz, 2H, $CH_2$—OAc, E isomer), 4.70 (d, J=2.5 Hz, 2H, $CH_2$—OAc, Z isomer), 4.12 (m, 2H, $CH_2$-c), 3.49 (t, J=6.08 Hz, 2H, $CH_2$-a), 3.41 (t, J=6.43 Hz, 2H, $(CH_2)_{14}$—$CH_2$—O, HDP), 2.86 (dd, J=23.4, 8.0 Hz, 2H, $CH_2$—P), 2.01 (s, 3H, $CH_3$, Ac), 1.88 (m, 2H, $CH_2$-b), 1.55 (m, 2H, $(CH_2)_{13}$—$CH_2$—$CH_2$—O, HDP), 1.53 (s, 18H, $CH_3$, Boc), 1.48 (s, 18H, $CH_3$, Boc), 1.30 (m, 32H, $(CH_2)_{13}$, HDP, 2$CH_3$, POC), 0.88 (m, 3H, $CH_3$, HDP).

3. Preparation of Compound (1): [[(E)-4-(2,6-diaminopyrimidin-4-yl)oxybut-2'-enyl]-(2,2-dimethylpropanoyloxymethoxy)phosphoryl]oxymethyl 2,2-dimethylpropanoate (255)

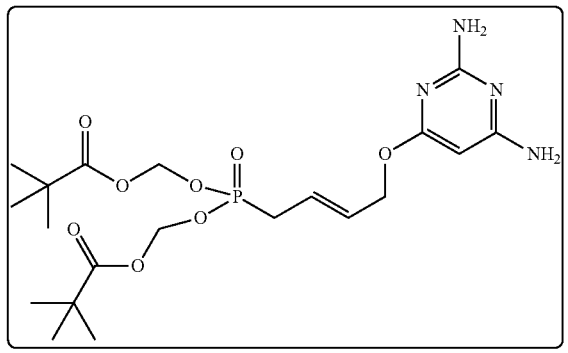

Chemical Formula: $C_{20}H_{33}N_4O_8P$
Molecular Weight: 488.48

Following the general procedure 4 from compound 250 (177 mg, 1 eq., 0.20 mmol) using TFA (1.5 mL, 100 eq., 19.91 mmol) in $CH_2Cl_2$ (3 mL) for 2 h, deprotected compound 256 (85 mg, 87%)(or compound (1)) was obtained as a colorless oil after flash column chromatography with EtOAc then EtOAc/MeOH (95:5). $^1$H NMR (400 MHz, $(CD_3)_2CO$) δ 5.89 (ddt, J=15.3, 5.9, 5.6 Hz, 1H, $H^{2'/3'}$), 5.70 (m, 5H, $H^{2'/3'}$, O—$CH_2$—O), 5.60 (bs, 2H, $NH_2$), 5.50 (bs, 2H, $NH_2$), 5.21 (s, 1H, $H^5$), 4.67 (dd, J=5.0 Hz, 2H, $CH_2$—O), 2.76 (dd, J=22.4, 7.2 Hz, 2H, $H^{4'}$), 1.22 (s, 18H, $CH_3$ POM). $^{13}$C NMR (101 MHz, $(CD_3)_2CO$) δ 177.11 (C=O $^{POM}$), 171.30 ($C^6$), 167.27 ($C^4$), 164.14 ($C^2$), 132.55 (d, J=15.1 Hz, $C^{2'/3'}$), 122.20 (d, J=11.5 Hz, $C^{2'/3'}$), 82.42 (d, J=6.3 Hz, O—$CH_2$—O), 77.91 ($C^5$), 65.38 (d, J=2.3 Hz, $CH_2$—O), 39.24 ($C^{quat\ POM}$) 31.21 (d, J=139.6 Hz, $C^{4'}$), 27.11 ($CH_3$). $^{31}$P NMR (162 MHz, $(CD_3)_2CO$) δ 26.99. HRMS-ESI (m/z) $[M+H]^+$ calcd for $C_{20}H_{34}N_4O_8P$ 489.2109, found 489.2109.

Example 2: Preparation of Compound (2)

[[(E)-4-(2,6-diaminopyrimidin-4-yl)oxybut-2'-enyl]-(3-hexadecoxypropoxy)phosphoryl]oxymethyl isopropyl carbonate

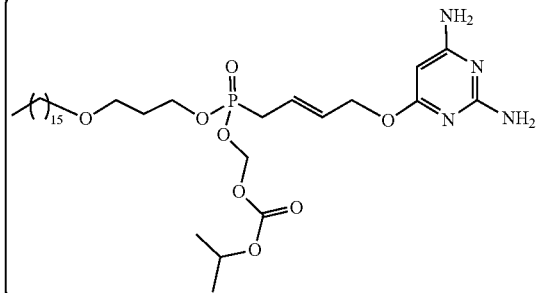

Chemical Formula: $C_{32}H_{59}N_4O_8P$
Molecular Weight: 658.82

Starting from 210 (206 mg, 2 eq., 0.38 mmol), the general procedure 3 was applied on compound 246 (112 mg, 1 eq., 0.19 mmol) and 15 mol % $RuCl_2PCy_3IMesBenzylidene$ ruthenium catalyst (25 mg, 0.027 mmol, added in 3 equal portions of 5 mol %) in freshly distilled $CH_2Cl_2$ (4 mL, 0.1 M). The crude mixture was not isolated, and then engaged in the next step after a simple filtration on silica gel, using PE/EtOAc 8/2 as eluting system. General procedure 4 was used on the intermediar compound (70 mg, 1 eq., 0.065 mmol), TFA (0.50 mL, 100 eq., 6.5 mmol) in $CH_2Cl_2$ (1 mL) for 1 h, giving deprotected compound 258 (or compound (2)) as a colorless oil. (45 mg, 32%)$^1$H NMR (400 MHz, $(CD3)_2CO$) δ 5.81 (m, 2H, $H^{3'}$, $H^{2'}$), 5.62 (m, 6H, O—$CH_2$—O, $NH_2$), 5.22 (s, 1H, $H^5$), 4.90 (sept., J=6.2 Hz, 1H, CH—$CH_3$ POC), 4.68 (t, J=5.2 Hz, 2H, $H^{1'}$), 4.13 (m, 2H, $CH_2$-c), 3.48 (t, J=6.1 Hz, 2H, $CH_2$-a), 3.39 (t, J=6.5 Hz, 2H, $CH_2$—O), 2.70 (dd, J=22.4, 6.9 Hz, 2H, $CH_2$—P), 1.87

(p, J=6.1 Hz, 2H, $CH_2$-b), 1.54 (t, J=6.7 Hz, 2H, $CH_2$—$CH_2$—O), 1.41-1.21 (m, 32H, $CH_2$, $CH_3$ POC), 0.86 (m, 3H, $CH_3$). $^{13}C$ NMR (101 MHz, $(CD_3)_2CO$) δ 170.50 ($C^6$), 166.12 ($C^4/C^2$), 162.99 ($C^4/C^2$), 153.19 (C=O POC), 131.17 (d, J=14.7 Hz, $C^{2'}$), 122.20 (d, J=11.3 Hz, $C^{3'}$), 84.34 (d, J=6.0 Hz, O—$CH_2$—O), 77.06 ($C^5$), 72.55 ($C^{CH\ POC}$), 70.60 ($CH_2$—O), 66.23 ($CH_2$-a), 64.69 ($H^{1'}$), 62.93 (d, J=7.0 Hz, $CH_2$-c), 31.73 ($CH_2$), 30.82 (under (CD3)2CO peak, d), 30.70 (d, J=6.1 Hz, $CH_2$-b), 29.65 ($CH_2$), 29.51 ($CH_2$), 29.49 ($CH_2$), 29.37 ($CH_2$), 29.17 ($CH_2$), 26.07 ($CH_2$), 22.42 ($CH_2$), 20.94 ($CH_2$), 13.45 ($CH_3$). $^{31}P$ NMR (162 MHz, (CD3)2CO) δ 26.80. HRMS-ESI (m/z) $[M+H]^+$ calcd for $C_{32}H_{60}N_4O_8P$ 659.4149, found 659.4145.

Example 3: Preparation of Compound (3)

[[(E)-4-(2,6-diaminopyrimidin-4-yl)oxybut-2'-enyl]-(isopropoxycarbonyloxymethoxy)phosphoryl]oxymethyl isopropyl carbonate

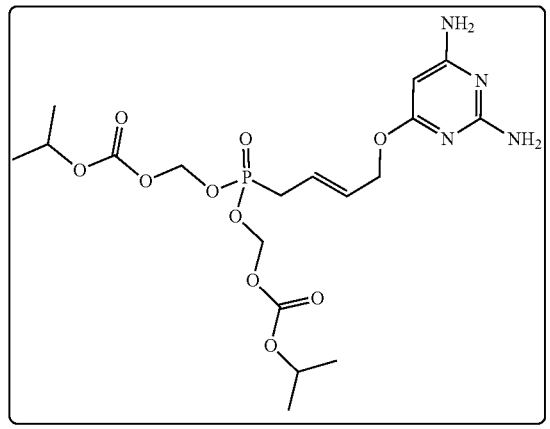

Chemical Formula: $C_{18}H_{29}N_4O_{10}P$
Molecular Weight: 492.42

Following the general procedure 3 from compound 205 (137 mg, 2 eq., 0.36 mmol) using 246 (103 mg, 1 eq., 0.18 mmol) and 15 mol % $RuCl_2PCy_3IMesBenzylidene$ ruthenium catalyst (25 mg, 0.027 mmol, added in 3 equal portions of 5 mol %) in freshly distilled $CH_2Cl_2$ (2 mL, 0.1 M). The crude compound was not isolated, and then engaged in the next step after a simple filtration on silica gel, using PE/EtOAc 75/25 as eluting system. General procedure 4 was followed on the intermediar compound (57 mg, 1 eq., 0.06 mmol), TFA (0.49 mL, 100 eq., 6.4 mmol) in $CH_2Cl_2$ (1 mL) for 1 h to give deprotected compound 257 (or compound (3)) after FCC with DCM/MeOH 95:5 as a colorless oil. (30 mg, 34%) $^1H$ NMR (400 MHz, (CD3)2CO) δ 5.80 (m, 2H, $H^{2'}$, $H^3$), 5.66 (m, 4H, O—$CH_2$—O), 5.54 (bs, 2H, $NH_2$), 5.40 (bs, 2H, $NH_2$), 5.21 (s, 1H, $H^5$), 4.90 (p, J=6.2 Hz, 2H, CH—POC), 4.68 (t, J=6.2 Hz, 2H, $CH_2$—O), 2.77 (dd, J=22.5, 7.2 Hz, 2H, $H^{4'}$), 1.29 (d, J=6.2 Hz, 12H, $CH_3$ POC). $^{13}C$ NMR (101 MHz, (CD3)2CO) δ 170.43 ($C^6$), 166.37 ($C^4$), 163.21 ($C^2$), 153.12 (C=O), 131.87 (d, J=15.4 Hz, $C^3$), 121.12 (d, J=11.2 Hz, $C^{2'}$), 119.99, 84.10 (d, J=6.1 Hz, O—$CH_2$—O), 77.02 ($C^5$), 72.74 (CH—$CH_3$ POC), 64.53 ($CH_2$—O), 31.47 (under (CD3)2CO peak, d), 20.89 ($CH_3$ POC). $^{31}P$ NMR (162 MHz, (CD3)2CO) δ 27.08.

Example 4: Preparation of Compound (4)

[[(Z/E)-3-(acetoxymethyl)-4-(2,6-diaminopyrimidin-4-yl)oxy-but-2'-enyl]-(2,2-dimethylpropanoyloxymethoxy)phosphoryl]oxymethyl 2,2-dimethylpropanoate (204)

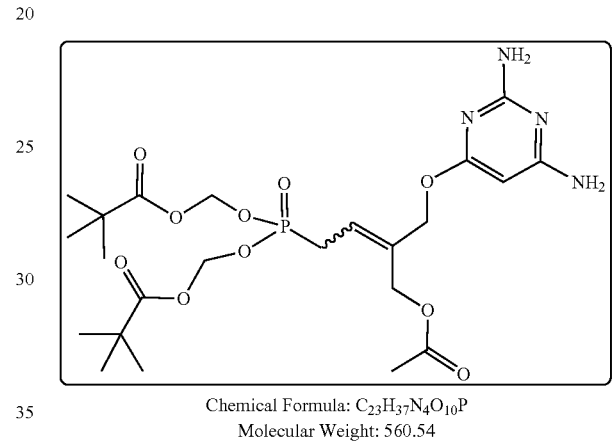

Chemical Formula: $C_{23}H_{37}N_4O_{10}P$
Molecular Weight: 560.54

General procedure 4 was applied with compound 202 (34 mg, 1 eq., 0.04 mmol), TFA (0.27 mL, 100 eq., 3.54 mmol) in $CH_2Cl_2$ (0.55 mL) for 1 h to give the deprotected compound 204 (16 mg, 83%) as a colorless oil after flash column chromatography purification with EtOAc. $^1H$ NMR (400 MHz, $(CD_3)_2CO$) δ 5.77 (s, 1H, $H^5$), 5.67 (m, 4H, O—$CH_2$—O), 5.53 (bs, 2H, $NH_2$), 5.42 (bs, 2H, $NH_2$), 5.22 (d, J=1.3 Hz, 1H, $H^5$), 4.84 (s, 2H, $CH_2$—O, E isomer), 4.74 (d, J=4.6 Hz, 2H, $CH_2$—O, Z isomer), 4.70 (s, 2H, $CH_2$—OAc, Z isomer), 4.61 (d, J=4.1 Hz, 2H, $CH_2$—OAc, E isomer), 2.97 (dd, J=23.1, 8.0 Hz, 2H, $H^4$), 2.01 (s, 3H, $CH_3$), 1.22 (s, 18H, $CH_3$ POM). $^{13}C$ NMR (101 MHz, $(CD_3)_2CO$) δ 177.17, 177.13 (C=O $^{POM}$), 171.36, 171.17 ($C^6$), 170.86, 170.59 (C=O Ac), 167.36 ($C^2$), 164.13, 164.08 ($C^4$), 137.20, 137.11, 137.05, 136.96 ($C^{2'}$), 121.66, 121.55, 121.41, 121.30 ($C^{3'}$), 82.59, 82.55, 82.52, 82.49 (O—$CH_2$—O), 78.05, 78.01 ($C^5$), 66.96, 66.93, 66.19, 66.17 ($CH_2$—O), 60.98, 60.96, 60.23, 60.21 ($CH_2$—O), 39.29 ($C^{quat\ POM}$), 28.23, 28.12 ($C^4$), 27.14 ($CH_3$ $^{POM}$), 26.85, 26.74 ($C^4$), 20.79, 20.73 ($CH_3$). $^{31}P$ NMR (162 MHz, $(CD_3)_2CO$) δ 26.62. HRMS-ESI (m/z) $[M+H]^+$ calcd for $C_{23}H_{38}N_4O_{10}P$ 561.2320, found 561.2319.

Example 5: Preparation of Compounds (5) and (13)

[(Z)-2-[(2,6-diaminopyrimidin-4-yl)oxymethyl]-4-[3-hexadecoxypropoxy (isopropoxycarbonyloxymethoxy)phosphoryl]but-2'-enyl]acetate (214)

Chemical Formula: $C_{35}H_{63}N_4O_{10}P$
Molecular Weight: 730.88

The pure mixture product 220 (1.562 g, 1.38 mmol) was engaged in the next step following the general procedure 4 in presence of TFA (10.5 mL, 100 eq., 138 mmol) in anhydrous $CH_2Cl_2$ (20 mL) for 3 h, After evaporation of all volatils, a flash column give deprotected mixture of compounds (Z/E; 1/1) (1.11 g, 1.52 mmol, 97%) which are isolated by second chromatographic column ($CH_2Cl_2$/MeOH). Pure diastereoisomer Z (compound 5): $^1$H NMR (400 MHz, $(CD_3)_2CO$) δ 5.82 (q, J=8.1 Hz, 3H, H$^{3'}$, NH$_2$), 5.65 (m, 4H, H$^{2'}$, NH$_2$), 5.22 (s, 1H, H$^5$), 4.88 (sept., J=6.1 Hz, 2H, CH—CH$_3$ POC), 4.78 (d, J=4.1 Hz, 2H, CH$_2$—ODAPY), 4.72 (d, J=2.3 Hz, 2H, CH$_2$—OAc), 4.12 (m, 2H, CH$_2$-c), 3.49 (t, J=6.2 Hz, 2H, CH$_2$-a), 3.41 (t, J=6.4 Hz, 2H, CH$_2$—O), 2.90 (dd, J=23.4, 8.0 Hz, 2H, CH$_2$—P), 2.03 (s, 3H, CH$_3$Ac), 1.88 (m, 2H, CH$_2$-b), 1.56 (m, 2H, CH$_2$—CH$_2$—O), 1.31 (m, 33H, CH$_2$, CH$_3$ POC), 0.87 (m, 3H, CH$_3$). $^{13}$C NMR (101 MHz, $(CD_3)_2CO$) δ 170.41 (C$^6$), 169.83 (C=O OAc), 153.19 (C=O POC), 135.31 (C$^{3'}$), 122.90 (d, J=11.1 Hz, C$^{2'}$), 84.40 (d, J=5.6 Hz, O—CH$_2$—O), 77.12 (C$^5$), 72.58 (C$^{CH\ POC}$), 70.60 (CH$_2$—O), 66.45 (C$^{1'}$), 65.20 (CH$_2$-a), 63.02 (d, J=7.0 Hz, CH$_2$-c), 59.28 (CH$_2$—OAc), 31.73 (CH$_2$), 30.68 (d, J=6.1 Hz, CH$_2$-b), 29.65 (CH$_2$), 29.46 (CH$_2$), 29.37 (CH$_2$), 29.17 (CH$_2$), 26.11 (d, J=138.9 Hz, CH$_2$—P), 26.07 (CH$_2$), 22.42 (CH$_2$), 20.92 (CH$_2$), 19.83 (CH$_2$), 13.44 (CH$_3$). $^{31}$P NMR (162 MHz, $(CD_3)_2CO$) δ 26.59. HRMS-ESI (m/z) [M+H]$^+$ calcd for $C_{35}H_{64}N_4O_{10}P$: 731.4359, found: 731.4351.

[(E)-2-[(2,6-diaminopyrimid in-4-yl)oxymethyl]-4-[3-hexadecoxypropoxy (isopropoxycarbonyloxymethoxy)phosphoryl]but-2'-enyl]acetate (13)

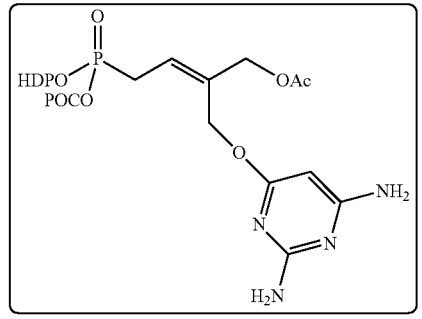

and pure diastereoisomer E (compound 13):
$^1$H NMR (400 MHz, Acetone) δ 5.81 (m, 1H, H$^3$), 5.64 (m, 6H, NH$_2$, O—CH$_2$—O), 5.23 (s, 1H, H$^5$), 4.88 (sept., J=6.1 Hz, 2H, CH—CH$_3$ POC), 4.84 (d, J=2.5 Hz, 2H, CH$_2$—ODAPY), 4.62 (d, J=4.3 Hz, 2H, CH$_2$—OAc), 4.12 (m, 2H, CH$_2$-c), 3.48 (t, J=6.2 Hz, 2H, CH$_2$-a), 3.39 (t, J=6.4 Hz, 2H, CH$_2$—O), 2.93 (dd, J=23.4, 8.0 Hz, 2H, CH$_2$—P), 2.01 (s, 3H, CH$_3$Ac), 1.88 (m, 2H, CH$_2$-b), 1.55 (m, 2H, CH$_2$—CH$_2$—O), 1.31 (m, 33H, CH$_2$, CH$_3$ POC), 0.87 (m, 3H, CH$_3$).
$^{13}$C NMR (101 MHz, Acetone) δ 170.41 (C$^6$/C=O), 169.83 (C$^6$/C=O), 166.18 (C$^4$/C$^2$), 162.98 (C$^4$/C$^2$), 153.19 (C=O POC), 135.60 (d, J=14.5 Hz, C$^3$), 121.47 (d, J=11.3 Hz, C$^2$), 84.43 (d, J=6.0 Hz, O—CH$_2$—O), 77.09 (C$^5$), 72.60 (C$^{CH\ POC}$), 70.62 (CH$_2$—O), 66.24 (C$^1$), 65.34 (CH$_2$-a), 63.04 (d, J=7.0 Hz, CH$_2$-c), 60.17 (CH$_2$—OAc), 59.31 (CH$_2$—OAc), 31.75 (CH$_2$), 30.69 (d, J=6.0 Hz, CH$_2$-b), 29.52 (CH$_2$), 29.48 (CH$_2$), 29.39 (CH$_2$), 29.18 (CH$_2$), 26.24 (d, J=138.9 Hz, CH$_2$—P), 26.08 (CH$_2$), 22.44 (CH$_2$), 20.95 (CH$_2$), 19.88 (CH$_2$), 13.48 (CH$_3$). $^{31}$P NMR (162 MHz, Acetone) δ 26.72
HRMS-ESI (m/z) [M+H]$^+$ calcd for $C_{35}H_{64}N_4O_{10}P$: 731.4359, found: 731.4351.

Example 6: Preparation of compound (6)

[(Z)-4-[bis(isopropoxycarbonyloxymethoxy)phosphoryl]-2-[(2,6-diaminopyrimidin-4-yl)oxymethyl]but-2-enyl]acetate (213)

Chemical Formula: $C_{21}H_{33}N_4O_{12}P$
Molecular Weight: 564.4848

Starting from 205 (198 mg, 2 eq., 0.56 mmol), the general procedure cross metathesis was applied with compound 200 (180 mg, 1 eq., 0.28 mmol) and 15 mol % RuCl$_2$PCy$_3$IMesBenzylidene ruthenium catalyst (36 mg, added in 3 equal portions of 5 mol %) in freshly distilled CH$_2$Cl$_2$ (5 mL). The pure product was not isolated and engaged in the next step after a simple filtration on silica gel, using PE/AcOEt 75/25 as eluting system. General procedure 4 was used with intermediar compound (62 mg, 1 eq., 0.06 mmol), TFA (0.45 mL, 100 eq., 0.6 mmol) in CH$_2$Cl$_2$ (0.9 mL) for 1 h, giving deprotected compound 213 (or compound (6)) as a colorless oil. (31 mg, 18%, E/Z 1:1) Pure diastereoisomer Z: $^1$H NMR (400 MHz, (CD$_3$)$_2$CO) δ 5.67 (m, 9H, CH=CH$_2$, O—CH$_2$—O, NH$_2$), 5.27 (s, 1H, H$^5$), 4.94 (sept, J=6.7 Hz 2H, CH—O), 4.77 (d, J=4.6 Hz, 2H, CH$_2$—ODAPY), 4.72 (d, J=2.2 Hz, 2H, CH$_2$—OAc), 2.97 (dd, J=23.3, 8.0 Hz, 2H, CH$_2$—P), 2.02 (s, 3H, CH$_3$ OAc), 1.31 (d, J=6.2 Hz, 12H, CH$_3$ POC). $^{13}$C NMR (101 MHz, (CD$_3$)$_2$CO) δ 170.49 (C$^6$), 169.96 (C=O OAc), 165.80 (C$^4$), 162.63 (C$^2$), 153.12 (C=O POC), 136.16 (d, J=14.7 Hz, C$^3$), 120.69 (d, J=11.6 Hz, C$^{2'}$), 84.18 (d, J=6.2 Hz, O—CH$_2$—O), 77.11 (C$^5$), 72.77 (C$^{CH\ POC}$), 66.29 (d, J=2.5 Hz, C$^{1'}$), 59.27 (d, J=2.1 Hz, CH$_2$—OAc), 26.46 (d, J=139.4 Hz, CH$_2$—P), 20.92 (CH$_3$ POC), 19.83 (CH$_3$Ac) $^{31}$P NMR (162 MHz, (CD$_3$)$_2$CO) δ 26.51 HRMS-ESI (m/z) [M+H]$^+$ calcd for C$_{21}$H$_{34}$N$_4$O$_{12}$P: 565.1911, found: 565.1904.

Example 7: Preparation of Compound (7)

[(E/Z)-2-[[2-[bis(tert-butoxycarbonyl)amino]-6-methoxy-pyrimidin-4-yl]oxymethyl]-4-[3-hexadecoxypropoxy(isopropoxycarbonyloxymethoxy)phosphoryl]but-2'-enyl]acetate (241)

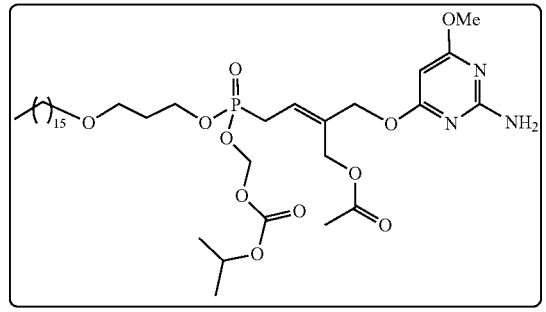

Chemical Formula: C$_{22}$H$_{36}$N$_3$O$_{11}$P
Molecular Weight: 745.89

Starting from 210 (358 mg, 2 eq., 0.69 mmol), the general procedure 3 was applied on compound 235 (156 mg, 1 eq., 0.34 mmol) and 21 mol % RuCl$_2$PCy$_3$IMesBenzylidene ruthenium catalyst (43 mg, 0.051 mmol, added in 3 equal portions of 7 mol %) in freshly distilled CH$_2$Cl$_2$ (7 mL). The crude mixture was not isolated and engaged in the next step after a simple filtration on silica gel, using PE/EtOAc 8/2 as eluting system. General procedure 4 was used on the intermediar compound (130 mg, 1 eq., 0.14 mmol) and TFA (1.05 mL, 100 eq., 13.7 mmol) in CH$_2$Cl$_2$ (2.1 mL) for 2 h, giving deprotected compound 241 (or compound (7)) as a white solid. (E/Z 50/50, 48 mg, 26%) $^1$H NMR (400 MHz, (CD$_3$)$_2$CO) δ 5.93 (bs, 1H, NH), 5.85 (bs, 1H, NH), 5.74 (m, 1H, H$^{3'}$), 5.63 (m, 2H, O—CH$_2$—O), 5.34 (2xs, 1H, H$^5$), 4.87 (sept., J=2.5 Hz, 2H, CH—CH$_3$ POC), 4.86 (m, 2H, H$^{1'}$/CH$_2$—OAc), 4.77 (d, J=4.5 Hz, 2H, H$^{1'}$/CH$_2$—OAc), 4.68 (d, J=2.3 Hz, 2H, H$^{1'}$/CH$_2$—OAc), 4.59 (d, J=4.2 Hz, 2H, H$^{1'}$/CH$_2$—OAc), 4.09 (m, 2H, CH$_2$-c), 3.75 (2xs, 3H, CH$_3$—O), 3.45 (2xt, J=5.2 Hz, 2H, CH$_2$-a), 3.36 (2xt, J=6.4 Hz, 2H, CH$_2$—O HDP), 2.92 (m, 2H, CH$_2$—P), 1.98 (s, 3H, CH$_3$Ac), 1.84 (2xsept, J=6.5 Hz, 2H, CH$_2$-b), 1.49 (m, 2H, CH$_2$, CH$_2$—CH$_2$—O), 1.31 (m, 33H, CH$_2$, CH$_3$ POC), 0.87 (m, 3H, CH$_3$). $^{13}$C NMR (101 MHz, (CD$_3$)$_2$CO) δ 172.30 (C=O), 171.37 (2×C$^6$), 169.77 (2×C$^4$/C$^2$), 162.94 (2×C$^4$/C$^2$), 153.17 (C=O POC), 135.21 (2×d, J=14.4 Hz, C$^{3'}$), 121.96 (2×d, J=11.5 Hz, C$^{3'}$), 84.42 (2×d, J=6.0 Hz, O—CH$_2$—O), 79.19 (2×C$^5$), 77.09 (C$^{quat}$), 72.58 (2×C$^{CH}$ POC), 71.25 (CH$_2$—O HDP), 66.86 (2×C$^{1'}$/CH$_2$OAc), 66.41 (CH$_2$-a), 65.29 (2×C$^{1'}$/CH$_2$OAc), 63.06 (2×d, J=7.6 Hz, CH$_2$-c), 60.81 (2×C$^{1'}$/CH$_2$OAc), 59.27 (2×C$^{1'}$/CH$_2$OAc), 52.64 (CH$_3$—O), 31.73 (CH$_2$), 30.68 (2×d, J=6.2 Hz, CH$_2$-b), 29.64 (CH$_2$), 29.49 (CH$_2$), 29.35 (CH$_2$), 29.16 (CH$_2$), 26.06 (CH$_2$—P), 22.41 (CH$_2$), 20.92 (CH$_2$), 19.84 (2×CH$_2$), 13.44 (CH$_3$). $^{31}$P NMR (162 MHz, (CD3)2CO) δ 26.52, 26.26. HRMS-ESI (m/z) [M+H]$^+$ calcd for C$_{38}$H$_{68}$N$_4$O$_{10}$P: 746.4351, found: 746.4348.

Example 8: Preparation of Compound (8)

[(E/Z)-2'-[(2-amino-6-chloro-pyrimidin-4-yl)oxymethyl]-4-[3-hexadecoxypropoxy(isopropoxycarbonyloxymethoxy)phosphoryl]but-2'-enyl]acetate (242)

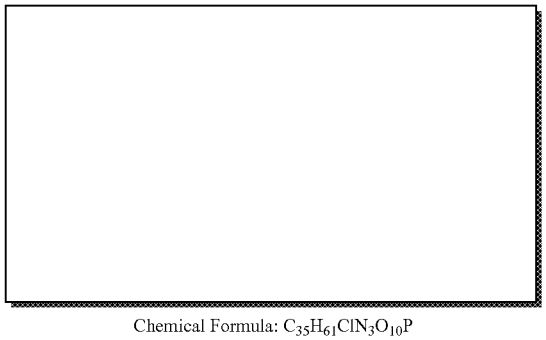

Chemical Formula: C$_{35}$H$_{61}$ClN$_3$O$_{10}$P
Molecular Weight: 750.31

Starting from 210 (954 mg, 2 eq., 1.83 mmol), the general procedure 3 was applied on compound 236 (420 mg, 1 eq., 0.92 mmol) and 21 mol % RuCl$_2$PCy$_3$IMesBenzylidene ruthenium catalyst (117 mg, 0.138 mmol, added in 3 equal portions of 7 mol %) in freshly distilled CH$_2$Cl$_2$ (18 mL, 0.1 M). The crude mixture was not isolated and engaged in the next step after a simple filtration on silica gel, using PE/EtOAc 8/2 as eluting system. General procedure 4 was used on the intermediar compound (405 mg, 1 eq., 0.43 mmol) and TFA (3.26 mL, 100 eq., 42.6 mmol) in CH$_2$Cl$_2$ (6.5 mL) for 2 h, giving deprotected compound 242 (or compound (8)) as a colorless oil. (E/Z 45:55, 289 mg, 42%)
Diastereoisomer Mixture:
$^1$H NMR (400 MHz, (CD$_3$)$_2$CO) δ 6.09 (2xs, 1H, H$^5$), 5.81 (2xq, J=2.5 Hz, 1H, H$^3$), 5.63 (m, 2H, O—CH$_2$—O), 5.42 (bs, 1H, NH), 5.19 (bs, 1H, NH), 4.92 (sept., J=2.5 Hz, 2H, CH—CH$_3$ POC), 4.88 (t, J=3.4 Hz, 2H, CH$_2$—O), 4.81 (d, J=2.2 Hz, 2H, CH$_2$—O), 4.68 (d, J=3.9 Hz, 2H, CH$_2$—O), 4.62 (d, J=4.3 Hz, 2H, CH$_2$—O), 4.14 (m, 2H, CH$_2$-c), 3.45 (2xt, J=6.4 Hz, 2H, CH$_2$-a), 3.35 (2xt, J=6.6 Hz, 2H, CH$_2$-0), 2.92 (m, 2H, CH$_2$—P), 2.05 (2xs, 3H, CH$_3$Ac), 1.90 (m, 2H, CH$_2$-b), 1.54 (m, 2H, CH$_2$, CH$_2$—CH$_2$—O), 1.31 (m, 33H, CH$_2$, CH$_3$ POC), 0.87 (m, 3H, CH$_3$). $^{13}$C NMR (101 MHz, (CD$_3$)$_2$CO) δ 170.64 (2×C$^6$/C=O), 170.43 (2×C$^6$/C=O), 162.16 (2×C$^4$/C$^2$), 160.93 (2×C$^4$/C$^2$), 153.23 (C=O POC), 134.12 (2×d, J=14.7 Hz, C$^2$), 122.30 (2×d, J=11.5 Hz, C$^3$), 97.15 (2×C$^5$), 84.42 (2×d, J=5.3 Hz, O—CH$_2$—O), 77.09 (C $^{quat}$), 73.22 (2×C$^{CH\ POC}$), 71.25 (CH$_2$—O HDP), 68.17 (2×C$^{1'}$/CH$_2$OAc), 66.41 (CH$_2$-a), 65.70 (2×C$^{1'}$/CH$_2$OAc), 63.59 (2×d, J=7.6 Hz, CH$_2$-c), 60.17 (2×C$^{1'}$/CH$_2$OAc), 59.31 (2×C$^{1'}$/CH$_2$OAc), 31.92 (CH$_2$), 30.70 (2×d, J=6.2 Hz, CH$_2$-b), 29.71 (CH$_2$), 29.69 (CH$_2$), 29.65 (CH$_2$), 29.61 (CH$_2$), 29.35 (CH$_2$), 26.62 (2×d, J=140.8 Hz, CH$_2$—P), 26.16 (CH$_2$), 22.68 (CH$_2$), 21.64 (CH$_2$), 20.79 (2×CH$_2$), 14.11 (CH$_3$). $^{31}$P NMR (162 MHz, (CD$_3$)$_2$CO) δ 26.87, 26.59. HRMS-ESI (m/z) [M+H]$^+$ calcd for C$_{35}$H$_{62}$N$_3$O$_{10}$P: 750.3868, found: 750.3856.

Preparation of [(E)-4-(2,6-diaminopyrimidin-4-yl)oxybut-2'-enyl]-(3-hexadecoxypropoxy)phosphinic acid

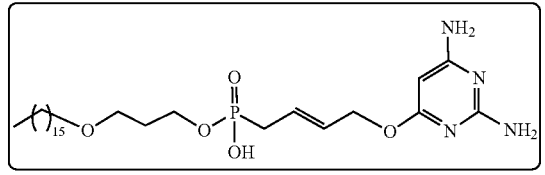

Chemical Formula: C$_{27}$H$_{51}$N$_4$O$_5$P
Molecular Weight: 542.70

Compound 258 (or compound (2))(40 mg, 1 eq., 0.06 mmol) was added to a 0.1 M NaOH solution in ELGA® water (6 mL, 0.01M). This mixture was acidified by the addition of HCl 0.1M, followed by the removal of the volatiles under reduced pressure. The residue is currently being purified by high performance liquid chromatography.
HRMS-ESI (m/z) [M+H]$^+$ calcd for C$_{27}$H$_{51}$N$_4$O$_5$P 543.3675, found 543.3667.

Example 9

Preparation of [(E/Z)-2-[[2-amino-6-(cyclopropylamino)pyrimidin-4-yl]oxymethyl]-4-[3-hexadecoxypropoxy(isopropoxycarbonyl-oxymethoxy)phosphoryl]but-2'-enyl]acetate (240)

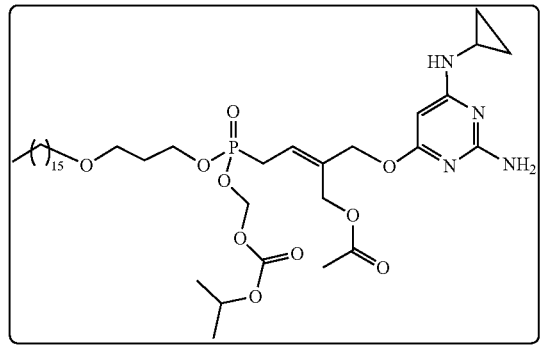

Chemical Formula: C$_{24}$H$_{39}$N$_4$O$_{10}$P
Molecular Weight: 770.95

Starting from 210 (108 mg, 2 eq., 0.21 mmol), the general procedure 3 was applied on compound 234 (60 mg, 1 eq., 0.10 mmol) and 21 mol % RuCl$_2$PCy$_3$IMesBenzylidene ruthenium catalyst (19.5 mg, 0.021 mmol, added in 3 equal portions of 7 mol %) in freshly distilled CH$_2$Cl$_2$ (3 mL). The crude mixture was not isolated and engaged in the next step after a simple filtration on silica gel, using PE/EtOAc 7/3 as eluting system. General procedure 4 was employed on the intermediar compound (22 mg, 1 eq., 0.021 mmol) and TFA (157 μL, 100 eq., 2.05 mmol) in CH$_2$Cl$_2$ (300 μL) for 2 h, giving deprotected compound 240 as a white solid. The residue is currently being purified by high performance liquid chromatography.
HRMS-ESI (m/z) [M+H]$^+$ calcd for C$_{38}$H$_{68}$N$_4$O$_{10}$P: 771.4673, found: 771.4670.

Example 10: Preparation of Compound (11)

[[(E)-4-[2,6-bis[bis(tert-butoxycarbonyl)amino]pyrimidin-4-yl]oxy-3-methyl-but-2'-enyl]-(2,2-dimethylpropanoyloxymethoxy)phosphoryl]oxymethyl 2,2-dimethylpropanoate (286)

Chemical Formula: C$_{41}$H$_{67}$N$_4$O$_{16}$P
Molecular Weight: 902.97

Following the general procedure 3 from compound 285 (497 mg, 2 eq., 0.86 mmol) with allyl-bis(POM)phosphonate (150 mg, 1 eq., 0.43 mmol) and 15 mol % RuCl$_2$PCy$_3$IMesBenzylidene ruthenium catalyst (60 mg, 0.06 mmol, added in 3 equal portions of 5 mol %) in freshly distilled CH$_2$Cl$_2$ (7 mL), compound 286 (156 mg, 40%) was isolated as a light brown oil after purification by flash column chromatography using petroleum ether/EtOAc (8:2) as eluent. $^1$H NMR (400 MHz, CDCl$_3$) δ 6.94 (s, 1H, H$^5$), 5.67 (m, 4H, O—CH$_2$—O), 5.54 (dt, J=7.7, 7.3 Hz, 1H, H$^3$), 4.73 (d, J=4.4 Hz, 2H, CH$_2$—O), 2.72 (dd, J=22.9, 7.7 Hz, 2H, H$^4$), 1.74 (d, J=4.1 Hz, 3H, H$^5$), 1.51 (s, 18H, CH$_3$ Boc), 1.43 (s, 18H, CH$_3$ Boc), 1.23 (s, 18H, CH$_3$ POM). $^{13}$C NMR (101 MHz, CDCl$_3$) δ 176.98 (C=O $^{POM}$), 171.53 (C$^6$), 159.98 (C$^4$), 156.56 (C$^2$), 150.55 (C=O $^{Boc}$), 150.07 (C=O $^{Boc}$), 136.46 (d, J=15.1 Hz, C$^2$), 115.73 (d, J=11.5 Hz, C$^{4'}$), 96.23 (C$^{5'}$), 84.28 (C$^{quat\ Boc}$), 83.21 (C$^{quat\ Boc}$), 81.71 (d, J=6.5 Hz, O—CH$_2$—O), 71.59 (CH$_2$—O), 38.87 (CH$_3$ POM), 27.98 (CH$_3$Boc), 27.87 (CH$_3$Boc), 27.04 (d, J=140.6 Hz, C$^{4'}$), 27.00 (C$^{quat\ POM}$), 14.40 (d, J=2.5 Hz, CH$_3$). $^{31}$P NMR (162 MHz, CDCl$_3$) δ 27.92. HRMS-ESI (m/z) [M+H]$^+$ calcd for C$_{41}$H$_{68}$N$_4$O$_{16}$P 903.4362, found 903.4356.

[[(E)-4-(2,6-diaminopyrimidin-4-yl)oxy-3-methyl-but-2-enyl]-(2,2-dimethyl-propanoyloxymethoxy)phosphoryl]oxymethyl 2,2-dimethylpropanoate (283)

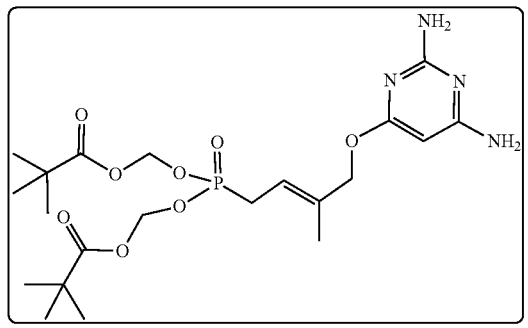

Chemical Formula: $C_{21}H_{35}N_4O_8P$
Molecular Weight: 502.50

General procedure 4 was followed on compound 286 (156 mg, 1 eq., 0.17 mmol), TFA (1.3 mL, 100 eq., 17.28 mmol) in $CH_2Cl_2$ (2.6 mL) for 1 h to give deprotected compound 283 (compound (11))(81 mg, 93%) as a colorless oil after FCC with EtOAc. $^1$H NMR (400 MHz, $(CD_3)_2CO$) δ 7.66 (bs, 2H, $NH_2$), 7.47 (bs, 2H, $NH_2$), 5.61 (m, 4H, O—$CH_2$—O), 5.55 (dt, J=7.7, 6.8 Hz, 1H, $H^3$), 5.49 (s, 1H, $H^5$), 4.75 (d, J=4.3 Hz, 2H, $CH_2$—O), 2.82 (dd, J=23.0, 7.7 Hz, 2H, $CH_2$—P), 1.75 (d, J=4.1 Hz, 3H, $H^5$), 1.22 (s, 18H, $CH_3POM$). $^{13}$C NMR (101 MHz, $(CD_3)_2CO$) δ 177.17 ($C=O^{POM}$), 172.33 ($C^6$), 159.63 ($C^4$), 156.99 ($C^2$), 136.72 (d, J=15.0 Hz, $C^{2'}$), 117.08 (d, J=11.5 Hz, $C^{4'}$), 82.56 (d, J=6.1 Hz, O—$CH_2$—O), 77.68 ($C^5$), 72.23 (d, J=2.6 Hz, $CH_2$—O), 39.27 ($CH_3$ POM), 27.25 (d, J=140.2 Hz, $C^{4'}$), 27.10 ($C^{quat\ POM}$), 14.24 (d, J=2.5 Hz, $CH_3$). $^{31}$P NMR (162 MHz, $(CD_3)_2CO$) δ 27.28. HRMS-ESI (m/z) [M+H]$^+$ calcd for $C_{21}H_{36}N_4O_8P$ 503.2265, found 503.2265.

Example 11: Preparation of Compound (9)

[[(E)-3-[2,6-bis[bis(tert-butoxycarbonyl)amino]pyrimidin-4-yl]oxyprop-1-enyl]-(2,2-dimethylpropanoyloxymethoxy)phosphoryl]oxymethyl 2,2-dimethylpropanoate (249)

Chemical Formula: $C_{39}H_{63}N_4O_{16}P$
Molecular Weight: 874.92

Following the general procedure 3, crotyl-pyrimidine 246 (350 mg, 1 eq., 0.60 mmol) and bis(POM)vinylphosphonate (405 mg, 2 eq., 1.20 mmol) were dissolved in freshly distilled $CH_2Cl_2$ (6 mL, 0.1 M) after which 12 mol % $RuCl_2PCy_3IMesBenzylidene$ ruthenium catalyst (66 mg, 0.06 mmol, added in 3 equal portions of 4 mol %) was added. After evaporation of all volatiles, purification by flash column chromatography using an elution gradient of Petroleum ether/EtOAc (8:2 to 6:4) gave trans-compound 249 as a light brown oil (164 mg, 31%). $^1$H NMR (400 MHz, $CDCl_3$) δ 6.97 (s, 1H, $H^5$), 6.87 (ddt, J=24.2, 17.3, 3.3 Hz, 1H, $H^{2'/3'}$), 6.04 (ddt, J=21.0, 17.3, 1.6 Hz, 1H, $H^{2'/3'}$), 5.61 (m, 4H, O—$CH_2$—O), 4.94 (m, 2H, O—$CH_2$), 1.46 (s, 18H, $CH_3$ Boc), 1.38 (s, 18H, $CH_3$ Boc), 1.16 (s, 18H, $CH_3$ POM). $^{13}$C NMR (101 MHz, $CDCl_3$) δ 176.69 ($C=O^{POM}$), 170.53 ($C^6$), 160.05 ($C^4$), 156.39 ($C^2$), 150.30 ($C=O^{Boc}$), 149.79 ($C=O^{Boc}$), 146.75 (d, J=6.9 Hz, $C^{3'}$), 117.11 (d, J=193.9 Hz, $C^{2'}$), 95.35 ($C^5$), 84.33 ($C^{quat\ Boc}$) 83.23 ($C^{quat\ Boc}$), 81.55 (d, J=5.5 Hz, O—$CH_2$—O), 65.36 (d, J=23.8 Hz, $CH_2$—O), 38.72 ($C^{quat\ POM}$) 27.82 ($CH_3$ Boc), 27.71 ($CH_3$ Boc), 26.83 ($CH_3$). $^{31}$P NMR (162 MHz, $CDCl_3$) δ 17.59. HRMS-ESI (m/z) [M+H]$^+$ calcd for $C_{39}H_{64}N_4O_{16}P$ 875.4049, found 875.4047.

[[(E)-3-(2,6-diaminopyrimidin-4-yl)oxyprop-1-enyl]-(2,2-dimethyl-propanoyloxymethoxy)phosphoryl]oxymethyl 2,2-dimethylpropanoate (254)

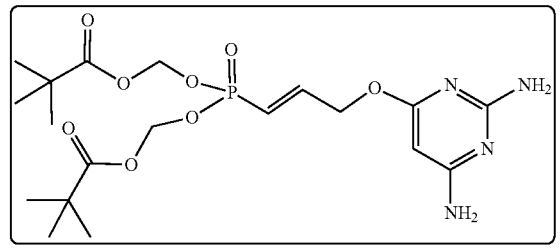

Chemical Formula: $C_{19}H_{31}N_4O_8P$
Molecular Weight: 474.45

Following general procedure 4, trifluoroacetic acid (1.4 mL, 100 eq., 18.6 mmol) and Boc-compound 249 (163 mg, 1 eq., 0.19 mmol) were diluted in $CH_2Cl_2$ (3 mL, 2:1 $CH_2Cl_2$/TFA v/v). Pure compound 254 (or compound (9)) (39 mg, 44%) was obtained after purification by flash column chromatography with EtOAc followed by EtOAc/MeOH (95:5) as eluent. $^1$H NMR (400 MHz, $(CD_3)_2CO$) δ 6.91 (ddt, J=24.0, 17.2, 3.7 Hz, 1H, $H^{2'/3'}$), 6.02 (ddt, J=22.0, 17.2, 2.1 Hz, 1H, $H^{2'/3'}$), 5.67 (m, 4H, O—$CH_2$—O), 5.60 (bs, 2H, $NH_2$), 5.43 (bs, 2H, $NH_2$), 5.28 (s, 1H, $H^5$), 4.94 (dd, J=3.7, 2.1 Hz, 2H, $CH_2$—O), 1.19 (s, 18H, $CH_3$). $^{13}$C NMR (101 MHz, $(CD_3)_2CO$) δ 177.00 ($C=O^{POM}$), 170.79 ($C^6$), 167.48 ($C^4$), 164.12 ($C^2$), 149.99 (J=6.1 Hz, $C^{3'}$), 117.14 (J=190.8 Hz, $C^{2'}$), 82.39 (J=5.4 Hz, O—$CH_2$—O), 77.87 ($C^5$), 64.46 (J=23.6 Hz, $CH_2$—O), 39.26 ($C^{quat\ POM}$), 27.11 ($CH_3$). $^{31}$P NMR (162 MHz, $(CD_3)_2CO$) δ 17.71. HRMS-ESI (m/z) [M+H]$^+$ calcd for $C_{19}H_{32}N_4O_8P$ 475.1952, found 475.1954.

Example 12: Preparation of Compound (10)

[[(E)-5-(2,6-diaminopyrimidin-4-yl)oxypent-3-enyl]-(2,2-dimethyl-propanoyloxymethoxy)phosphoryl]oxymethyl 2,2-dimethylpropanoate (256)

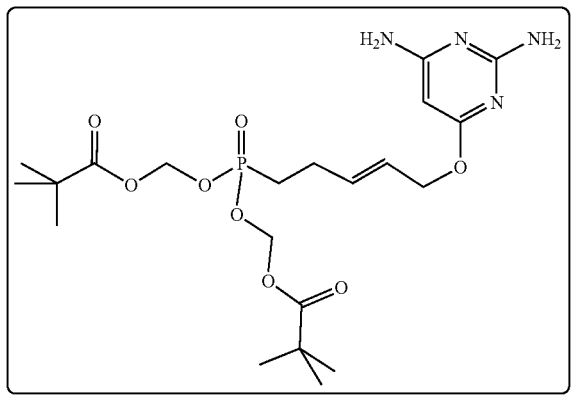

Chemical Formula: $C_{21}H_{35}N_4O_8P$
Molecular Weight: 502.50

Following the general procedure 3 from compound 187 (93 mg, 2 eq., 0.26 mmol) using 246 (75 mg, 1 eq., 0.13 mmol) and 15 mol % $RuCl_2PCy_3IMesBenzylidene$ ruthenium catalyst (18 mg, 0.018 mmol, added in 3 equal portions of 5 mol %) in freshly distilled $CH_2Cl_2$ (1 mL, 0.1 M). The crude compound was not isolated and engaged in the next step after a simple filtration on silica gel, using PE/EtOAc 7/3 as eluting system. General procedure 4 was used on the intermediar compound (47 mg, 1 eq., 0.05 mmol), TFA (0.40 mL, 100 eq., 5.2 mmol) in $CH_2Cl_2$ (0.80 mL) for 1 h to give deprotected compound 256 (or compound (10))(23 mg, 35%) as a colorless oil after FCC with EtOAc to EtOAc/MeOH 95:5. The residue was finally purified on a reverse phase onto HPLC, eluting $AcN/H_2O$ (0 to 100%) $^1H$ NMR (400 MHz, $(CD_3)_2CO$) δ 5.78 (m, 2H, $H^{2'}$, $H^{3'}$), 5.68 (m, 4H, O—$CH_2$—O), 5.48 (bs, 2H, $NH_2$), 5.34 (bs, 2H, $NH_2$), 5.19 (d, J=1.4 Hz, 1H, $H^5$), 4.63 (d, J=5.9 Hz, 2H, $CH_2$—O), 2.35 (m, 2H, $CH_2$, $H^4$), 1.94 (dt, J=19.5, 8.2 Hz, 2H, $H^{5'}$), 1.21 (d, J=1.4 Hz, 18H, $CH_3$-POM). $^{13}C$ NMR (101 MHz, $(CD_3)_2CO$) δ 176.22 (C=O POM), 170.53 ($C^6$), 166.41 ($C^4$), 163.28 ($C^2$), 132.16 (d, J=17.3 Hz, $C^{3'}$), 126.78 (d, J=1.2 Hz, $C^{2'}$), 81.37 (d, J=6.2 Hz, O—$CH_2$—O), 77.03 ($C^5$), 64.86 ($CH_2$—O), 38.37 ($C^{quat\ POM}$), 26.23 ($CH_3^{POM}$), 25.72 (d, J=138.04 Hz, $C^{5'}$), 24.80 (d, J=4.6 Hz, $C^4$) $^{31}P$ NMR (162 MHz, $(CD_3)_2CO$) δ 31.27. HRMS-ESI (m/z) $[M+H]^+$ calcd for $C_{21}H_{36}N_4O_5P$ 503.2270, found 503.2265.

Example 13: Preparation of Compound (12)

Preparation of [5-[2,6-bis(tert-butoxycarbonylamino)pyrimidin-4-yl]pentyl-(2,2-dimethylpropanoyloxymethoxy)phosphoryl]oxymethyl 2,2-dimethylpropanoate (276)

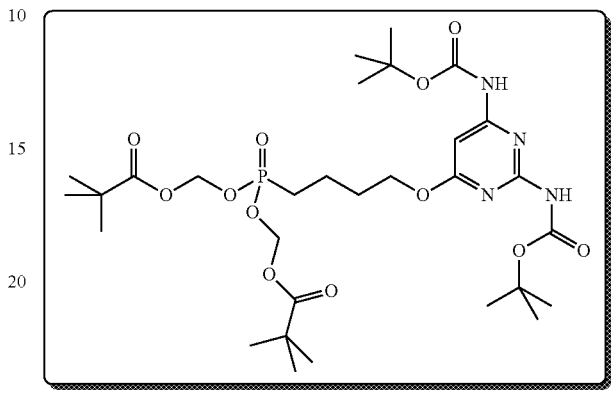

Chemical Formula: $C_{30}H_{51}N_4O_{12}P$
Molecular Weight: 690.73

Compound 250 (125 mg, 1 eq., 0.141 mmol) was diluted with ethyl acetate (4 mL) under $N_2$ atmosphere. The solution was degassed with $N_2$ during 1 min., then the atmosphere was purged with $N_2$ during 5 min. 10% Pd/C (20% w/w, 25 mg) was added slowly in the flask under inert atmosphere. The solution was once more degassed with $N_2$ during 1 min., and the atmosphere for 5 min. in the same conditions. $H_2$ was then introduced into the flask using a balloon, firstly degassing the solution during 1 min., then the atmosphere for 5 min. The outlet was removed, and the mixture was stirred during 20 h at room temperature. The solution and the containing flask were degassed with Arg, and the catalyst was then removed on a pad Celite®, washed with ethyl acetate (3×20 mL), and the volatiles were removed under reduced pressure. The residue was purified by flash column chromatography, (PE/EtOAc 6:4) affording the expected compound 276 as a white solid. (58 mg, 55%) $^1H$ NMR (400 MHz, $CDCl_3$) δ 7.85 (bs, 1H, NH), 7.67 (bs, 1H, NH), 6.91 (s, 1H, $H^5$), 5.68 (s, 2H, O—$CH_2$—O), 5.64 (s, 2H, O—$CH_2$—O), 4.24 (t, J=5.9 Hz, 2H, $H^{1'}$), 1.81 (m, 6H, $H^{2'}$, $H^{3'}$, $H^{4'}$), 1.50 (s, 9H, $CH_3$—BOC), 1.47 (s, 9H, $CH_3$—BOC), 1.22 (s, 21H, $CH_3$POM). $^{13}C$ NMR (101 MHz, $CDCl_3$) δ 176.90 (C=O POM), 171.42 ($C^6$), 159.42 ($C^{quat}$), 156.25 ($C^{quat}$), 151.74 ($C^{quat}$), 150.75 ($C^{quat}$), 87.89 ($C^5$), 81.34 (d, J=6.0 Hz, O—$CH_2$—O), 65.77 ($C^{1'}$), 38.74 ($C^{quatP\ POM}$), 29.44 (d, J=17.0 Hz, $CH_2$), 28.19 ($CH_3$ Boc), 28.11 ($CH_3$ Boc), 26.86 ($CH_3$ POM), 26.14 (d, J=138.4 Hz, $CH_2$—P), 18.86 (d, J=5.3 Hz, $CH_2$). $^{31}P$ NMR (162 MHz, $CDCl_3$) δ 32.75 HRMS-ESI (m/z) $[M+H]^+$ calcd for $C_{30}H_{52}N_4O_{12}P$: 691.3320, found: 691.3311.

Preparation of [5-(2,6-diaminopyrimidin-4-yl)pen-tyl-(2,2-dimethyl-propanoyloxymethoxy)phospho-ryl]oxymethyl 2,2-dimethylpropanoate (275) (Compound (12))

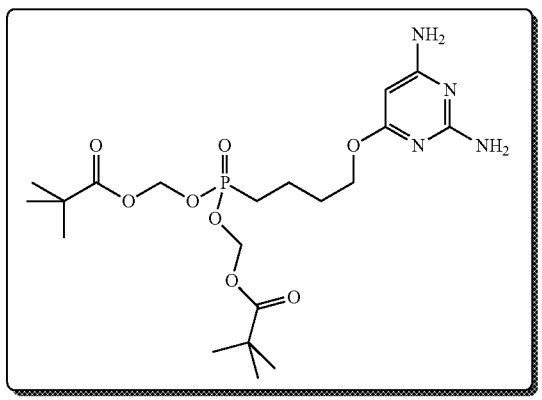

Chemical Formula: $C_{20}H_{35}N_4O_8P$
Molecular Weight: 490.49

General procedure 4 was applied to compound 276 (28 mg, 0.04 mmol) and TFA (0.31 mL, 4.10 mmol) in $CH_2Cl_2$ (0.62 mL) for 1 h to give, after flash column chromatography (DCM/MeOH 95:5), di-deprotected compound 275 as a colorless oil. (16 mg, 83%) $^1$H NMR (400 MHz, MeOD) δ 5.66 (m, 4H, O—$CH_2$—O), 5.23 (s, 1H, $H^5$), 4.13 (t, J=6.0 Hz, 2H, $H^{1'}$), 2.02-1.92 (dt, J=18.0, 7.6 Hz, 2H, $CH_2$—P), 1.81 (m, 2H, $H^{2'}$), 1.73 (m, 2H, $H^{3'}$), 1.23 (d, J=1.6 Hz, 18H, $CH_3$ POM). $^{13}$C NMR (101 MHz, MeOD) δ 176.73 (C=O POM), 170.86 ($C^6$), 166.16 ($C^4/C^2$), 162.66 ($C^4/C^2$), 81.44 (d, J=6.4 Hz, O—$CH_2$—O), 76.02 ($C^{5'}$), 64.98 ($C^{1'}$), 38.34 ($C^{quat\ POM}$), 29.20 (d, J=17.0 Hz, $C^{3'}$), 25.83 ($CH_3$ POM), 25.24 (d, J=140.4 Hz, $CH_2$—P), 18.66 (d, J=5.4 Hz, $C^{2'}$). $^{31}$P NMR (162 MHz, MeOD) δ 33.13 HRMS-ESI (m/z) $[M+H]^+$ calcd for $C_{20}H_{36}N_4O_8P$: 491.2270, found: 491.2265.

Example 14: Preparation of Compound (13)

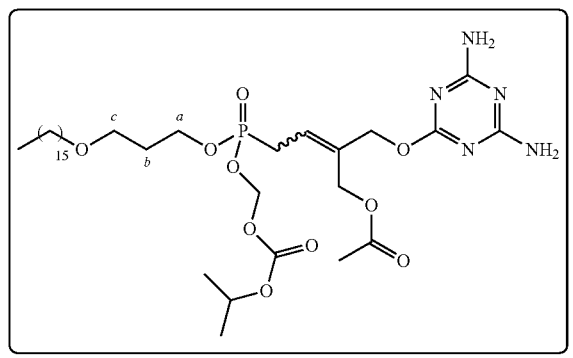

Chemical Formula: $C_{34}H_{62}N_5O_{10}P$
Molecular Weight: 731.87

To a solution of protected triazine 3 (398 mg, 1 eq., 0.62 mmol) and phosphonate (648 mg, 2 eq., 1.24 mmol) in freshly distilled $CH_2Cl_2$ (15 ml), 10 mol % $RuCl_2PCy_3IMesBenzylidene$ ruthenium catalyst (53 mg, added in 5 equal portions of 2 mol %) was added. The mixture was sonicated at 55° C. (80 kHz, 100 VV) under a gentle nitrogen flow. After 3 h, 2 mol % of the ruthenium catalyst was added to the solution. After one night, 2 mol % of the ruthenium catalyst was added to the solution. The reaction was sonicated again for 3 h at 55° C. and then a fourth portion of 2 mol % of the ruthenium catalyst was added. After 3 h, a final portion of 2 mol % of the ruthenium catalyst was added and the mixture was left under sonication for an additional 3 hours and then concentrated to dryness. After evaporation of all volatiles, the pure product was not isolated and engaged in the next step after a simple filtration on silica gel, using PE/AcOEt 75/25 as eluting system.

Trifluoroacetic acid (0.97 mL, 100 eq., 12.63 mmol) was added dropwise to a mixture of Boc-derivative (143 mg, 1 eq., 0.13 mmol) in $CH_2Cl_2$ (2:1 $CH_2Cl_2$/TFA v/v). The reaction was stirred at room temperature for 3 h and then volatiles were removed under reduced pressure. The crude product was extracted with EtOAc, washed with $NaHCO_3$ until pH 7, dried over $MgSO_4$, filtrated and concentrated under vacuum. The crude product was purified by flash column chromatography with DCM/MeOH (97:3) as eluent as eluent affording deprotected compound 14 as a colorless oil (77 mg, 19% for two steps, E/Z 1:1).

Diastereoisomer Mixture (Z/E 50%/50%):
$^1$H NMR (400 MHz, $(CD_3)_2CO$) δ 6.33 (s, 4H, 2$NH_2$), 5.81 (m, 1H, CH=C), 5.67 (m, 2H, O—$CH_2$—O), 4.92 (m, 1H, $CH_3$—CH—$CH_3$, POC), 4.87 (d, J=2.00 Hz, 2H, $CH_2$—ODAPY, E isomer), 4.78 (d, J=2.00 Hz, 2H, $CH_2$—ODAPY, Z isomer), 4.73 (d, J=2.20 Hz, 2H, $CH_2$—OAc, E isomer), 4.64 (d, J=3.60 Hz, 2H, $CH_2$—OAc, Z isomer), 4.14 (m, 2H, $CH_2$-c), 3.48 (q, J=6.20 Hz, 2H, $CH_2$-a), 3.39 (td, J=6.60, 2.70 Hz, 2H, $(CH_2)14$-$CH_2$—O, HDP), 2.86 (dd, J=23.40, 8.00 Hz, 2H, $CH_2$—P), 2.02 (s, 3H, $CH_3$, Ac), 1.88 (m, 2H, $CH_2$-b), 1.52 (m, 2H, $(CH_2)_{13}$—CH2-$CH_2$—O, HDP), 1.29 (m, 32H, $(CH_2)_{13}$, HDP, 2$CH_3$, POC), 0.88 (t, J=6.80 Hz, 3H, $CH_3$, HDP).
$^{13}$C NMR (101 MHz, $(CD_3)_2CO$) δ 171.99 ($C^6$/C=O), 171.00 ($C^6$/C=O), 170.75 ($C^4/C^2$), 169.96 ($C^4/C^2$), 154.16 (C=O, POC), 135.92 (d, J=2.60 Hz, $C^3$), 122.59 (d, J=11.30 Hz, $C^2$), 85.45 (t, J=5.70 Hz, O—$CH_2$—O), 73.60 (d, J=1.80 Hz, $^{CCH\ POC}$) 71.60 ($CH_2$—O), 71.06 ($C^1$), 68.07 (d, J=2.40 Hz, $CH_2$-a), 67.23 (d, J=3.4 Hz), 66.32 (d, J=2.2 Hz), 64.12 (d, J=7.0 Hz), 62.18 (d, J=2.1 Hz), 60.30 (d, J=2.1 Hz), $CH_2$-c, $CH_2$—OAc, $CH_2$—OAc, 32.72 ($CH_2$ aliphatic), 31.65 (dd, J=6.10, 2.00 Hz, $CH_2$-b), 30.96 ($CH_2$ aliphatic), 29.48 ($CH_2$ aliphatic), 29.39 ($CH_2$ aliphatic), 29.18 ($CH_2$ aliphatic), 27.24 (d, J=138.9 Hz, $CH_2$—P), 27.05 ($CH_2$ aliphatic), 23.42 ($CH_2$ aliphatic), 21.93 (d, J=1.30 Hz, $CH_2$ aliphatic), 20.89 (d, J=5.10 Hz, $CH_2$ aliphatic), 14.47 ($CH_3$). HRMS-ESI (m/z) $[M+H]^+$ calcd for $C_{34}H_{63}N_5O_{10}P$ 732.4292, found 732.4307.

Antiviral Activity of the Compounds of the Invention

I—Protocols

1. The antiviral assays, other than the anti-HIV assays, were based on inhibition of virus-induced cytopathicity or plaque formation in HEL [herpes simplex virus 1 (HSV-1) (KOS), HSV-2 (G), vaccinia virus, vesicular stomatitis virus, human cytomegalovirus (HCMV), and varicella-zoster virus (VZV)], Vero (parainfluenza-3, reovirus-1, Sindbis virus and Coxsackie B4), HeLa (vesicular stomatitis virus, Coxsackie virus B4, and respiratory syncytial virus) or MDCK [influenza A (H1N1; H3N2) and influenza B] cell cultures. Confluent cell cultures (or nearly confluent for MDCK cells) in microtiter 96-well plates were inoculated with 100 CCID50 of virus (1 CCID50 being the virus dose to infect 50% of the cell cultures) or with 20 plaque forming units (PFU) (for VZV) in the presence of varying concentrations (100, 20, . . . µM) of the test compounds. Viral cytopathic effect (CPE) or plaque formation (VZV) was recorded as soon as it reached completion in the control virus-infected cell cultures that were not treated with the test compounds. Antiviral activity was expressed as the $EC_{50}$ or compound concentration required reducing virus-induced CPE or viral plaque (VZV) plaque formation by 50%. The minimal cytotoxic concentration (MCC) of the compounds was defined as the compound concentration that caused a microscopically visible alteration of cell morphology. Alternatively, the cytostatic activity of the test compounds was measured based on inhibition of cell growth. HEL cells were seeded at a rate of $5 \times 10^3$ cells/well into 96-well microtiter plates and allowed to proliferate for 24 h. Then, medium containing different concentrations of the test compounds was added. After 3 days of incubation at 37° C., the cell number was determined with a Coulter counter. The cytostatic concentration was calculated as the $CC_{50}$, or the compound concentration required to reduce cell proliferation by 50% relative to the number of cells in the untreated controls.

Cytotoxicity was evaluated in normal PBM cells, along with CEM and Vero cells (L. J. Stuyver, S. Lostia, M. Adams, J. Mathew, B. S. Pai, J. Grier, P. Tharnish, Y. Choi, Y. Chong, H. Choo, C. K. Chu, M. J. Otto, R. F. Schinazi, Antiviral activities and cellular toxicities of modified 2',3'-dideoxy-2',3'-didehydrocytidine analogues, Antimicrob. Agents Chemother. 46 (2002) 3854-3860).

2. Virus Infection (Protocols for: Adeno Virus, Cytomegalo Virus, Poxvirus, Myxo Virus, Equine Herpes Virus)

Cognate permissive cell lines were used for each virus infection assay.

Cells were grown in DMEM without phenol red (Sigma-Aldrich) 10% SVF, Pen-strep, 1× sodium pyruvate, 1× Glutamax.

Virus Infection Protocol

Virus infection was carried out on permissive cells seeded in either in 96 wells plate or in 6 well plates, in duplicate at one or two MOI (multiplicity of infection) and 7 concentrations of LA6.

Day 0: cells seeded at 10 k per well in Corning Glass Bottom 96 well plates in 200 µl of DMEM without phenol red or 200 k in 6 well plates.

Day 1: cells were treated with LA6 (from 1 to 0.0037 µM by two fold dilutions) in duplicate and were infected at different MOI according to the tested virus Day 2 to day 7: cells were fixed with Formalin 10 min at room temperature. Cells were washed with 200 µL PBS and 100 µL PBS/Hoechst® 33342 (1/1000) per well. 96 well plates were kept at 4° C. in the dark until data acquisition Image acquisition and analysis for high content quantification was performed on a Thermo Cellomics Arrayscan™ VTI microscope using a modified compartmental analysis algorithm for fluorescent virus. For unmodified virus, ECP progression or plaque count was determined visually by double blind analysis.

BRIEF DESCRIPTION OF THE DRAWING FIGURES

Figure 3:
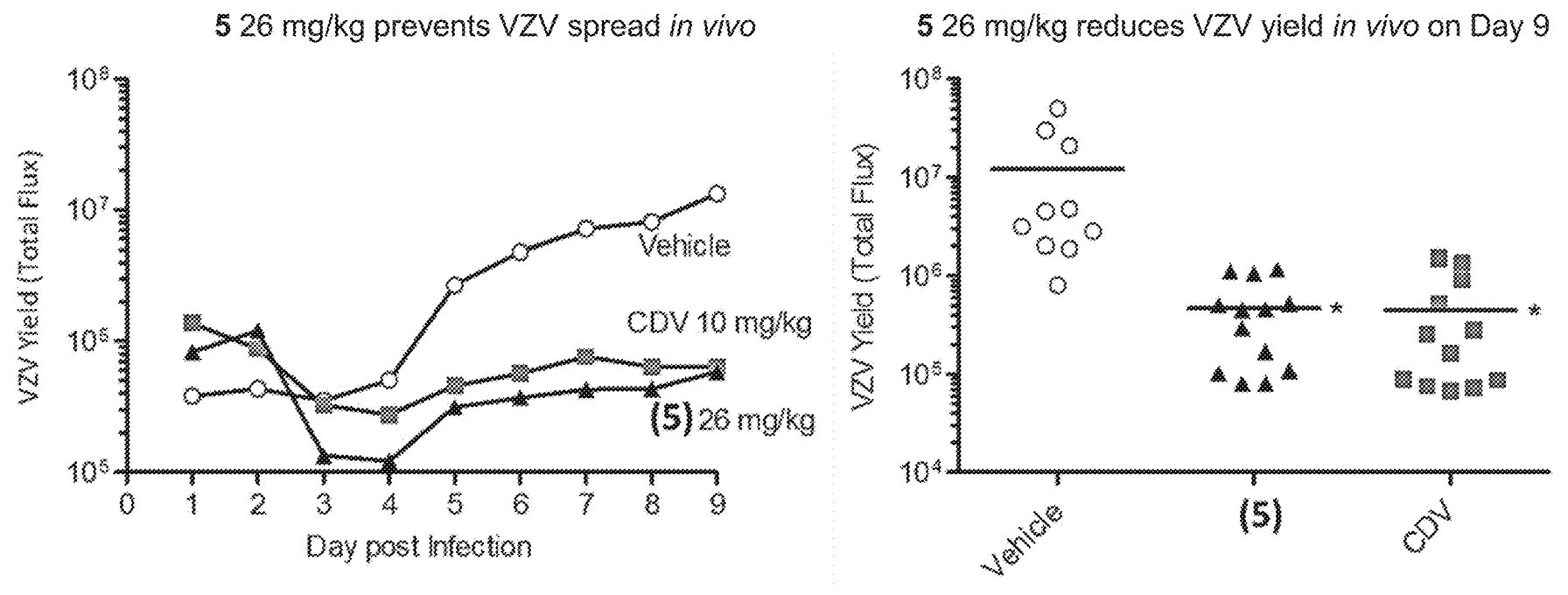

FIG. 3 provides graphic representations of additional testing of compounds in accordance with the claimed invention.

Figure 4:
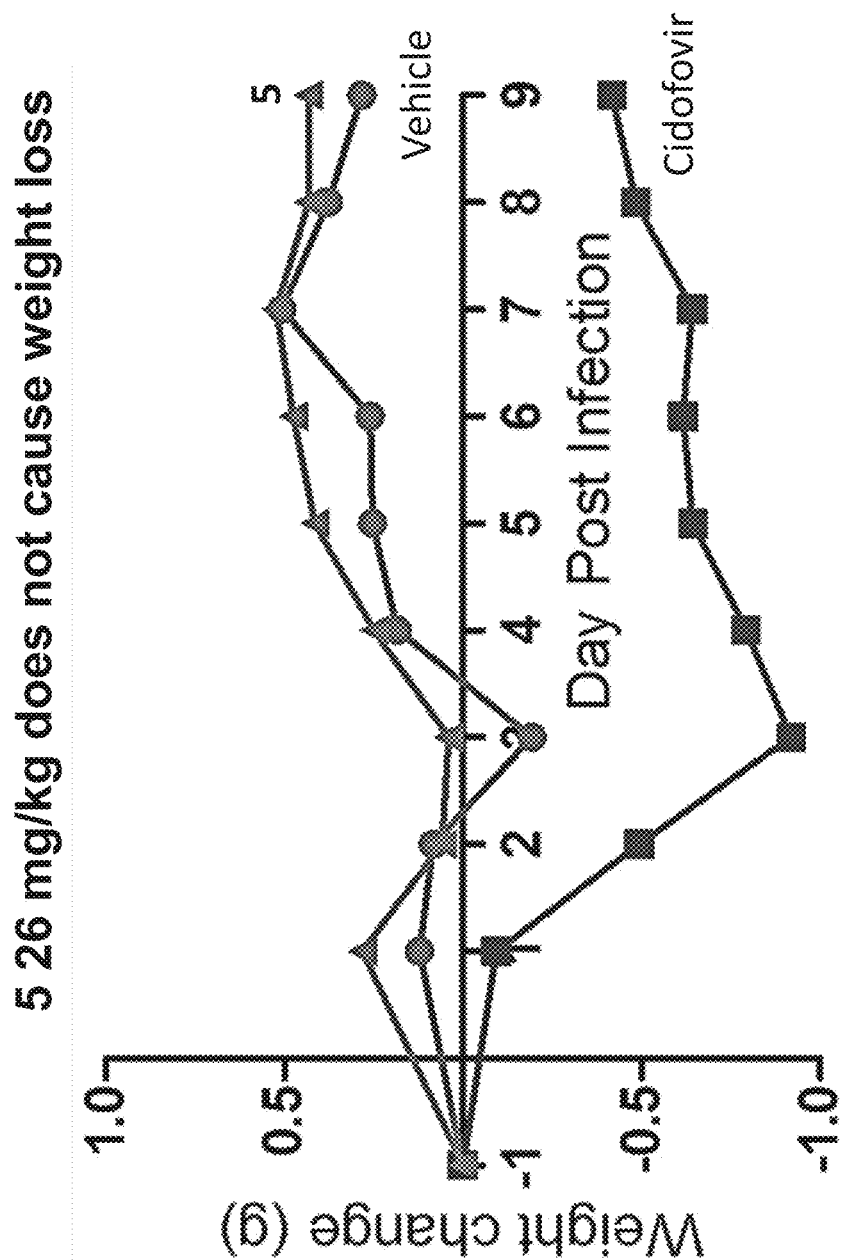

FIG. 4 is a graphic representation of weight change in mice undergoing treatment in accordance with the claimed invention.

Figure 5A:
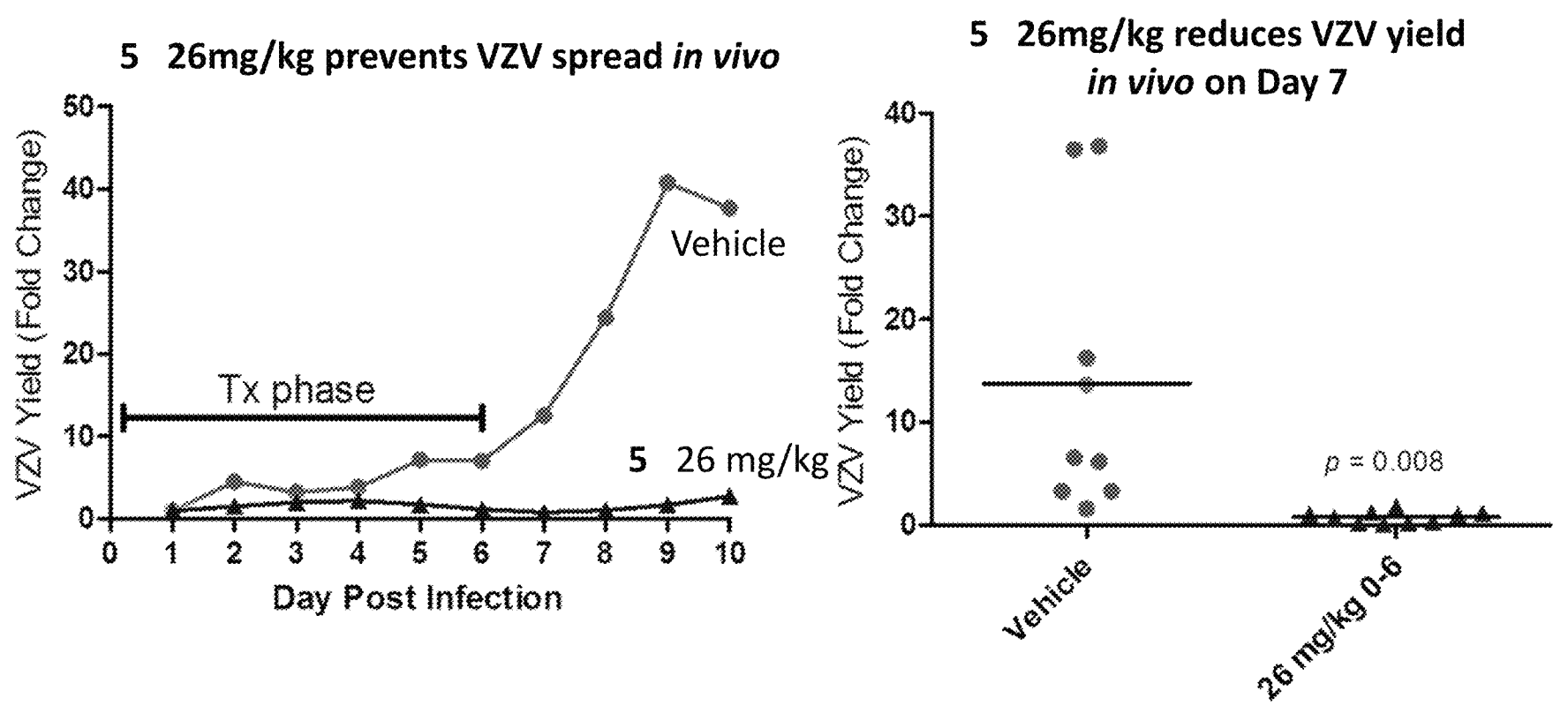

FIG. 5A is a graphic representations of the in vivo evaluation of compounds in accordance with the claimed invention.

Figure 5B:
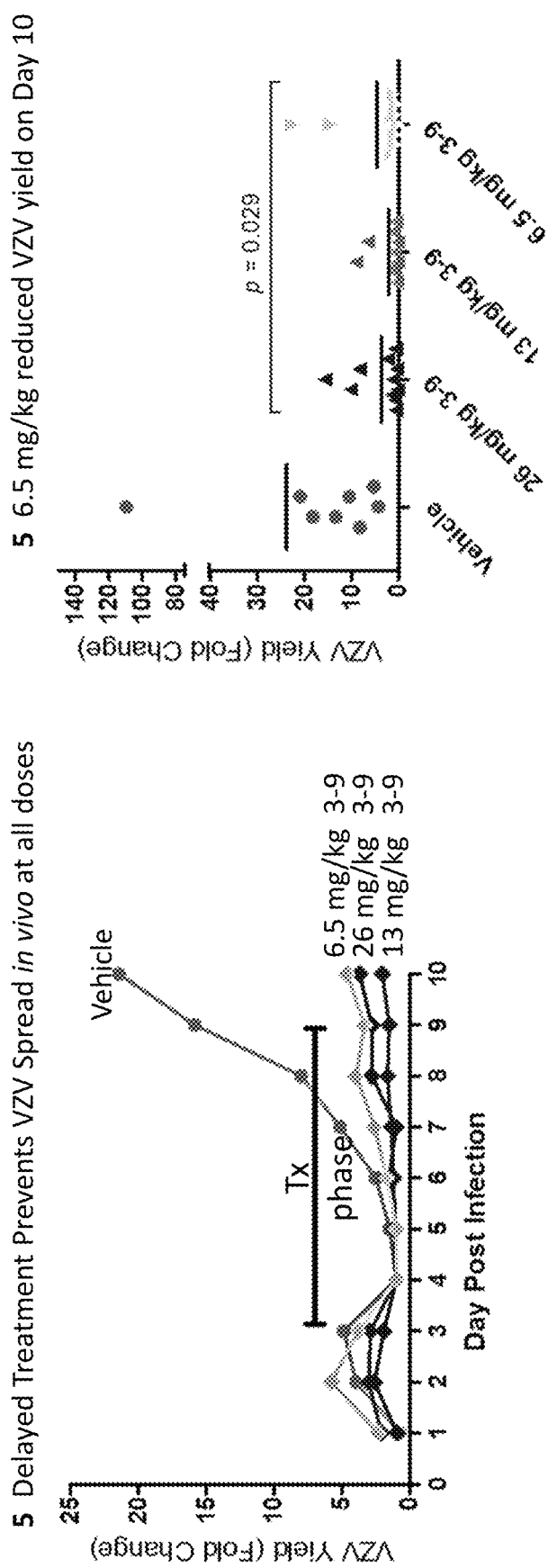

FIG. 5B is a graphic representations of the in vivo evaluation of compounds in accordance with the claimed invention.

Figure 6:
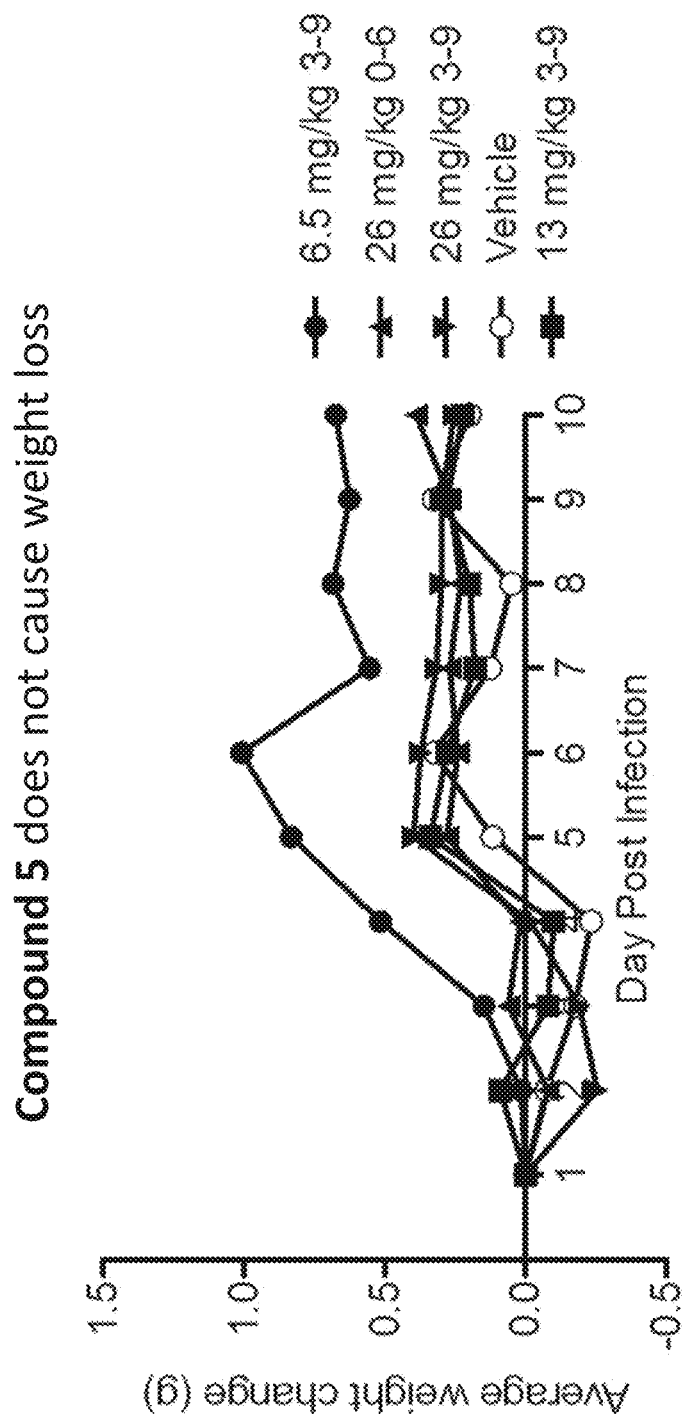

FIG. 6 provides graphic representations of the testing showing that the compounds in accordance with the claimed invention did not cause overt toxicity in test assays of mice.

Figure 7:
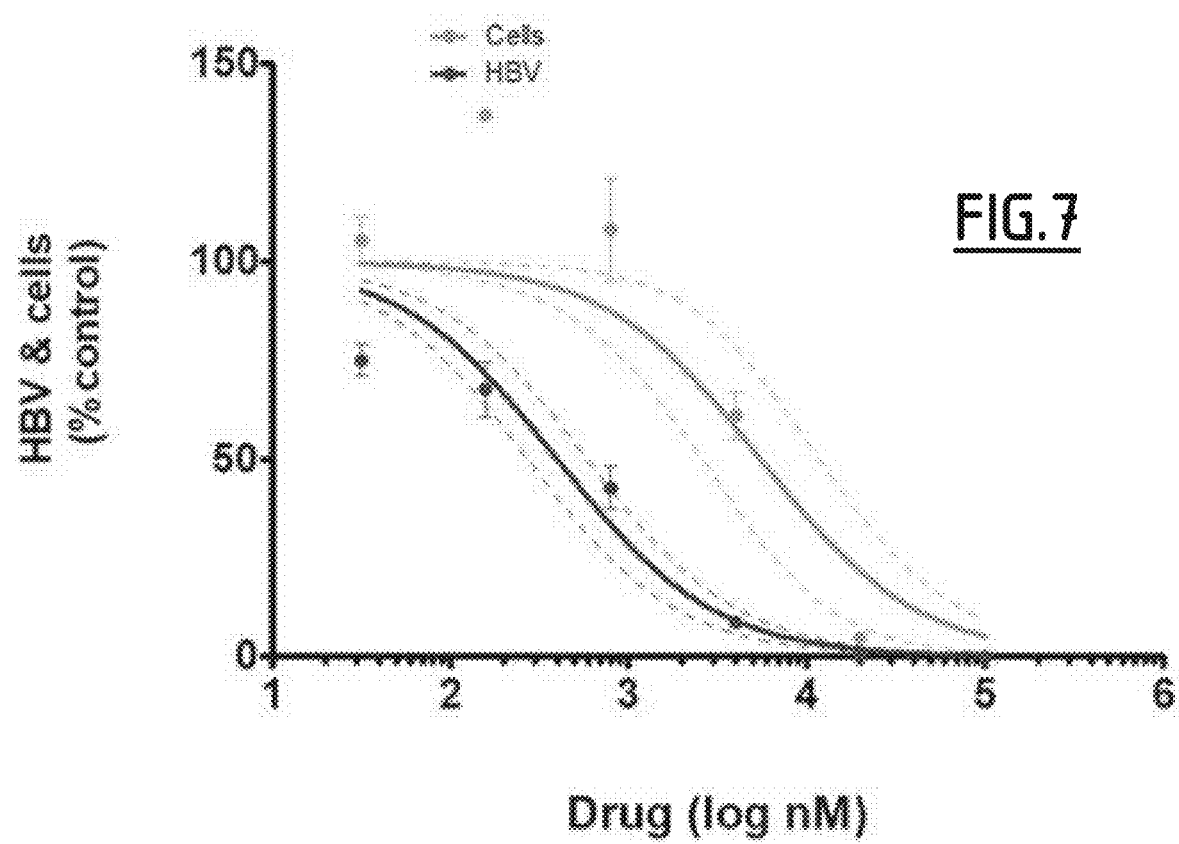

FIG. 7 is a graphic representation of additional testing of compounds in accordance with the claimed invention.

Figure 8:
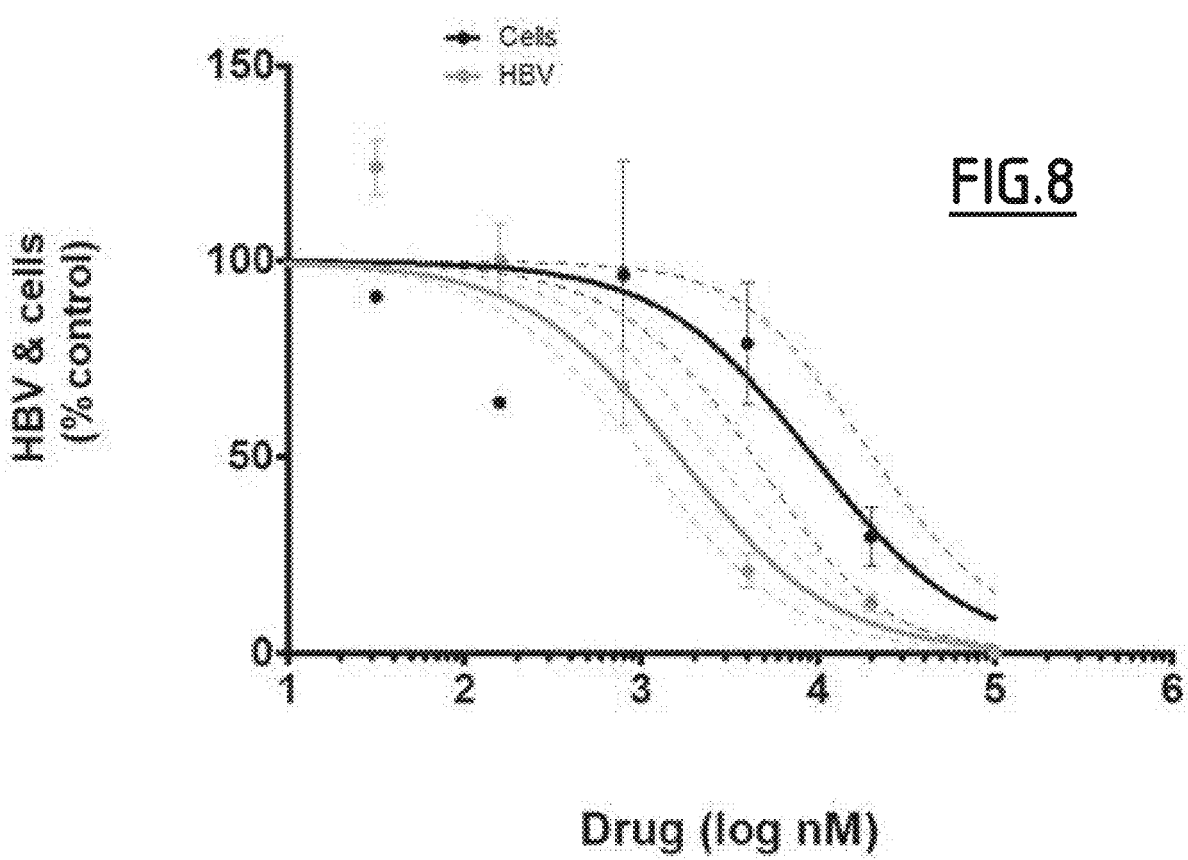

FIG. 8 is a graphic representation of additional testing of compounds in accordance with the claimed invention.

Figure 9:
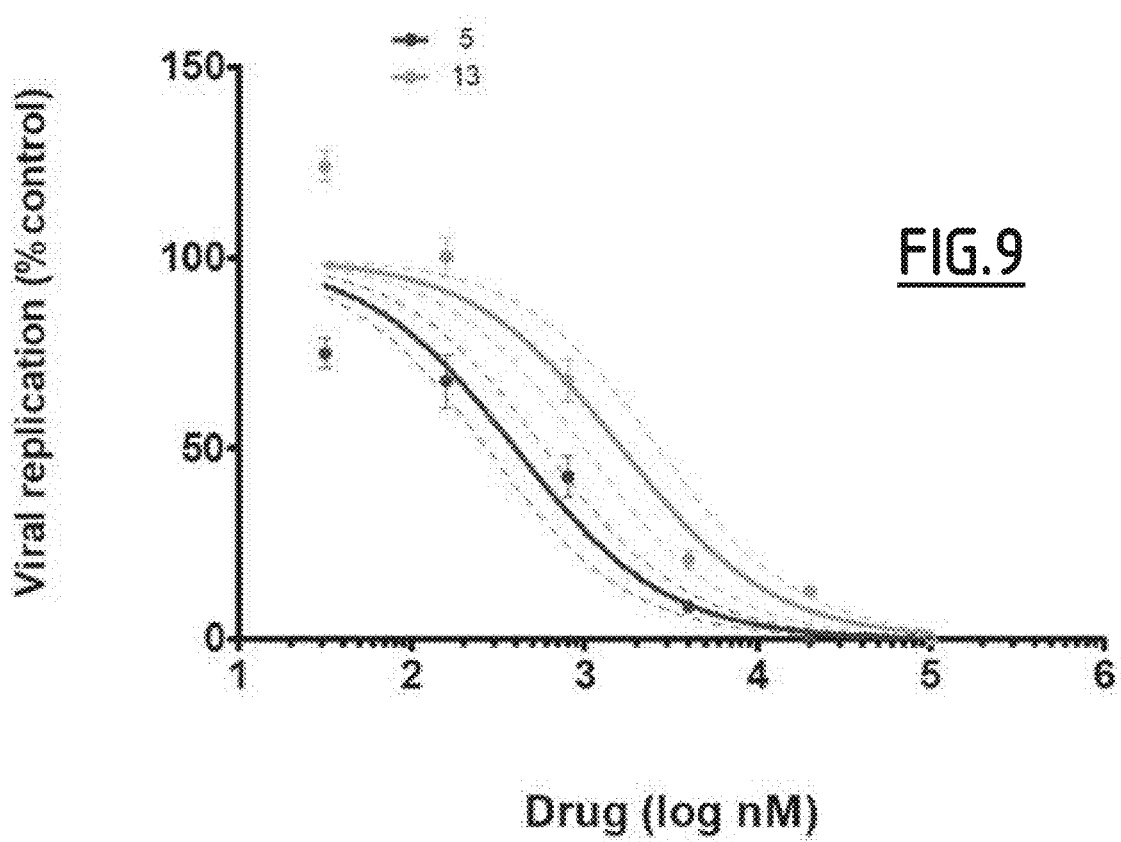

FIG. 9 is a graphic representation of additional testing of compounds in accordance with the claimed invention.

Figure 10:
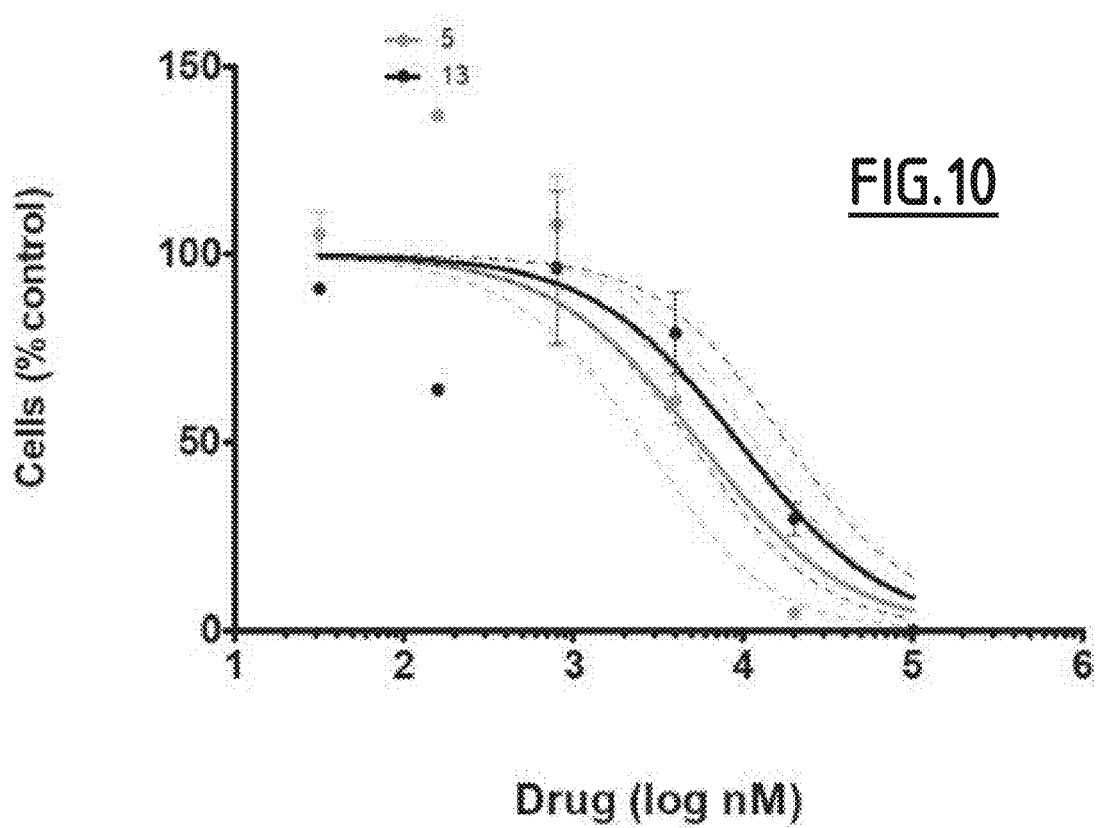

FIG. 10 is a graphic representation of additional testing of compounds in accordance with the claimed invention.

The in vivo evaluation of compound (5) was repeated to confirm its antiviral activity against VZV. In addition, a dose-ranging and delayed treatment assay was included to determine the lowest effective dose (FIG. 5Figures 5A and 5B). As before, 5 26 mg/kg was given once daily, by the subcutaneous route, from Days 0-6. This group was compared to Vehicle (Cremophor-DMSO-saline). In the dose ranging assay, 5 high dose (26 mg/kg), medium dose (13 mg/kg) or low dose (6.5 mg/kg) was given once daily, by the subcutaneous route, from Days 3-9. The treatment phase was delayed to Day 3 because this is more clinically relevant. Again, 5 was effective at 26 mg/kg given at the time of infection, and it prevented VZV spread in skin. Virus yield on Day 7, the day after treatment ended, was significantly less than the Vehicle group (p =0.008, Student's t test). The 26 mg/kg dose was also effective when treatment was delayed to Day 3. The medium and low doses of 5 were equally effective. Virus yield on Day 10, the day after treatment ended for these groups, was significantly less than the Vehicle group (p =0.029, 1-way ANOVA, Dunnett's post hoc test). These results indicate that 5 is highly potent against VZV in this mouse model, effectively preventing VZV spread at a low dose of 6.5 mg/kg.

II—Results

| | EC$_{50}$ (μM)$^a$ | | | | Cytotoxicity (μM) | |
|---|---|---|---|---|---|---|
| | HCMV | | VZV | | | |
| | | | TK+ | TK− | | |
| | (AD-169) | (Davis) | (OKA) | (07/1) | MCC$^b$ | CC$_{50}$$^c$ |
| Acyclovir | 0.4 | 250 | 2.7 | 15.0 ± 1.5 | >100 | 134 ± 10 |
| Brivudine | 0.08 | 250 | 0.01 | 117 | >100 | 339 |
| Cidofovir | 1.2 | 1 | nd | nd | nd | nd |
| Compound (1) | 44.7 | 44.7 | 2.04 | 2.32 | >100 | 5.1 |
| Compound (2) | 7.08 | 7.26 | 0.17 | 0.24 | >100 | 14.49 |
| Compound (3) | 44.72 | 36.57 | 0.86 | 1.25 | >100 | 99 |
| Compound (4) | 8.56 | 4.06 | 0.14 | 0.12 | 100 | 2.02 |
| Compound (5) | 1.79 | 0.70 | 0.0035 | 0.018 | 60 | 0.66 |
| Compound (6) | >20 | 49.70 | 0.089 | 0.22 | >100 | 15.42 |
| Compound (7) | >20 | 8.94 | >20 | >20 | 100 | 1.29 |
| Compound (8) | >20 | 13.11 | 48.9 | >20 | 100 | 5.01 |
| Compound (9) | >100 | >100 | 76.5 | >100 | >100 | ND |
| Compound (10) | >100 | >100 | 34.2 | 24.46 | 100 | ND |
| Compound (11) | >100 | >100 | 51.5 | 49.3 | >100 | ND |
| Compound (12) | 44.72 | >20 | 11.30 | 11.04 | >100 | 54.93 |

$^a$Effective concentration required to reduce virus plaque formation by 50%.
$^b$Minimum cytotoxic concentration that causes a microscopically detectable alteration of cell morphology.
$^c$Cytotoxic concentration required to reduce cell growth by 50%.

Compounds were evaluated for anti-HCMV and anti-VZV activity. Among the synthesized compounds, products 1 to 6 exhibit EC$_{50}$ in micromolar and nanomolar concentration activity. Compound 5 with the mixed prodrug (HDP/POC) is active against HCMV (Davis) with an EC$_{50}$ of 0.7 μM and VZV (TK−) with an EC$_{50}$ of 0.0035 μM and selective Index of 188.

| | EC$_{50}$ (μM)$^a$ | | | | | Cytotoxicity (μM) | |
|---|---|---|---|---|---|---|---|
| | HSV-1 | HSV-2 | HSV-1 (KOS ACV) | Vaccinia | Feline Herpes | | |
| | (KOS) | (G) | TK− | Virus | Virus | MCC$^b$ | CC$_{50}$$^c$ |
| Brivudin | 0.04 | 50 | 50 | 22 | — | >100 | >100 |
| Cidofovir | 4.5 | 1.0 | 2.8 | 112 | — | >100 | >100 |
| Acyclovir | 0.2 | 0.2 | 85 | >100 | — | >100 | >100 |
| Ganciclovir | 0.032 | 0.06 | 8.9 | >100 | 1.4 | >100 | >100 |
| Compound (1) | 13.4 | 13.4 | 13.4 | 32.5 | >100 | >100 | 5.1 |
| Compound (2) | >100 | >100 | >100 | >100 | >100 | >100 | 14.49 |
| Compound (3) | 3.75 | 1.85 | 5.75 | >100 | >100 | >100 | 99 |
| Compound (4) | 0.6 | 1.1 | 0.6 | 2.9 | >100 | 100 | 2.02 |
| Compound (5) | 0.043 ± 0.037 | 0.015 ± 0.05 | 0.008 ± 0.002 | 0.115 ± 0.11 | 0.35 | 60 | 0.66 |
| Compound (6) | 0.6 ± 0.2 | 0.35 ± 0.05 | 0.4 | 4.1 ± 2.4 | >100 | >100 | 15.42 |
| Compound (7) | >100 | >100 | >100 | >100 | >100 | 100 | 1.29 |
| Compound (8) | >100 | >100 | >100 | >100 | >100 | 100 | 5.01 |
| Compound (9) | >100 | >100 | >100 | >100 | >100 | >100 | ND |
| Compound (10) | >100 | >100 | >100 | >100 | >100 | 100 | ND |
| Compound (11) | >100 | >100 | 51.5 | 49.3 | >100 | >100 | ND |
| Compound (12) | 39.5 | 39.5 | 42 | >100 | >100 | >100 | 54.93 |

$^a$Effective concentration required to reduce virus plaque formation by 50%.
$^b$Minimum cytotoxic concentration that causes a microscopically detectable alteration of cell morphology.
$^c$Cytotoxic concentration required to reduce cell growth by 50%.

Synthesized compounds were evaluated for anti HSV-1, anti-HSV-2, anti-HSV-1 (TK−), anti-VV and anti-FHV. Among them numerous compounds (compounds 1, 3, 4, 5 and 6) possess micromolar and sub-micromolar activities against these viruses. Especially compound 5 which showed nanomolar activities (EC$_{50}$<0.35 μM) against both tested viruses.

| | EC$_{50}$ (μM)$^a$ | | | | |
|---|---|---|---|---|---|
| | Equine Herpes V 1 | Equine Herpes V 4 | Vaccinia Virus TK− | Adeno virus | Myxomatosis Virus (MYXV) |
| Compound (5) | <0.125 | <0.125 | <0.03 | <0.037 | 0.051 |

$^a$Effective concentration required to reduce virus plaque formation by 50%.

Compound 5 is active against different families of veterinary viruses such as Equine herpes and Myxomatosis virus with an $EC_{50}$ in nanomolar concentration. Against vaccicnia virus TK- and Adeno virus, compound 5 is also active with $EC_{50}$ concentrations <30 Nm and <37 Nm respectively.

In Vivo Evaluation

Varicella zoster virus (VZV) causes the childhood disease varicella (chicken pox) and establishes lifelong latency in neurons. The virus may reactivate years later and manifest as herpes zoster (shingles). These infections are characterized by vesicular skin lesions. Antiviral therapies should prevent VZV spread in the skin and reduce virus shedding, so we developed human skin models to evaluate compounds for activity against VZV. We evaluated the compound 5, in three assays to evaluate its antiviral activity against VZV. We used a cell-based assay to determine that 5 is effective against a VZV strain that is resistant to acyclovir in the nanomolar range. 5 was effective, although less potent, in a human skin organ culture assay. The major question we addressed was whether 5 was effective in vivo. In fact, it is highly potent and prevents VZV spread in the mouse model.

Methods

Cells: Human retinal pigment epithelium cells were used to cultivate VZV. ARPE-19 cells (ATCC CRL 2302) were grown in Eagle minimum essential medium with Earle's salts and L-glutamine (HyClone Laboratories), supplemented with 10% heat-inactivated fetal bovine serum (Benchmark FBS; Gemini Bio Products), penicillin-streptomycin (5000 IU/mL), amphotericin B (250 Ig/mL), and nonessential amino acids (all Mediatech). Cells were incubated at 37° C. in humidified 5% $CO_2$.

Viruses: VZV-BAC-Luc (Zhang Z, Rowe J, Wang W, Sommer M, Arvin A, Moffat J, Zhu H. 2007. Genetic analysis of varicella-zoster virus ORF0 to ORF4 by use of a novel luciferase bacterial artificial chromosome system. Journal of virology 81:9024-9033), derived from the Parental Oka (POka, Accession number: AB097933) strain was propagated in ARPE-19 cells. The VZV-BAC-Luc TK- strain ($ACV^R$) was isolated by selection in increasing concentrations of acyclovir. Virus was passaged by diluting infected cells 1:100, transferring to uninfected cells, then incubating for 3-5 days. Stocks of VZV-infected cells were frozen in tissue culture medium with 10% DMSO and stored at −80° C. or in liquid nitrogen. Bioluminescence is measured in the IVIS-50 or IVIS-200 instruments, and it is proportional to viral load and pfu. To prepare the virus for inoculation into human skin in culture or in mice, VZV-infected ARPE-19 cells were trypsinized, then washed and resuspended in tissue culture medium, and used immediately for direct injection.

Evaluation of 5 in ARPE-19 cells. ARPE-19 cells were seeded in 24-well plates and incubated overnight. The medium was removed and VZV-infected cells, either the wild type VZV-BAC-Luc or the $ACV^R$ isogenic mutant, were added in 0.5 mL and incubated for 2 h. 0.5 mL of medium containing either vehicle or 2-fold dilutions of 5, acyclovir, or cidofovir at concentrations between 0.00125 and 40.0 µM were added to triplicate samples, and then the plates were incubated for 3 days. VZV spread was measured by bioluminescence imaging and expressed as Total Flux (photons/sec/$cm^2$/steradian). The triplicate values were averaged and compared to the untreated group to determine the extent of inhibition (in percent). The $EC_{50}$ was estimated by interpolation.

Evaluation of 5 in skin organ culture: The skin organ culture model is described in detail elsewhere (Taylor, S. L. and J. F. Moffat (2005). "Replication of varicella-zoster virus in human skin organ culture." *J Virol* 79(17): 11501-115). Human fetal skin was purchased from ABR and delivered by overnight courier on wet ice. The tissue was cleaned, disinfected in betadine and 70% ethanol, then cut into pieces approximately 1-$cm^2$. Each tissue was injected twice with 30 µL of the VZV-infected cell suspension (~$10^3$ pfu) using a 1 cc syringe fitted with a 27-gauge needle attached to a volumetric stepper (Tridak). The needle was lightly dragged across the tissue approximately 5 times to scarify the surface to increase infection. Tissues were incubated at 37° C. for 3 h to allow the virus to adhere, and then placed individually on NetWells (Corning) that had contact with 1.0 mL of tissue culture medium. The next day (Day 1) each piece of skin was soaked in D-luciferin for 45 min, and then scanned in the IVIS-50 instrument to measure Total Flux. The drug treatment began on Day 1 by placing the skin, in NetWells, over medium containing positive control drug cidofovir (5 µM), or 5 at concentrations ranging from 1 nM to 5 µM. Each group contained 6 pieces of skin. The medium and drug were refreshed daily until the final IVIS scan on Day 11. The antiviral effects of 5 were determined by assessing VZV yield compared to the vehicle group.

SCID-Hu mouse model of VZV replication. CB.17 scid/beige male mice (Charles River) were implanted subcutaneously with human fetal skin (the same type of specimens used for the skin organ culture assay). After 3-4 weeks engraftment, the skin implants were inoculated with VZV-BAC-Luc or VZV-ORF57-Luc. The mice were divided into groups (N=10-13) for treatment or controls. The positive control antiviral drug was cidofovir, 10 mg/kg/day given by intraperitoneal injection. The negative control was the vehicle Cremophor-DMSO-saline (1:1:8) given by subcutaneous injection. The treatment groups were 5 in Cremophor-DMSO-saline, 26, 13, or 6.5 mg/kg/day, given by subcutaneous injection. Treatment began 2 hours or 3 days after the inoculation surgery and continued daily or alternating days for up to 9 days. The mice were scanned in the IVIS-200 instrument daily from Day 1-10. The mice were weighed before the start of the study and daily during the treatment phase. The antiviral effects of compound (5) were determined by assessing the VZV yield measured by Total Flux (photons/sec/$cm^2$/steradian).

Statistical analysis: The results were analyzed for statistical significance by Student's t test or by ANOVA and Dunnett's post hoc test of multiple comparisons (GraphPad Prism).

Results

Figure 1:
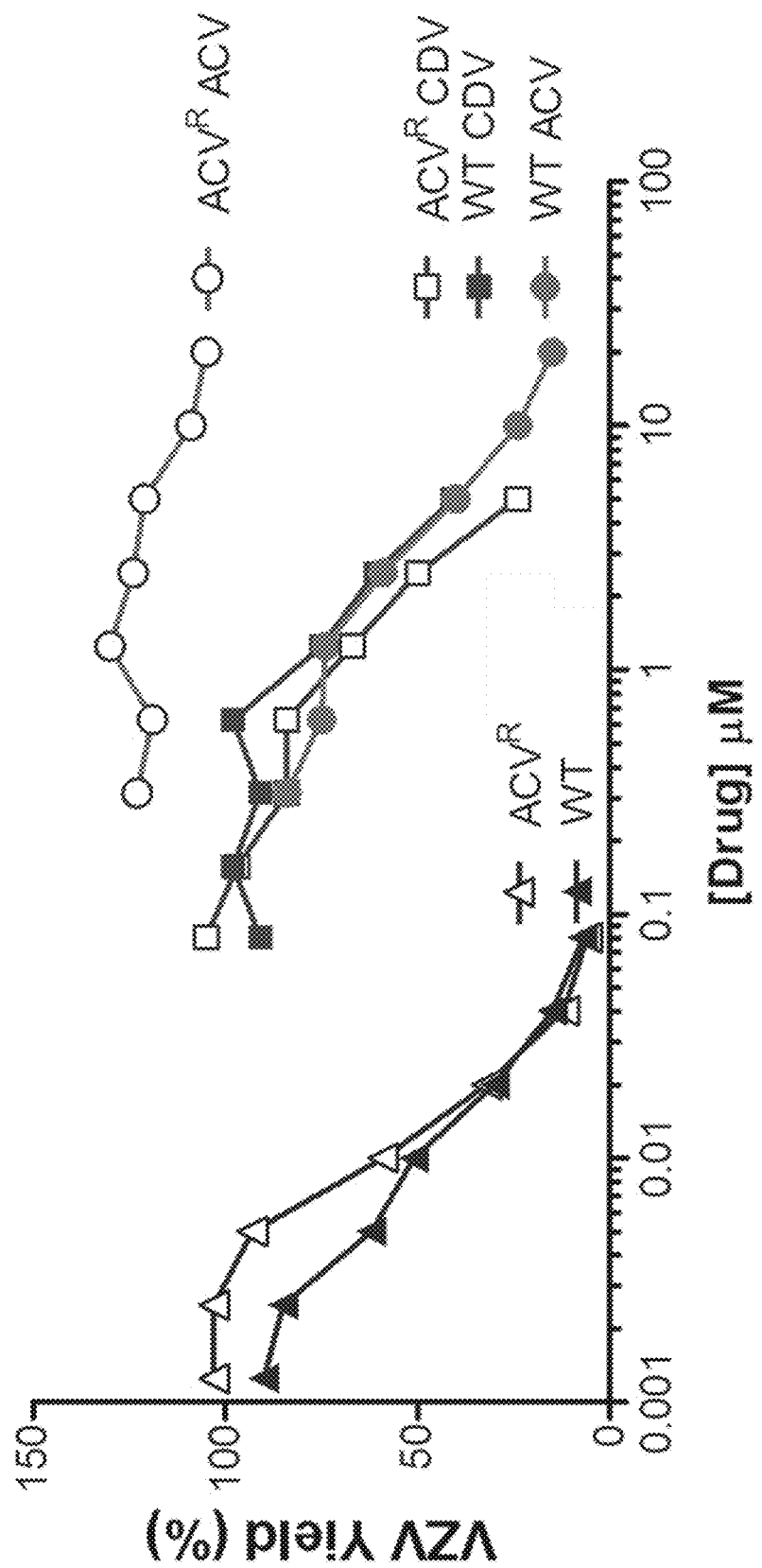
FIG. 1 is a graphic representation of the average of triplicate values compared to the average of the untreated samples, reported as virus yield percent.

The antiviral activity of compound (5) was evaluated in a cell-based assay using ARPE-19 cells, which are highly permissive for VZV replication, and the VZV-BAC-Luc strain (wild type). It was not known whether compound (5) would be active against a strain that was resistant to acyclovir due to a mutation in the thymidine kinase gene (ORF36). Thus we also included the ACV-resistant variant of VZV-BAC-Luc in this assay ($ACV^R$). Two control antiviral compounds, acyclovir (ACV) and cidofovir (CDV), were tested in the assay because the $ACV^R$ strain is sensitive to CDV due to the monophosphate on the cytidine analog. The ARPE-19 cells were inoculated with wild type or $ACV^R$ virus, and then triplicate samples were treated with compound (5), ACV, or CDV in the appropriate concentration range. After 3 days, bioluminescence was measured in the IVIS-50 instrument and the Total Flux was recorded. The average of triplicate values was compared to the average of the untreated samples, and then reported as the virus yield in percent (FIG. 1). The results with the $ACV^R$ strain are open symbols and the results with the wild type strain are solid symbols. As expected, the $ACV^R$ virus was resistant to ACV and the wild type virus was sensitive to ACV, with an approximate $EC_{50}$ of 2.5-5 µM. Cidofovir was effective against both virus strains, with an approximate $EC_{50}$ of 2.5 µM. Compound (5) was also effective against both wild type and $ACV^R$ viruses with an approximate EC50 of 0.01 µM (10 nM). Notably, compound (5) was nearly 100-times more potent than these approved antiviral drugs.

Figure 2:
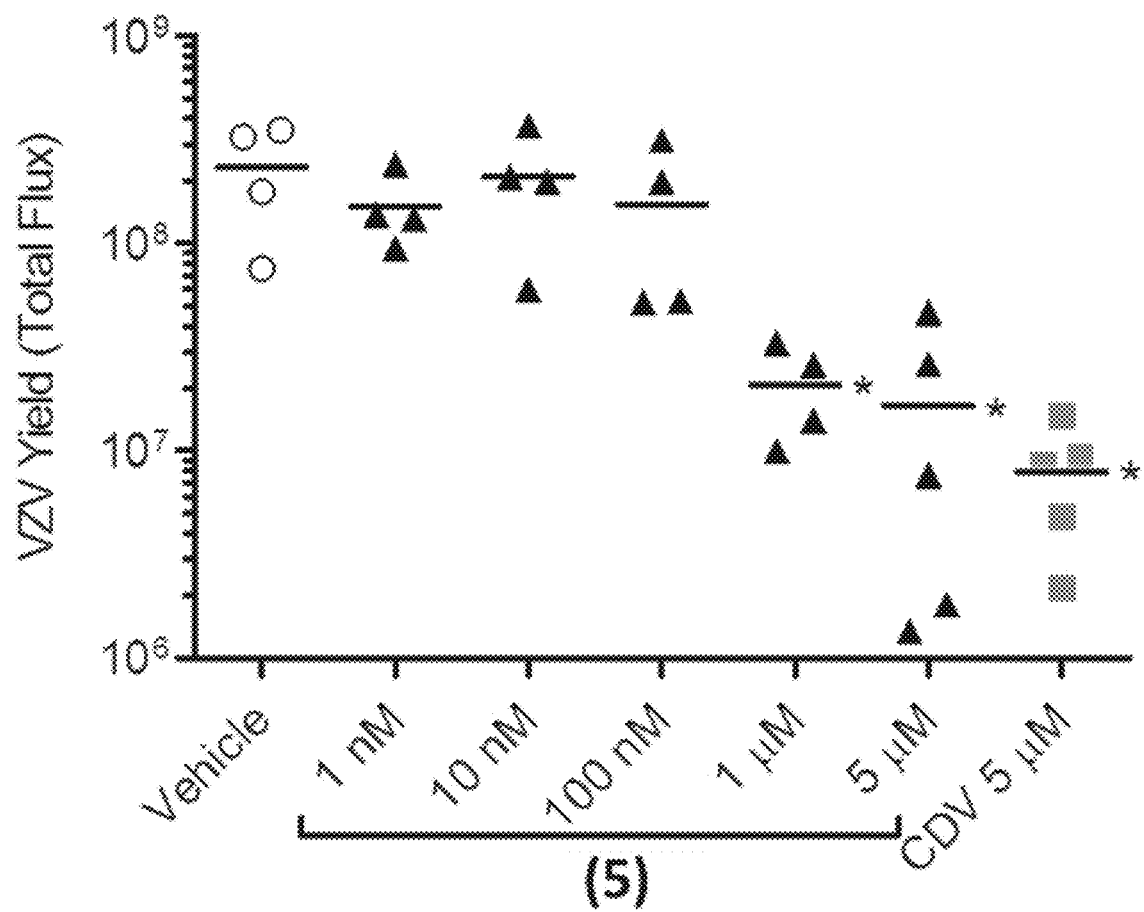
FIG. 2 is a graphic representation of the potency values for compounds in accordance with the claimed invention.

The highly potent activity of compound (5) warranted further evaluation in the skin organ culture model of VZV replication. This model employs full-thickness human skin that is maintained at the air-liquid interface above tissue culture medium. Small pieces of skin were inoculated with VZV-BAC-Luc by scarification, approximately 6000 pfu/piece, and then incubated overnight. On Day 1, the bioluminescence was measured in the IVIS-50 instrument to determine the initial level of VZV infection. Compound (5) was added to the medium in a range of concentrations from 1 nM to 5 µM. The positive control drug was cidofovir 5 µM. The Vehicle was 0.05% DMSO in tissue culture medium. Each group contained 4-6 pieces. The medium was changed each day to refresh the drugs, and the bioluminescence was measured by IVIS on Days 5, 7, 8, and 11. The values for each piece of skin are shown and the bar is the mean (FIG. 2). As expected, CDV 5 µM was effective after 11 days. 5 was effective at 1 and 5 µM, and this was significant compared to the vehicle (*, p<0.0001, 1-way ANOVA, Dunnett's post hoc test). The differences between CDV and the two highest concentrations of compound (5) were not significant. The skin organ culture assay provided valuable information about the potency of 5 in skin, which is a relevant tissue for VZV disease. Higher concentrations of 5 were required in skin than in cultured cells. We used this information to design the first evaluation of 5 in vivo.

Compound (5) was evaluated in the SCID-Hu mouse model of VZV replication (Rowe, J., R. J. Greenblatt, D. Liu and J. F. Moffat (2010). "Compounds that target host cell proteins prevent varicella-zoster virus replication in culture, ex vivo, and in SCID-Hu mice." *Antiviral Res* 86(3): 276-285). CB.17 scid/beige male mice were implanted subcutaneously with human fetal skin (the same type of specimens used for the skin organ culture assay). After 3-5 weeks engraftment period, the skin implants were inoculated with VZV-BAC-Luc. The mice were divided into 3 groups of 10-13 mice: vehicle (Cremophor-DMSO-saline 1:1:8), cidofovir 10 mg/kg in saline, and 5 26 mg/kg in Cremophor-DMSO-saline. 5 at 26 mg/kg is the molar equivalent dose to cidofovir 10 mg/kg. Cidofovir was given by the intraperitoneal route, once daily, from Days 0-8. Vehicle and 5 were given by the subcutaneous route, once daily, from Days 0-8. The mice were scanned in the IVIS-200 instrument daily from Day 1-9 and the Total Flux values indicated VZV-infected cells in the skin xenografts (FIG. 3). The left panel of FIG. 3 shows the average Total Flux values for each group, with error bars omitted for clarity. VZV grew normally in the Vehicle group. Both cidofovir and 5 prevented VZV spread during the treatment phase. Virus yield was compared on Day 9, and the absolute Total Flux values were significantly different between the Vehicle and drug treatment groups (* p=0.0051, 1-way ANOVA, Dunnett's post hoc test).

This was the first evaluation of 5 in vivo and it was not known whether the compound was overtly toxic to mice. The mice were weighed before the start of the study and daily during the treatment phase. Their change in weight during the treatment phase was compared to the initial weight and the average for the group is shown in FIG. 4 (error bars omitted for clarity). As expected, all mice lost weight after the inoculation surgery. Cidofovir caused moderate weight loss, which is typical of this nephrotoxic drug. Compound (5) did not cause weight loss and was indistinguishable from the Vehicle group. The mice appeared healthy and there were no signs of distress, such as ruffled fur, diarrhea, or hunched posture.

The in vivo evaluation of compound (5) was repeated to confirm its antiviral activity against VZV. In addition, a dose-ranging and delayed treatment assay was included to determine the lowest effective dose (FIGS. 5A and 5B). As before, 5 26 mg/kg was given once daily, by the subcutaneous route, from Days 0-6. This group was compared to Vehicle (Cremophor-DMSO-saline). In the dose ranging assay, 5 high dose (26 mg/kg), medium dose (13 mg/kg) or low dose (6.5 mg/kg) was given once daily, by the subcutaneous route, from Days 3-9. The treatment phase was delayed to Day 3 because this is more clinically relevant. Again, 5 was effective at 26 mg/kg given at the time of infection, and it prevented VZV spread in skin. Virus yield on Day 7, the day after treatment ended, was significantly less than the Vehicle group (p=0.008, Student's t test). The 26 mg/kg dose was also effective when treatment was delayed to Day 3. The medium and low doses of 5 were equally effective. Virus yield on Day 10, the day after treatment ended for these groups, was significantly less than the Vehicle group (p=0.029, 1-way ANOVA, Dunnett's post hoc test). These results indicate that 5 is highly potent against VZV in this mouse model, effectively preventing VZV spread at a low dose of 6.5 mg/kg.

The weight and condition of the mice was monitored in this assay, and compound (5) did not cause overt toxicity (FIG. 6). As before, the mice did not lose weight and they did not show signs of distress.

Compound (5) is highly active against VZV. It is approximately 100 times more potent than the commercially available drugs acyclovir and cidofovir in cultured cells. This may be due increased penetration through the cell membrane mediated by the hydrophobic moiety on the molecule. It may also be due to the uracil nucleotide analog, which is also highly potent in the drug brivudin that lacks a hydrophobic extension. Notably, Compound (5) is active against a VZV strain that lacks thymidine kinase activity, rendering it effective against viruses that acquire resistance to acyclovir and its derivatives by mutation in the TK gene.

Compound (5) is effective against VZV in the skin organ culture model, but less potent than in cultured cells. Compound (5) prevents VZV spread in skin at 1 µM and higher, which is approximately 10 times greater than the amount needed to fully inhibit VZV in cells. A possible explanation is that the number of cells is greater in the skin explants, which are at least 200 cubic millimeters, than in the cell cultures. The skin also contains adipose cells that may absorb 5 based on its hydrophobic properties. Thus more molecules of 5 may be needed to reach the VZV-infected dermal fibroblasts and the epidermal keratinocytes.

Compound (5) is effective against VZV in the SCID-Hu mouse model of VZV replication. The highest dose of 5 tested, 26 mg/kg/day, the molar equivalent of cidofovir 10 mg/kg/day, prevented VZV spread when given at the time of virus infection, Day 0, and three days after infection. Lower doses, 13 mg/kg/day and 6.5 mg/kg/day, were also effective given three days after infection. Compound (5) is superior to cidofovir because it is more potent and it does not cause weight loss.

In summary, Compound (5) is effective in vivo and is and well-tolerated.

III—Anti-HBV Activity

Protocol

Phenotypic drug resistance testing was performed in hepatocarcinoma cell line Huh7 in presence of a gradient of concentration of drugs. Drugs stock solution were prepared at $4 \cdot 10^7$ nM in DMSO, then aliquoted and stored at −20° C. Huh7 cell line was grown in DMEM medium (ThermoFischer Scientific) supplemented with 10% foetal calf serum (ThermoFischer Scientific), at 37° C. with 5% CO2. At day 0, Huh7 cells were seeded at density of 10 500 cells per well of a 96 wells plate. 100 ng/well of pHBV1.1× were transfected in these cells using Fugene 6 (Promega), according to the manufacturer's protocol. Drugs were added to the cells at a final concentration ranging from 32 to 100 000 nM. All experiments included two negative controls (pCIHBVΔRT and untransfected cells) and one positive control (pGFP encoding green fluorescent protein). All drug concentrations were tested in triplicates. Further steps were performed in level 3 biosafety laboratory, until cell lysis. At day 1 and 4, cell culture medium was removed and replaced with fresh medium and drugs. At day 7, medium was removed and cells were washed twice with PBS. Cellular and viral membranes were lysed with one freeze-thaw cycle at −80° C. and 37° C., followed by a 5 min incubation in IGEPAL® CA-630 1% (Sigma Aldrich). Lysate was clarified by centrifugation at 600 g for 5 min. 10 µL of supernatant were treated with 2U of RQ1 DNase (Promega) for 3 h at 37° C. Intra-capsid viral DNA was extracted with 30 µL of Quickextract (Epibio), according to manufacter's protocol. HBV and AMP DNA were quantified on this extract by duplex real-time PCR using 900 nM primers and 450 nM probes, 5 µL of DNA extract and 12.5 µL TaqMan Universal PCR mastermix II without UNG (ThermoFischer Scientific). Cycling reactions were performed on LightCycler 480 (Roche) with the following cycle parameters: 10 min at 95° C., followed by 45 cycles of 15 s at 95° C., 30 s at 60° C., 30 s at 72° C. Inhibitory concentrations 50% (IC50) were determined by non-linear regression using GraphPad Prism v5.0. Best fit values were obtained by least square regression with two constraints, bottom and top of the curve equal to 0 and 100%, respectively.

Results

|  | IC50 (nM) |
| --- | --- |
| Compound 5 | 400 |
| Compound 13 | 1 600 |

The results are also shown in FIGS. 7 to 10.

FIGS. 7 and 8 concern compound 5 and compound 13, respectively.

FIG. 9 concerns the HBV replication of compounds 5 and 13.

FIG. 10 concerns the cytotoxicity of compounds 5 and 13.

The invention claimed is:

1. A compound having the following formula (I'):

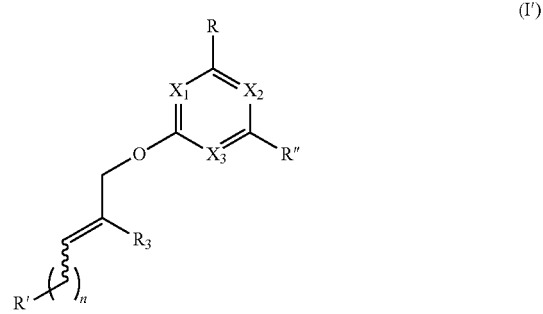

wherein:

n is 0, 1 or 2;

$X_1$, $X_2$, and $X_3$ are, independently from each other, CH or N;

R" is selected from the group consisting of: H, $NH_2$, and halogen atoms;

R is selected from the group consisting of:
— $NR_aR_b$ groups, $R_a$ and $R_b$ being independently from each other H, a ($C_1$-$C_6$)alkyl group or a ($C_3$-$C_6$) cycloalkyl group;
halogen atoms; and
($C_1$-$C_6$)alkoxy groups;

R' is a group of formula (1)

wherein $R_1$ and $R_2$ are independently from each other selected from the group consisting of:

OH;

($C_1$-$C_6$)alkoxy groups;

—O-$A_1$-O-$A_2$ groups; wherein $A_1$ is an alkylene radical comprising from 1 to 6 carbon atoms, and $A_2$ is a ($C_1$-$C_{20}$)alkyl group;

—O-$A_3$-O—C(=O)-$A_4$, wherein $A_3$ is an alkylene radical comprising from 1 to 6 carbon atoms, and $A_4$ is a ($C_1$-$C_6$)alkyl group; and —O-$A_5$-O—C(=O)—O—$A_6$, wherein $A_5$ is an alkylene radical comprising from 1 to 6 carbon atoms, and $A_6$ is a ($C_1$-$C_6$)alkyl group;

or R' is a group of formula (2):

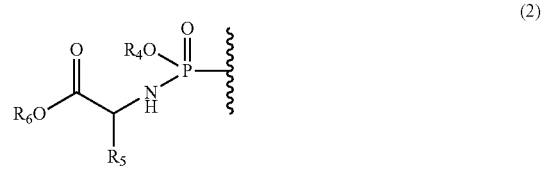

wherein:

$R_4$ is a ($C_6$-$C_{10}$)aryl group;

$R_5$ is a ($C_1$-$C_6$)alkyl group, $R_6$ is selected from the group consisting of: ($C_1$-$C_6$)alkyl groups, and ($C_6$-$C_{10}$)aryl groups, $R_3$ is selected from the group consisting of:

H;

$(C_1-C_6)$alkyl groups;

-$A_7$-OH, wherein $A_7$ is an alkylene radical comprising from 1 to 6 carbon atoms; and -$A_8$-O—C(=O)-$A_9$, wherein $A_8$ is an alkylene radical comprising from 1 to 6 carbon atoms, and $A_9$ is a $(C_1-C_6)$alkyl group;

or a pharmaceutically acceptable salt, racemate, diastereoisomer or enantiomer thereof.

2. The compound of claim 1, having one of the following formulae (II) or (II'):

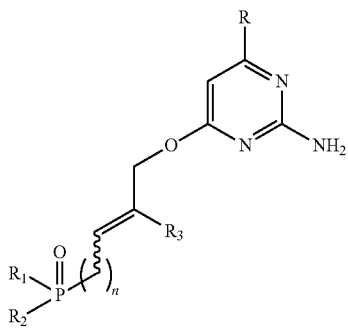
(II)

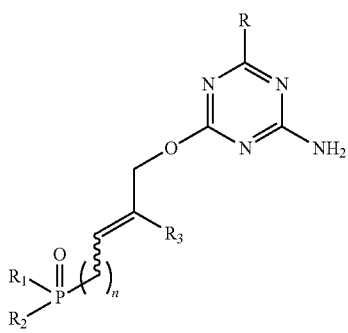
(II')

or a pharmaceutically acceptable salt, racemate, diastereoisomer or enantiomer thereof.

3. The compound of claim 1, having one of the following formulae (III) or (III'):

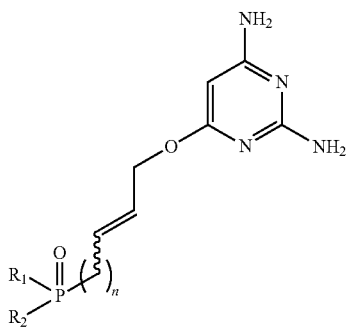
(III)

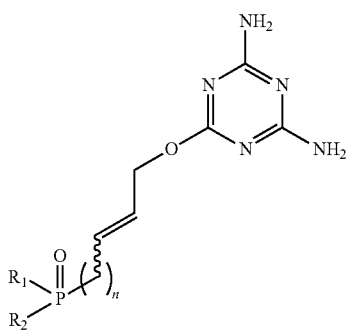
(III')

or a pharmaceutically acceptable salt, racemate, diastereoisomer or enantiomer thereof.

4. The compound of claim 1, having the following formula (IV):

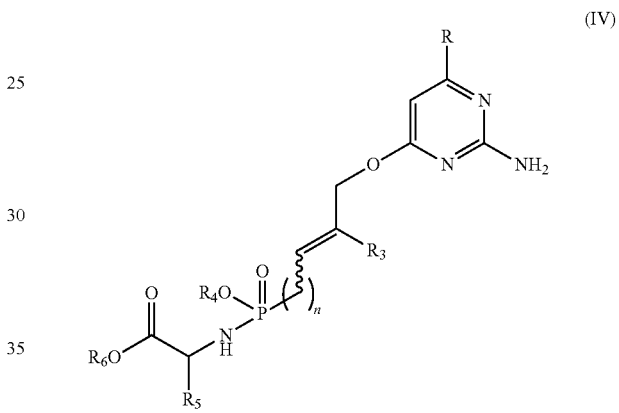
(IV)

or a pharmaceutically acceptable salt, racemate, diastereoisomer or enantiomer thereof.

5. A medicament comprising a compound according to claim 1, or a pharmaceutically acceptable salt thereof.

6. The compound of claim 1, wherein $R_1$ and $R_2$, identical or different, are selected from the group consisting of:
—O-$A_1$-O-$A_2$,
—O-$A_3$-O—C(=O)-$A_4$, and
—O-$A_5$-O—C(=O)—O—$A_6$ groups.

7. The compound of claim 1, wherein $R_1$ and $R_2$, identical or different, are selected from the group consisting of:
—O—$(CH_2)_3$—O—$(CH_2)_{15}$—$CH_3$,
—O—$CH_2$—O—C(=O)-tBu, and
—O—$CH_2$—O—C(=O)—O—iPr.

8. The compound of claim 1, wherein R is $NH_2$.

9. The compound of claim 1, wherein $R_3$ is H or —$CH_2OCOCH_3$.

10. The compound of claim 4, wherein $R_3$ is H or —$CH_2OCOCH_3$.

11. The compound of claim 4, wherein $R_4$ is a phenyl or naphthyl group.

12. A method for treating a viral infection, comprising administering a pharmaceutically acceptable amount of at least one compound of claim 1 to a patient in need thereof.

13. The method of claim 12, wherein the viral infection is an infection due to a DNA virus or an RNA virus.

14. The method of claim 12, wherein the viral infection is an infection due to a virus selected from the group consisting of Hepatitis B virus, Varicella-zoster virus, Cytomegalovirus, Adenovirus, Herpes virus, Poxvirus, Feline corona virus, Filovirus, Papovarirus, Parvovirus, Myxoma virus, and Hepadnavirus.

\* \* \* \* \*